US012630606B2

(12) United States Patent
　　Sgourakis

(10) Patent No.: US 12,630,606 B2
(45) Date of Patent: *May 19, 2026

(54) PEPTIDE DEFICIENT-MHC CLASS I/CHAPERONE COMPOSITIONS AND METHODS

(71) Applicant: The Regents of the University of California, Oakland, CA (US)

(72) Inventor: Nikolaos Sgourakis, Philadelphia, PA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/482,755

(22) Filed: Oct. 6, 2023

(65) Prior Publication Data

US 2024/0294601 A1　　Sep. 5, 2024

Related U.S. Application Data

(63) Continuation of application No. 17/256,162, filed as application No. PCT/US2019/040616 on Jul. 3, 2019, now Pat. No. 11,814,420.

(60) Provisional application No. 62/846,299, filed on May 10, 2019, provisional application No. 62/694,824, filed on Jul. 6, 2018.

(51) Int. Cl.
| | |
|---|---|
| *C07K 14/74* | (2006.01) |
| *A61K 39/00* | (2006.01) |
| *B01J 19/00* | (2006.01) |
| *C40B 30/04* | (2006.01) |

(52) U.S. Cl.
　　CPC .... *C07K 14/70539* (2013.01); *A61K 39/0011* (2013.01); *B01J 19/0046* (2013.01); *C40B 30/04* (2013.01); *B01J 2219/00725* (2013.01)

(58) Field of Classification Search
　　None
　　See application file for complete search history.

(56) References Cited

U.S. PATENT DOCUMENTS

| | | | |
|---|---|---|---|
| 11,814,420 B2 | 11/2023 | Sgourakis | |
| 2013/0017213 A1 | 1/2013 | Liu et al. | |
| 2013/0171668 A1 | 7/2013 | Loset | |
| 2014/0127251 A1 | 5/2014 | Maeurer | |
| 2014/0186850 A1* | 7/2014 | Berniac | A61K 47/6835 435/6.19 |
| 2018/0180601 A1 | 6/2018 | Pedersen et al. | |
| 2018/0319870 A1 | 11/2018 | Amin | |
| 2020/0024654 A1* | 1/2020 | Heron | C12Q 1/6876 |
| 2021/0155670 A1 | 5/2021 | Sgourakis et al. | |
| 2021/0269503 A1 | 9/2021 | Sgourakis | |
| 2021/0371498 A1 | 12/2021 | Sgourakis | |
| 2021/0371499 A1 | 12/2021 | Sgourakis | |
| 2022/0042008 A1 | 2/2022 | Kleinman | |

FOREIGN PATENT DOCUMENTS

| | | |
|---|---|---|
| EP | 2127664 A1 | 12/2009 |
| WO | WO 2020/010261 | 7/2019 |
| WO | WO 2019/145509 | 8/2019 |
| WO | WO 2021/050792 | 3/2021 |
| WO | WO 2021/138685 | 7/2021 |
| WO | WO 2021/138688 | 7/2021 |
| WO | WO 2021/212085 | 10/2021 |

OTHER PUBLICATIONS

International Search Report and Written Opinion for corresponding PCT Application No. PCT/US2019/040616—9 pages (Nov. 18, 2019).
European Search Report for corresponding EP Patent Application No. EP 19831548—2 pages (Apr. 11, 2022).
International Search Report and Written Opinion for related PCT Application No. PCT/US20/50276—23 pages (Mar. 15, 2021).
International Search Report and Written Opinion for related PCT Application No. PCT/US21/12117—17 pages (May 21, 2021).
International Search Report and Written Opinion for related PCT Application No. PCT/US21/27841—15 pages (Oct. 1, 2021).
International Search Report and Written Opinion for related PCT Application No. PCT/US21/12114—17 pages (May 20, 2021).
Anjanappa et al., "Structures of peptide-free and partially loaded MHC class I molecules reveal mechanisms of peptide selection." Nature Comm. pp. 1-11 (2020).
Altman et al., "Phenotypic analysis of antigen-specific T lymphocytes." Science 274(5284):94-6 (1996).
Arstila et al., "A direct estimate of the human alphabeta T cell receptor diversity." Science 286: 958 (1999).
Bakker et al., "Conditional MHC class I ligands and peptide exchange technology for the human MHC gene products HLA-A1, -A3, -A11, and -B7." Proc. Natl. Acad. Sci. U. S. A. 105: 3825-3830 (2008).
Dash et al., "Quantifiable predictive features define epitope-specific T cell receptor repertoires." Nature 547(7661):89-93 (2017).
Garboczi et al., "HLA-A2-peptide complexes: refolding and crystallization of molecules expressed in *Escherichia coli* and complexed with single antigenic peptides." Proc. Natl. Acad. Sci. 89: 3429-3433 (1992).
Glanville et al., "Identifying specificity groups in the T cell receptor repertoire." Nature 547: 94-98 (2017).

(Continued)

*Primary Examiner* — Christopher M Gross
(74) *Attorney, Agent, or Firm* — Morgan, Lewis, & Bockius LLP

(57) ABSTRACT

Compositions that include stable peptide deficient MHC class I/chaperone complexes and methods of making and using such complexes are provided. In particular embodiments, such peptide deficient MHC class I/chaperone complexes are used to form peptide MHC class I (pMHC-I) multimers useful for high throughput applications, such as, for the detection of antigen specific T cells and characterization of T cell profiles in subjects.

8 Claims, 22 Drawing Sheets

Specification includes a Sequence Listing.

(56)                    References Cited

OTHER PUBLICATIONS

Hafstrand et al., "Successive crystal structure snapshots suggest the basis for M HC class I peptide loading and editing by tapasin." PNAS vol. 116, No. 11, pp. 5055-5060 (2019).

Hansen "Preparation of Stable Single-Chain Trimers Engineered with Peptide, B2 Microglobulin, and MHC Heavy Chain" CPI 17.5.1-17.5.17; (2009).

Hermann et al., "The binding of TAPBPR and Tapasin to MHC class I is mutually exclusive." J. Immunol 191: 5743-5750 (2013).

Hermann et al., "TAPBPR alters MHC class I peptide presentation by functioning as a peptide exchange catalyst." eLIFE. vol. 4, p. 15 (2015).

HLA Nomenclature, "HLA Allele Nos. 2023" (2 pgs.) (2023).

Jantz-Naeem and Springer, "Venus flytrap or pas de trois? The dynamics of MHC class I molecules." Current Opinion in Immunology, 70: 82-89 (2021).

Jiang et al., "Crystal structure of a TAPBPR-MHC I complex reveals the mechanism of peptide editing in antigen presentation." Science 358: 1064-1068 (2017).

Jiang et al., "Crystal structure of a TAPBPR-MHC I complex reveals the mechanism of peptide editing in antigen presentation." Science 358: Supplemental Material (2017).

Johnson et al., "Gene transfer of tumor-reactive TCR confers both high avidity and tumor reactivity to nonreactive peripheral blood mononuclear cells and tumor-infiltrating lymphocytes." J. Immunol. Baltim. Md 1950 177: 6548-6559 (2006).

Jurewicz et al., "MHC-I peptide binding activity assessed by exchange after cleavage of peptide covalently linked to β2-microglobulin." Analytical Biochemistry, Amsterdam NL, 584: (2019).

Jurtz et al., "NetMHCpan-4.0: Improved Peptide-MHC Class I Interaction Predictions Integrating Eluted Ligand and Peptide Binding Affinity Data." J. Immunol. Baltim. Md 1950 199: 3360-3368 (2017).

Kalergis et al., "A simplified procedure for the preparation of MHC/peptide tetramers: chemical biotinylation of an unpaired cysteine engineered at the C-terminus of MHC-I." Journal of Immunological Methods 234 pp. 61-70 (2000).

Kawakami et al., "Identification of the immunodominant peptides of the MART-1 human melanoma antigen recognized by the majority of HLA-A2-restricted tumor infiltrating lymphocytes." J Exp Med. 180(1):347-52 (1994).

Khan et al., "The structure and stability of an HLA-A*0201/octameric tax peptide complex with an empty conserved peptide-N-terminal binding site." J. Immunol. 164: 6398-6405 (2000).

King et al., "Antibody-peptide-MHC fusion conjugates target non-cognate T cells to kill tumour cells." Cancer Immunol. Immunotherapy 62:6 (2013).

Kotsiou et al., "Dimerization of soluble disulfide trap single-chain major histocompatibility complex class I molecules dependent on peptide binding affinity." Antioxidants and Redox Signaling. 15:3 (2011).

Letournour et al., "Derivation of a T cell hybridoma variant deprived of functional T cell receptor alpha and beta chain transcripts reveals a nonfunctional alpha-mRNA of BW5147 origin." Eur J Immunol. 19(12):2269-74 (1989).

Li et al., "Three-dimensional structure of H-2Dd complexed with an immunodominant peptide from human immunodeficiency virus envelope glycoprotein 120." J. Mol. Biol. 283: 179-191 (1998).

Li et al., "Engineering superior DNA vaccines: MHC class I single chain trimers bypass antigen processing and enhance the immune response to low affinity antigens." Vaccine., 28, pp. 1911-1918 (2010).

Lumistra et al., "A flexible MHC class I multimer loading system for large-scale detection of antigen-specific T cells." Journal of Experimental Medicine. 215:5, 1493-1504 (2018).

Mcshan et al., "Peptide exchange on MHC-I by TAPBPR is driven by a negative allostery release cycle." Nat. Chem. Biol. 14: 811-820 (2018).

Moritz et al., "High-throughput peptide-MHC complex generation and kinetic screenings of TCRs with peptide-receptive HLA-A*02:01 molecules." Science Immunology. 4:37 (2019).

Morozov et al., "Interaction of TAPBPR, a tapasin homolog, with MHC-I molecules promotes peptide editing." Proc. Natl. Acad. Sci. U. S. A. 113: E1006-1015 (2016).

Natarajan et al., "An allosteric site in the T-cell receptor Cβ domain plays a critical signaling role." Nat Commun. 8:15260 (2017).

Nerli et al., "Structure-Based Modeling of SARS-CoV-2 Peptide/HLA-A02 Antigens." Frontiers in Medical Technology. vol. 2 (2020).

Neveu et al., "Impact of CD8-MHC class I interaction in detection and sorting efficiencies of antigen-specific T cells using MHC class I/peptide multimers: contribution of pMHC valency." International Immunology. vol. 18, No. 7, pp. 1139-1145 (2006).

Ohashi et al., "Reconstitution of an active surface T3/T-cell antigen receptor by DNA transfer." Nature 316(6029):606-9 (1985).

O'rourke et al., "Production of soluble pMHC-I molecules in mammalian cells using the molecular chaperone TAPBPR." Protein Engineering Design. 32:12 (2019).

Ostermeir et al., "Coupling between side chain interactions and binding pocket flexibility in HLA-8*44:02 molecules investigated by molecular dynamics simulations." Molecular Immunology, 63:312-319 (2015).

Overall et al., "High Throughput pMHC-1 Tetramer Library Production Using Chaperone Mediated Peptide Exchange." bioRxiv, pp. 1-31 (2019).

Overall et al., "High throughput pMHC-1 tetramer library production using chaperone- mediated peptide exchange." Nature Communications. 11(1):1909 (2020).

Praest et al., "New insights into the structure of the MHC class I peptide-loading complex and mechanisms of TAP inhibition by viral immune evasion proteins." Mol. Immunol., Pergamon, GB, 113 (2018).

Saini et al., "Dipeptides promote folding and peptide binding of MHC class I molecules." PNAS vol. 110, No. 38, pp. 15383-15388 (2013).

Saini et al., "Dipeptides catalyze rapid peptide exchange on MHC class I molecules." Proc. Natl. Acad. Sci. U. S. A. 112: 202-207 (2015).

Saini et al., "Empty peptide-receptive MHC class I molecules for efficient detection of antigen-specific T cells." Science Immunology. 4:37 (2019).

Science Direct Topics, "Chaperone—An overview." Science Direct https://www.sciencedirect.com/topics/neuroscience/chaperone (2007) Definition which they reside and function, 9 pages (downloaded 2024).

Stoeckius et al., "Simultaneous epitope and transcriptome measurement in single cells." Nat Methods (9):865-868 (2017).

Takahashi et al., "An immunodominant epitope of the human immunodeficiency virus envelope glycoprotein gp160 recognized by class I major histocompatibility complex molecule-restricted murine cytotoxic T lymphocytes." Proc Natl Acad Sci USA 85(9):3105-9 (1998).

Thomas & Tampé, "Structure of the TAPBPR-MHC I complex defines the mechanism of peptide loading and editing." Science 358: 1060-1064 (2017).

Trautmann et al., "Dominant Tcr V alpha usage by virus and tumor-reactive T cells with wide affinity ranges for their specific antigens." Euro J Immunol. 32: 3181-3190 (2002).

* cited by examiner

| Peptide Index | TAMRA exchange T$_m$ (°C) | rhodamine exchange T$_m$ (°C) | IC$_{50}$ (nM) |
|---|---|---|---|
| NB1 | 58.8 ± 0.7 | 57.1 ± 0.1 | 13 |
| NB2 | 61.7 ± 0.7 | 58.7 ± 0.2 | 21 |
| NB3 | 61.7 ± 0.7 | 57.6 ± 0.8 | 9 |
| NB4 | 60.7 ± 0.7 | 58.1 ± 0.1 | 8 |
| NB5 | 59.8 ± 0.7 | 59.3 ± 0.3 | 21 |
| NB6 | 57.3 ± 0 | 53.9 ± 0.3 | 28 |
| NB7 | 60.2 ± 0 | 59.7 ± 0.2 | 30 |
| NB8 | 58.3 ± 0 | 58.2 ± 0.5 | 3 |
| NB9 | 59.8 ± 0.7 | 58.7 ± 0.4 | 4 |
| NB10 | 61.7 ± 0.7 | 58.5 ± 0.8 | 241 |
| NB11 | 63.7 ± 0.7 | 62.0 ± 0 | 6 |
| NB12 | 62.2 ± 1.4 | 60.2 ± 0.3 | 9 |
| NB13 | 58.8 ± 0.7 | 58.0 ± 0.4 | 26 |
| NB14 | 57.3 ± 1.4 | 56.8 ± 0.2 | 96 |
| NB15 | 61.2 ± 0 | 58.1 ± 0.4 | 18 |
| NB16 | 63.2 ± 0 | 61.1 ± 0.3 | 6 |
| NB17 | 64.2 ± 0 | 63.0 ± 0.03 | 3.4 |
| NB18 | 64.2 ± 0 | 61.1 ± 0.5 | 19 |
| NB19 | 61.7 ± 0.7 | 61.1 ± 0.4 | 33 |
| NB20 | 60.2 ± 0 | 60.5 ± 0.1 | 42 |
| NB21 | 58.8 ± 0.7 | 58.3 ± 0.2 | 48 |
| NB22 | 59.3 ± 0 | 58.6 ± 0.1 | 13 |
| NB23 | 60.7 ± 0.7 | 58.5 ± 0.5 | 13 |
| NB24 | 63.2 ± 1.4 | 60.8 ± 0.3 | 3 |
| NB25 | 63.7 ± 0.7 | 61.8 ± 0.3 | 14 |
| NB26 | 61.7 ± 0.7 | 60.1 ± 0.1 | 19 |
| NB27 | 53.3 ± 0 | 54.4 ± 0.2 | 480 |
| NB28 | 52.3 ± 0 | 52.7 ± 0.2 | 635 |
| NB29 | 58.3 ± 0 | 57.3 ± 0.1 | 4 |
| MART1 (reference) | 58.2 ± 0 | 56.1 ± 0.5 | 254 |

Figure 16

SEQ ID NO:20 - SEQ ID NO:53

Figure 18A - Figure 18E
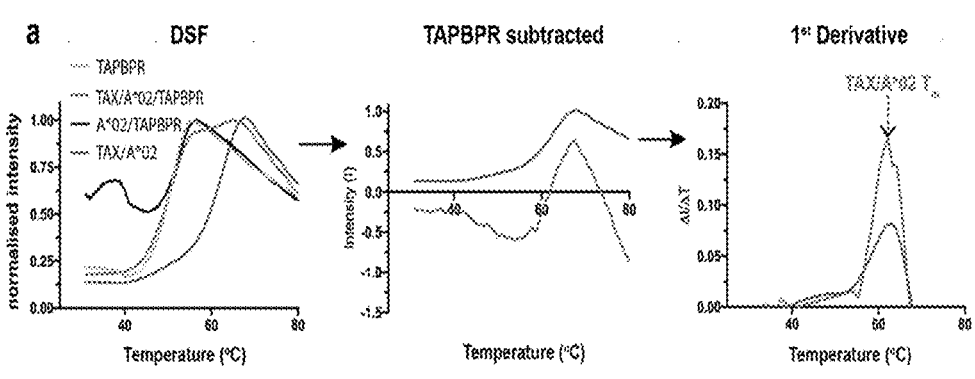
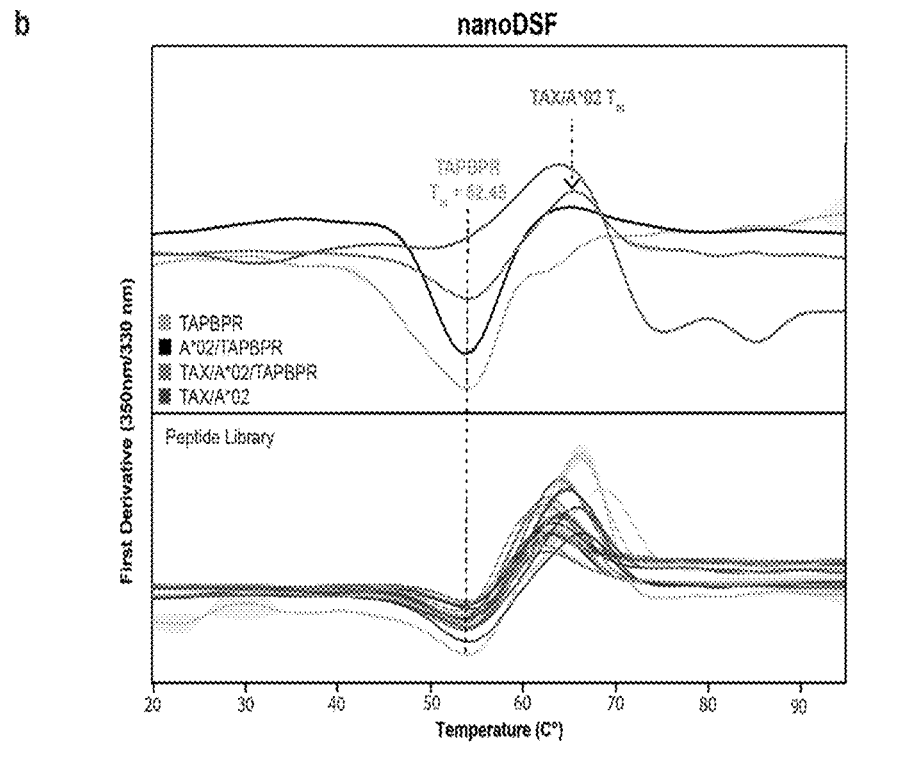
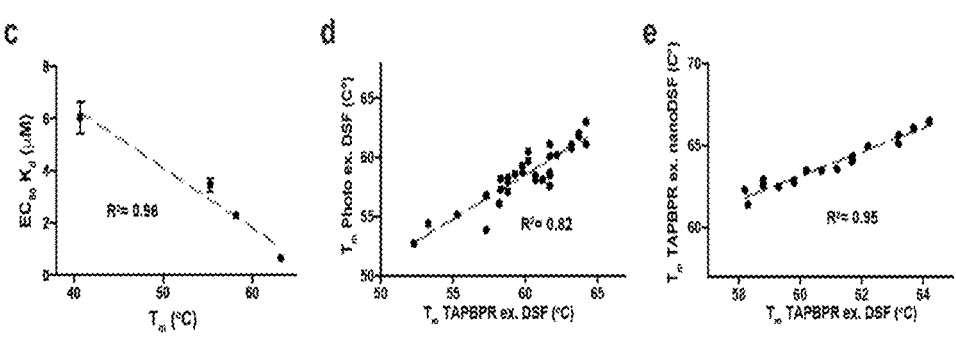

| | TRAV | TRAJ | CDR3 |
|---|---|---|---|
| SEQ ID NO:63 | V16 | J9 | CALMGGTGGFKTIF |
| SEQ ID NO:64 | V8-1 | J21 | CAGYNFNKFYF |
| SEQ ID NO:65 | V13-2 | J15 | CAETLNQAGTALIF |
| SEQ ID NO:66 | V8-1 | J34 | CAVKDTDKLIF |
| SEQ ID NO:66 | V8-1 | J34 | CAVKDTDKLIF |
| SEQ ID NO:66 | V8-1 | J34 | CAVKDTDKLIF |
| SEQ ID NO:66 | V8-1 | J34 | CAVKDTDKLIF |
| SEQ ID NO:67 | V26-2 | J54 | CILRDFQGAQKLVF |

PEPTIDE DEFICIENT-MHC CLASS I/CHAPERONE COMPOSITIONS AND METHODS

CROSS REFERENCE TO RELATED APPLICATIONS

This is a Continuation of U.S. patent application Ser. No. 17/256,162, filed Dec. 24, 2020, which is a 371 National Phase of PCT/US2019/040616, filed Jul. 3, 2019, which claims priority to U.S. Provisional Patent Application No. 62/694,824, filed Jul. 6, 2018, and U.S. Provisional Patent Application No. 62/846,299, filed May 10, 2019, all of which are hereby incorporated by reference.

REFERENCE TO SEQUENCE LISTING SUBMITTED ELECTRONICALLY

This application contains a Sequence Listing which has been submitted electronically in XML file format and is hereby incorporated by reference in its entirety. The XML file, named 116550-01-5008-US01_Corrected.xml, was created on May 28, 2024 and is 92 kilobytes in size.

BACKGROUND

Cytotoxic T cell activation occurs when a T cell, via its T cell receptor (TCR), recognizes an antigen peptide-MHC class I complex on an antigen presenting cell. Such TCR/peptide-MHC class I interactions are important, for example, for adaptive immunity against pathogens, for the recognition and elimination of tumor cells, as well as the pathogenesis of particular diseases (e.g., autoimmune diseases).

Antigen peptide-MHC class I multimer complexes are useful for the identification of antigen specific T cells, and antigens that activate such T cells. The identification of antigen specific T cells and corresponding antigens can then be used, for example, for the understanding of disease development, as well as in the development of T-cell based therapies (e.g., cancers), in both preclinical and clinical settings.

High-throughput screening strategies using large arrays of peptide-MHC class I multimers can advantageously allow for the large scale identification of antigen specific T-cells and/or antigens that bind to particular MHC class I. Such high-throughput screens, however, are limited by the ability to produce large collections of peptide-MHC class I multimers. The instability of peptide deficient MHC class I molecules, for example, makes large scale production of peptide-MHC class I multimers using such peptide deficient MHC class I molecules difficult to achieve.

To circumvent the problem of unstable peptide deficient MHC class I molecules, conditional MHC class I ligands are used. See, e.g., Rodenko et al., Nature Protocols 1(3): 1120-1132 (2006). Such conditional ligand bound to MHC class I can be cleaved by exposure to UV light, or to increased temperature (See, e.g., Luimstra et al., J. Exp. Med 215(5): 1493-1504 (2018)). Upon cleavage and in the presence of a peptide of interest, a net exchange occurs wherein the cleaved conditional ligand dissociates with the MHC class I and the peptide of interest associates with the MHC class I, thereby forming the desired peptide-MHC class I complex. Such conditional ligands, however, also have limitations. Conditional ligands almost always result in some sample aggregation and precipitation during the photolysis/peptide exchange step, due to the unstable nature of the transient peptide deficient MHC. Moreover, using suboptimal peptides can lead to high background levels of exchange. As such, there remains a need for new methods of making peptide-MHC class I complex libraries.

SUMMARY

Compositions that include stable peptide deficient MHC class I/chaperone complexes and methods of making and using such complexes are provided. In particular embodiments, such peptide deficient MHC class I/chaperone complexes are used to form peptide MHC class I (pMHC-I) multimers useful for high throughput applications, such as, for the detection of antigen specific T cells and characterization of T cell profiles in subjects.

In a first aspect, provided herein is a method of making a peptide-deficient MHC class I/chaperone complex. The method comprises: a) incubating an MHC class I heavy chain, an MHC class I light chain and a placeholder peptide under conditions wherein the MHC class I heavy chain, the MHC class I light chain and the placeholder peptide form a placeholder peptide-MHC class I (p*MHC I) complex; and b) contacting the placeholder peptide-MHC class I complex with a dipeptide and chaperone, thereby displacing the placeholder peptide from the placeholder peptide-MHC complex and forming the peptide deficient-MHC class I/chaperone complex.

In some embodiments, the MHC class I is a human HLA-A, HLA-B or HLA-C. In certain embodiments, the MHC class I is an HLA-A. In an exemplary embodiment, the MHC class I is HLA-01 or HLA-A02. In some embodiments, the MHC class I is a mouse H-2 molecule. In an exemplary embodiment, the H-2 is H-2D$^d$ or H-2L$^d$.

In certain embodiments, the MHC class I has one or more mutations in the α3 domain of the heavy chain. In some embodiments, the MHC class I is H-2D$^d$ or H-2L$^d$ and the one or more mutations in the α3 domain includes a mutation in M228. In particular embodiments, the mutation is an M228N, M228Q, M228S, M228T or M228Y amino acid substitution. In some embodiments, the MHC class I is a variant HLA-A01 (e.g., HLA-A*01:01) and the one or more mutations in the α3 domain includes a mutation in T228M.

In one embodiment, the placeholder peptide is a destabilizing placeholder peptide with a Tm value for the MHC class I of below 50° C. In certain embodiments, the MHC class I is H-2D$^d$ and the placeholder peptide is gP18-I10 (with sequence GPGRAFVTI) (SEQ ID NO:1). In some embodiments, the MHC class I is H-2L$^d$ and the placeholder peptide is QL9 (sequence QLSPFPFDL) (SEQ ID NO:2). In other embodiments, the MHC class I is HLA-A*02:01 and the placeholder peptide is gTAX (sequence LFGYPVYV) (SEQ ID NO:3) or AcLLFGYPVYV (SEQ ID NO:4), where AcL is a leucine amino acid with modified (acetylated) N-terminus.

In certain embodiments, the chaperone is Tapasin Binding Protein Related (TAPBPR). In some embodiments, the dipeptide is glycyl-methionine or glycyl-phenylalanine.

In an exemplary embodiment, the p*MHC I complex is purified and biotinylated prior to b) contacting with the dipeptide and chaperone.

In a second aspect, provided herein is a method of making a composition that includes a plurality of peptide-MHC class I (pMHC I) complexes, where each complex includes an MHC class I and a peptide of interest. In one embodiment, the method includes: a) incubating a plurality of MHC class I heavy chains, a plurality of MHC class I light chains and a plurality of placeholder peptides under conditions wherein the plurality of MHC class I heavy chains, MHC class I light chains and placeholder peptides form a plurality of placeholder peptide-MHC class I (p*MHC I) complexes; b) forming a plurality of peptide deficient-MHC class I/chaperone complexes by contacting the plurality of placeholder peptide-MHC class I complexes with a plurality of dipeptides and chaperones; and c). contacting the plurality of peptide deficient-MHC class I/chaperone complexes with a plurality of peptides of interest, thereby forming the composition.

In some embodiments, the MHC class I is a human HLA-A, HLA-B or HLA-C. In certain embodiments, the MHC class I is an HLA-A. In an exemplary embodiment, the MHC class I is HLA-A01 or HLA-A02. In some embodiments, the MHC class I is an H-2. In an exemplary embodiment, the H-2 is H-2D$^d$ or H-2L$^d$.

In certain embodiments, the MHC class I has one or more mutations in the α3 domain of the heavy chain. In some embodiments, the MHC class I is H-2D$^d$ or H-2L$^d$ and the one or more mutations in the α3 domain includes a mutation in M228. In particular embodiments, the mutation is an M228N, M228Q, M228S, M228T or M228Y amino acid substitution. In some embodiments, the MHC class I is a variant HLA-A01 (e.g., HLA-A*01:01) HLA-A*01:01 and the one or more mutations in the α3 domain includes a mutation in T228M.

In one embodiment, the placeholder peptide is a destabilizing placeholder peptide with a Tm value for the MHC class I of below 50° C. In certain embodiments, the MHC class I is H-2D$^d$ and the placeholder peptide is gP18-I10 (with sequence GPGRAFVTI) (SEQ ID NO:1). In some embodiments, the MHC class I is H-2L$^d$ and the placeholder peptide is QL9 (sequence QLSPFPFDL) (SEQ ID NO:2). In other embodiments, the MHC class I is HLA-A*02:01 and the placeholder peptide is gTAX (sequence LFGYPVYV) (SEQ ID NO:3) or AcLLFGYPVYV (SEQ ID NO:4), where AcL is a leucine amino acid with modified (acetylated) N-terminus.

In certain embodiments, the chaperone is Tapasin Binding Protein Related (TAPBPR).

In some embodiments, the dipeptide is glycyl-methionine or glycyl-phenylalanine.

In certain embodiments, the plurality of peptides of interest have the same sequence. In some embodiments, at least two of the peptides of interest in the plurality of peptides of interest have different sequences. In some embodiments, the plurality of peptides of interest are tumor antigen peptides. In an exemplary embodiment, the plurality of p*MHC I complexes are purified and biotinylated prior to b) contacting with the plurality of dipeptides and chaperones.

In a third aspect, provided herein is a method of making a composition comprising a plurality of peptide-MHC class I (pMHC-I) multimer complexes, each complex comprising an MHC class I multimer and a peptide of interest. In some embodiments, the method includes: a) incubating a plurality of MHC class I heavy chains, a plurality of MHC class I light chains and a plurality of placeholder peptides under conditions wherein the plurality of MHC class I heavy chains, MHC class I light chains and the placeholder peptides form a plurality of placeholder peptide-MHC class I complexes (p*MHC-I); b) forming a plurality of peptide deficient MHC class I/chaperone complexes by contacting the plurality of placeholder peptide-MHC class I complexes (p*MHC-I) with a plurality of dipeptides and chaperone; c) attaching the plurality of peptide deficient MHC class I/chaperone complexes to backbones, thereby forming a plurality of peptide deficient MHC class I/chaperone multimer complexes; and d) contacting the plurality of peptide deficient-MHC class I/chaperone multimer complexes with a plurality of peptides of interest, thereby forming the plurality of peptide-MHC class I multimer complexes and free chaperones. In some embodiments, the free chaperones are removed. In particular embodiments, the free chaperones are removed by spin column dialysis.

In some embodiments, the MHC class I is a human HLA-A, HLA-B or HLA-C. In certain embodiments, the MHC class I is an HLA-A. In an exemplary embodiment, the MHC class I is HLA-A01 or HLA-A02. In some embodiments, the MHC class I is an H-2. In an exemplary embodiment, the H-2 is H-2D$^d$ or H-2L$^d$.

In certain embodiments, the MHC class I has one or more mutations in the α3 domain of the heavy chain. In some embodiments, the MHC class I is H-2D$^d$ or H-2L$^d$ and the one or more mutations in the α3 domain includes a mutation in M228. In particular embodiments, the mutation is an M228N, M228Q, M228S, M228T or M228Y amino acid substitution. In some embodiments, the MHC class I is a variant HLA-A01 (e.g., HLA-A*01:01) and the one or more mutations in the α3 domain includes a mutation in T228M.

In one embodiment, the placeholder peptide is a destabilizing placeholder peptide with a Tm value for the MHC class I of below 50° C. In certain embodiments, the MHC class I is H-2D$^d$ and the placeholder peptide is gP18-I10 (with sequence GPGRAFVTI) (SEQ ID NO:1). In some embodiments, the MHC class I is H-2L$^d$ and the placeholder peptide is QL9 (sequence QLSPFPFDL) (SEQ ID NO:2). In other embodiments, the MHC class I is HLA-A*02:01 and the placeholder peptide is gTAX (sequence LFGYPVYV) (SEQ ID NO:3) or AcLLFGYPVYV (SEQ ID NO:4), where AcL is a leucine amino acid with modified (acetylated) N-terminus.

In certain embodiments, the chaperone is Tapasin Binding Protein Related (TAPBPR). In some embodiments, the dipeptide is glycyl-methionine or glycyl-phenylalanine.

In certain embodiments, the plurality of the peptides of interest have the same sequence. In some embodiments, the plurality of the peptides of interest have different sequences. In some embodiments, each of the MHC tetramer-peptide complexes is further attached to a barcode DNA oligonucleotide. In certain embodiments, the backbones are selected from streptavidin, avidin and dextran backbones. In some embodiments, the p*MHC-I are biotinylated prior to forming the plurality of the peptide deficient MHC-chaperone complexes. In an exemplary embodiment, the multimer is a tetramer.

In a fourth aspect, provided herein is a composition that includes a plurality of purified and stable peptide deficient-MHC class I/chaperone complexes, wherein each purified complex includes a peptide deficient MHC class I and a chaperone. In some embodiments, the complexes are solubilized in a solution at a concentration of up to 1 mM and do not form a precipitate when stored at 4° C.

In some embodiments, the MHC class I is a human HLA-A, HLA-B or HLA-C. In certain embodiments, the MHC class I is an HLA-A. In an exemplary embodiment, the MHC class I is HLA-A01 or HLA-A02. In certain embodiments, the MHC class I is a variant MHC class I that has one or more mutations in the α3 domain of the heavy chain. In some embodiments, the MHC class I is a variant H-2D$^d$ or H-2L$^d$ and the one or more mutations in the α3 domain includes a mutation in M228. In particular embodiments, the mutation is an M228N, M228Q, M228S, M228T or M228Y amino acid substitution. In some embodiments, the MHC class I is a variant HLA-A01 (e.g., HLA-A*01:01) and includes a T228M mutation in the α3 domain.

In a fifth aspect, provided herein is a method of making a library of MHC class I tetramer antigen peptide (pMHC-I) multimer complexes, wherein each pMHC-I multimer complex in the library comprises an MHC class I multimer and a peptide of interest from a plurality of peptides of interest. In some embodiments, the method includes: a) incubating a plurality of MHC class I heavy chains, a plurality of MHC class I light chains and a plurality of placeholder peptides under conditions wherein the plurality of MHC class I heavy chains, MHC class I light chains and placeholder peptides form a plurality of placeholder peptide-MHC class I (p*MHC-I) complexes; b) forming a plurality of peptide deficient-MHC class I/chaperone complexes by contacting the plurality of placeholder peptide-MHC class I (p*MHC-I) complexes with a plurality of dipeptides and chaperones; c) multimerizing the peptide deficient-MHC class I/chaperone multimer complexes, wherein each peptide deficient-MHC class I/chaperone multimer complex comprises a backbone comprising a detectable label; and d) contacting each of the peptide deficient-MHC class I/chaperone multimer complexes with an peptide of interest from the plurality of peptides of interest, thereby forming a plurality of peptide-MHC class I multimer complexes and free chaperones. In one embodiment, at least two of the peptide-MHC class I multimer complexes include a different antigen peptide of interest. In certain embodiments, the library of peptide-MHC class I (pMHC-I) multimer complexes include at least 10, 20, 30, 40, 50, 60, 70, 80, 90, 100, 200, 300, 400, 500, 600, 700, 800, 900, 1,000 different peptide-MHC class I multimer complexes, wherein each peptide-MHC class I multimer complex includes a different antigen peptide. In some embodiments, the free chaperones are removed. In particular embodiments, the free chaperones are removed by spin column dialysis.

In a sixth aspect, provided herein is a method of screening a sample of T cells for antigen specific T cells that bind to one or more antigen peptides from a plurality of peptide of antigens of interest. In some embodiments, the method includes: a) contacting the sample with the library of peptide-MHC class I multimer complex provided herein; and b) detecting the presence of T cells in the sample that bind to one or more of the peptide-MHC class I multimer complexes using the detectable agent.

In certain embodiments, the detectable agent is a fluorophore or a nucleic acid barcode and the detecting step b) is performed using flow cytometry. In some embodiments, the method further includes the step of identifying the peptide of a peptide-MHC class I multimer complex bound to a T cell in the sample by determining the nucleic acid barcode of peptide-MHC class I multimer complex. In an exemplary embodiment, the step of determining the sequence of the T cell receptor (TCR) of a T cell in the sample that binds a MHC class I tetramer-antigen peptide complex is performed using V(D)J sequencing. In one embodiment, the detectable agent of each of the peptide-MHC class I multimer complex in the plurality of peptide-MHC class I multimer complexes corresponds to different antigen peptide of interest.

In some embodiments, the MHC class I is a human HLA-A, HLA-B or HLA-C. In certain embodiments, the MHC class I is an HLA-A. In an exemplary embodiment, the MHC class I is HLA-A01 or HLA-A02. In some embodiments, the MHC class I is H-2D$^d$ or H-2L$^d$. In certain embodiments, the MHC class I is a variant MHC class I that includes one or more mutations in the α3 domain of the heavy chain. In an exemplary embodiment, the MHC class I is a variant H-2D$^d$ or H-2L$^d$ that includes a mutation in M228 in the α3 domain. In particular embodiments, the mutation is an M228N, M228Q, M228S, M228T or M228Y amino acid substitution. In some embodiments, the MHC class I is a variant HLA-A01 (e.g., HLA-A*01:01) that includes a T228M mutation in the α3 domain.

In one embodiment, the placeholder peptide is a destabilizing placeholder peptide with a Tm value for the MHC class I of below 50° C. In certain embodiments, the MHC class I is H-2D$^d$ and the placeholder peptide is gP18-I10 (with sequence GPGRAFVTI) (SEQ ID NO:1). In some embodiments, the MHC class I is H-2L$^d$ and the placeholder peptide is QL9 (sequence QLSPFPFDL) (SEQ ID NO:2). In other embodiments, the MHC class I is HLA-A*02:01 and the placeholder peptide is gTAX (sequence LFGYPVYV) (SEQ ID NO:3) or AcLLFGYPVYV (SEQ ID NO:4), where AcL is a leucine amino acid with modified (acetylated) N-terminus.

In certain embodiments, the chaperone is Tapasin Binding Protein Related (TAPBPR). In some embodiments, the dipeptide is glycyl-methionine or glycyl-phenylalanine.

In some embodiments of the method, each of the peptides in the plurality of peptides is derived from a tumor antigen peptide. In certain embodiments, the sample is from a human.

In an exemplary embodiment, the detectable agent is a nucleic acid barcode. In certain embodiments, the detectable agent is a fluorophore. In some embodiments, the peptide-MHC class I multimer complexes comprising the same antigen peptide comprise the same detectable label. In particular embodiments, the peptide-MHC class I multimer complexes comprising different antigen peptides comprise different detectable labels.

In an exemplary embodiment, the multimer is a tetramer. In some embodiments, the plurality of p*MHC I complexes are purified and biotinylated prior to b) contacting with the plurality of dipeptides and chaperones.

BRIEF DESCRIPTION OF THE DRAWINGS

FIG. 1A depicts contacts between the TAX$_{11-19}$ peptide (cyan sticks) and the MHC-I peptide-binding groove (purple cartoon) as shown in the X-ray 3D structure of HLA-A*02:01/TAX$_{11-19}$ (PDB ID 1DUY). FIG. 1B depicts the X-ray 3D structure of a single amino acid N-terminal truncation of an exemplary placeholder peptide, the TAX$_{12-19}$ peptide (PDB: 1DUY), shown as green sticks embedded in the HLA-A*02:01 groove. MHC groove shown as light purple cartoons with residues forming polar contacts with the TAX peptide highlighted in dark purple. Yellow dashes represent polar contacts between the peptides and the A- or B-specificity pockets of the MHC-I groove. FIG. 1C depicts a schematic of TAPBPR-mediated peptide dissociation, used here to prepare a peptide-deficient complex. FIG. 1D depicts the purification of a peptide deficient TAPBPR/HLA-A*02:01 complex (Blue, 26.5 minutes), TAPBPR (Sky Blue, 28.1 min), and HLA-A:02:01/TAX$_{12-19}$ (Red, 30.9 min) using a Superdex 200 10/300 size exclusion column run at a flow rate of 1 mL/min. SDS-Page gel electrophoresis confirms the presence of the expected molecular species.

FIG. 2A-FIG. 2C. FIG. 2A depicts a native gel electrophoresis following a titration of TAX$_{11-19}$ peptide on peptide deficient, HLA-A*02:01/TAPBPR complex, showing dissociation of the complex into the individual pMHC-I and TAPBPR components. FIG. 2B depicts size-exclusion chromatography traces (1 ml/min flow rate), shows that addition of 50-fold molar excess of synthetic TAX peptide (blue) completely dissociates the peptide-receptive complex sample (yellow) into TAPBPR (purple) and pMHC-I (red) molecular species. FIG. 2C depicts an LC/MS analysis of the purified pMHC-I (red) confirms capture of the TAX peptide in the HLA-A*02:01, and thereby confirming that the peptide deficient MHC-I/TAPBPR complex is also peptide receptive. The top panel shows the chromatogram trace while the bottom panel the average relative mass abundance from 17 min to 18 mins, showing a peak on the expected molecular mass of the TAX peptide (1,069 Da).

FIG. 5A is an electrophoresis using a 2% agarose gel, showing that a biotinylated DNA oligo (lower band) readily binds to Streptavidin-PE (top band). The streptavidin-PE: biotinylated DNA oligo molar ratio used is indicated, for each sample.

FIG. 6A shows an LC/MS analysis of purified HLA-A*02:01/ $TAX_{12-19}$ and FIG. 6B shows an LC/MS analysis of purified HLA-A*02:01/TAPBPR complex. The top panels show the chromatogram trace of the pMHC-I or the TAPBPR/MHC-I complex, while the lower panels show the mass abundance for the time interval between 16.5 and 17.5 minutes, showing that the TAPBPR-chaperoned MHC-I is peptide-deficient.

FIG. 15 is a table summarizing pMHC $T_m$ values of neuroblastoma neoepitopes included in Library 1. Conventional DSF was performed on pHLA-A*02:01 samples prepared by either TAPBPR-mediated peptide exchange (column 2), or exchange using UV irradiation of a photosensitive conditional peptide ligand (column 3). A 20-fold molar excess of free peptide was used to promote exchange during a 1 hr incubation at room temperature, for all experiments. DSF profiles were analysed as shown in FIG. 18. All measurements were performed in PBS buffer. Errors represent the standard deviation of 3 replicates, individually analysed. $IC_{50}$ values were derived from the NetMHC 4.0 Server (Andreatta, *Bioinformatics* February 15: 32(4):511-7 (2016); and Nielsen et al., *Protein Sci.,* 12: 1007-17 (2003)).

FIG. 16 is a table summarizing pMHC $T_m$ values of viral, tumor, autoimmune epitopes included in Library 2. Conventional DSF was performed on HLA-A*02:01/TAPBPR complexes following 1 hr incubation with each listed peptide. A 20-fold molar excess of free peptide was used to promote exchange during a 1 hr incubation at room temperature, for all experiments. DSF profiles were analysed as shown in FIG. 18A. Measurements were performed in PBS buffer supplemented with 0.5% DMSO to increase peptide solubility. Errors represent the standard deviation of 3 replicates, individually analysed. $IC_{50}$ values were obtained from NetMHC 4.0 (Andreatta, *Bioinformatics* February 15: 32(4): 511-7 (2016); and Nielsen et al., *Protein Sci.,* 12: 1007-17 (2003)).

FIG. 18A-FIG. 18E provide a summary of a study showing high-throughput validation of peptide loading on HLA-A*02:01/TAPBPR complexes using differential scanning Fluorimetry (DSF). (a) Derivation of melting temperatures for TAPBPR exchanged TAX/HLA-A*02:01 from conventional DSF data. The DSF trace of TAPBPR alone (left, orange line) was subtracted from that of TAPBPR exchanged HLA-A*02:01 (red line) to obtain the subtracted curve (center, red line). The $T_m$ can be extracted by taking the first derivative (right, red line). As a reference the DSF trace of TAX/HLA-A*02:01 is processed in the manner but without removing the TAPBPR trace (blue line). (b) (upper panel) nanoDSF traces showing a negative inflection point for TAPBPR at a $T_m$ of 52.5° C., and a positive inflection point for TAX/HLA-A*02:01 at a $T_m$ of 66.5° C. (lower panel) nanoDSF traces of HLA-A*02:01/TAPBPR loaded with different peptides from our library showing a consistent negative inflection point corresponding to the TAPBPR $T_m$, and a positive inflection point corresponding to the $T_m$ values of different pMHC molecules. (c) Correlation between $T_m$ values of different pHLA-A*02:01 molecules, measured by DSF, and $EC_{50}$ values of peptide binding on empty HLA-A*02:01/TAPBPR complexes, measured by Bio-Layer Interferometry (FIG. 2g). $EC_{50}$ error bars were estimated from 3 independent experiments per peptide. (d) Correlation between $T_m$ values of pMHC molecules prepared using photo-exchange and TAPBPR-mediated peptide exchange. (e) Correlation between $T_m$ values of TAPBPR exchanged pMHC molecules measured by conventional DSF as shown in (a), and by nanoDSF (b).

Recovery of MART-1 tetramer barcodes on DMF5+ cells from PBMC-DC co-cultures spiked with 1% DMF5 cells. Number of MART-1 tetramer counts and number of DMF5 counts (both plotted on the y-axis) per cell analyzed (x-axis), where n=256. Cells are ordered based on DMF5 read counts. Bar graph displays the mean MART-1 tetramer reads from DMF5+(>10 DMF5 reads n=76) and DMF5-(≤10 DMF5 reads, n=927) cells. Error bars indicate 1 standard deviation from the mean. (b) Distribution of antigen specificities identified from tetramer+/CD8+ T-cells from human splenocytes and the number of tetramer-barcode read per cell. Each dot represents a single cell, n=102 in total. (c) V(D)J usage of cells identified as specific for the EBV-BRLF1 antigen (YVLDHLIVV) (SEQ ID NO:68). All TRAVJ (n=11) and TRBVJ (n=14) chains identified are represented. TCR alpha chains identified for EBV-BRLF1 specific T-cells. Repeated BRLF-1 TRA chains are highlighted in orange. Gating strategies used for sorting tetramer+ cells are outlined in FIG. 21.

Figures 20A, 20B, 20C:
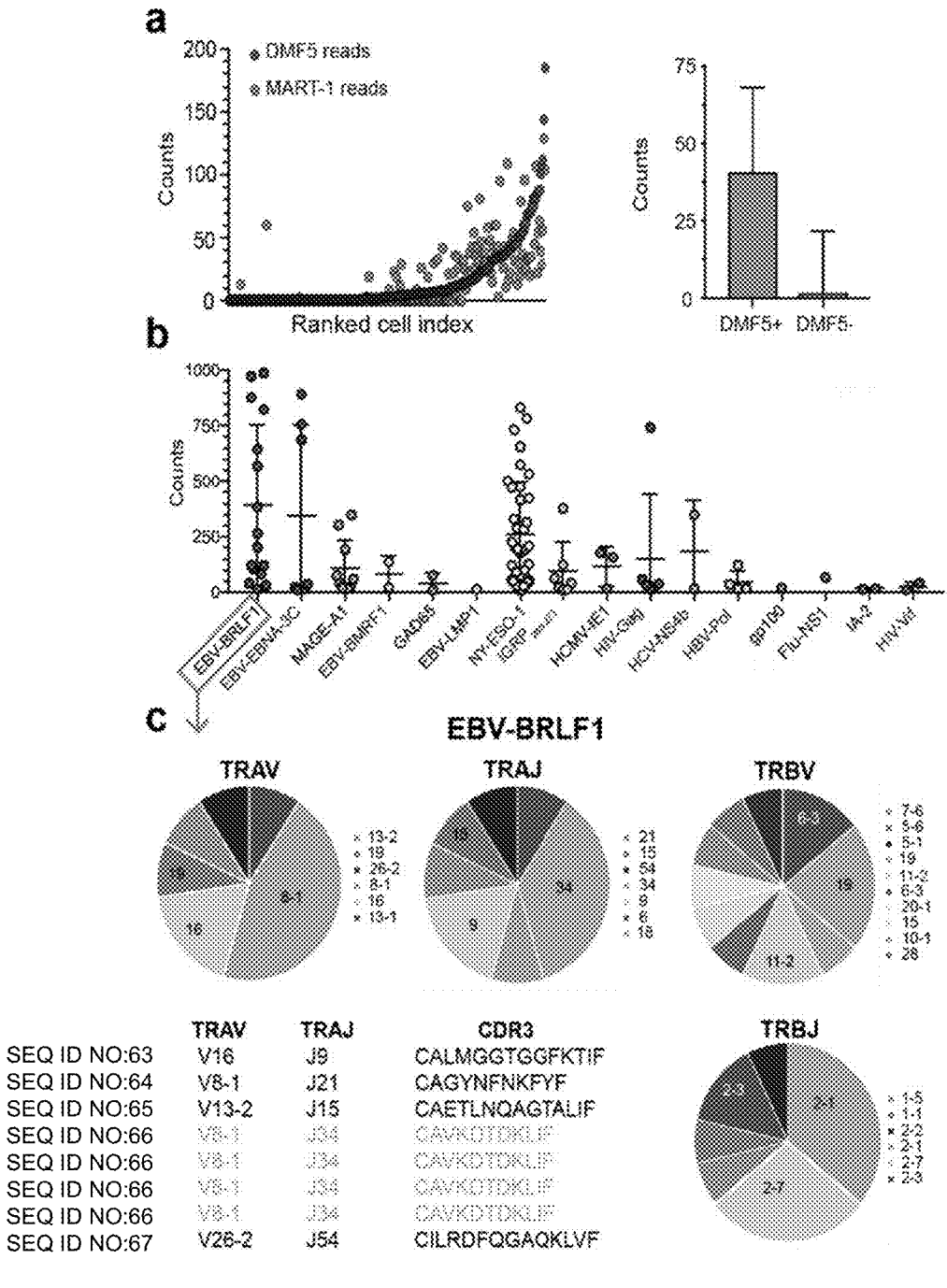
FIG. 20A-FIG. 20C are graphs showing the identification of paired αβ TCR sequences with their pHLA-A*02:01 antigen specificities from polyclonal T-cell samples. (a)
Figures 21A, 21B:
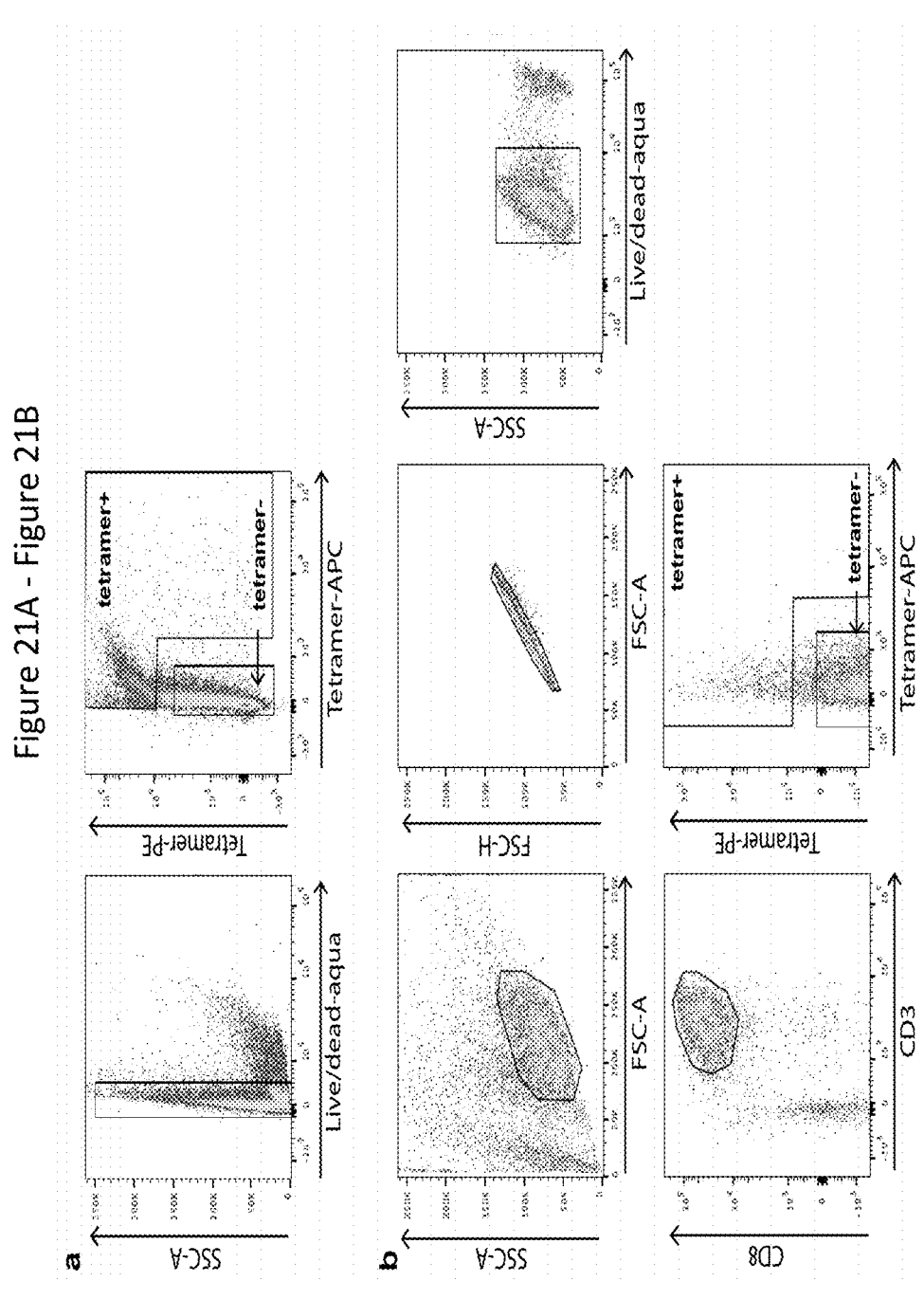

FIG. 21A-FIG. 21B are graphs depicting gating strategies used for sorting tetramer+ cells in FIG. 20. (a) Gating strategy used to sort tetramer positive cells expanded in vitro with NB epitope pulsed DCs. Mixed cell cultures of pulsed DCs and PBMCs were stained using both PE/APC versions of tetramer library 1, and sorted on a flow cytometer by gating on live cells, then on tetramer positive cells. (b) Gating strategy used to sort CD8- enriched splenocytes stained with PE/APC versions of library 2 . Cells were sorted by SSC-A and FSC-A to select for lymphocytes, then filtered for single cells using FSC-H and then live cells with LIVE/DEAD-Aqua. From this, CD8+ T-cells were gated based on CD8 and CD3 staining and then tetramer positive cells were collected for sequencing experiments. Due to low observed staining on the APC fluorophore channel for both samples shown in (a,b)>99% of collected cells correspond to the PE-tetramer positive fractions.

DETAILED DESCRIPTION

A. Overview

High-throughput screening strategies using large arrays of peptide-MHC class I multimers can allow for the large scale identification of antigen specific T cells and/or antigens that bind to particular MHC class Is (e.g., tumor antigens). Identification of such antigen specific T cells and/or antigens can in turn lead to the understanding of the pathogenesis of particular diseases, as well as the development of novel therapies.

Such high-throughput screens, however, are limited by the ability to produce large collections of peptide-MHC class I multimers. The instability of peptide deficient MHC class I molecules, for example, makes large scale production of peptide-MHC class I multimers using such MHC class I molecules difficult. While conditional ligands have been used for large scale production of peptide-MHC class I multimers, such conditional ligands are limited due to sample aggregation, precipitation during the photolysis/peptide exchange step, and, in some cases, instability of the conditional ligand leading to high background levels of exchange. As such, there remains a need for new methods of making peptide-MHC class I multimer complex libraries.

Provided herein are stable peptide deficient MHC class I/chaperone compositions and methods of making such compositions. Such peptide deficient MHC class I/chaperone complexes can be used for production of large collections of peptide-MHC class I multimer complexes (e.g., up to 10,000 different specificities), which can then in turn be used in high throughput screens for immune profiling towards disease diagnosis and for the development of new therapies. The peptide deficient MHC class I/chaperone complexes provided herein are advantageously stable and can be stored for long periods of time prior to their use in making peptide-MHC class I multimer complexes.

B. Peptide Deficient-MHC Class I/Chaperone Complexes

In one aspect, provided herein is a composition that includes a purified peptide deficient-MHC class I/chaperone complex, wherein the purified complex includes a peptide deficient MHC class I and a chaperone. Such purified peptide deficient-MHC class I/chaperone complexes are advantageously stable and can be stored for long periods of time in solution prior to use, for example, in making peptide-MHC class I multimer complexes, as described herein.

As used herein, an "MHC class I," "Major Histocompatibility Complex class I," "MHC-I" and the like all refer to a member of one of two primary classes of major histocompatibility complex (MHC) molecules (the other being MHC class II) that are found on the cell surface of all nucleated cells in the bodies of jawed vertebrates. MHC class I molecules function to display peptide fragments of antigen to cytotoxic T cells, resulting in an immediate response from the immune system against a particular antigen displayed with the help of an MHC class I molecule.

MHC class I molecules are heterodimers that consist of two polypeptide chains, α (heavy chain) and β2-microglobulin (light chain). The two chains are linked noncovalently via interaction of light chain and the α3 domain of the heavy chain and floor of the α1/α2 domain. Only the heavy chain is polymorphic and encoded by a HLA gene, while the light chain is species-invariant and encoded by the Beta-2 microglobulin gene. The α3 domain is plasma membrane-spanning and interacts with the CD8 co-receptor of T-cells. The α3-CD8 interaction holds the MHC I molecule in place while the T cell receptor (TCR) on the surface of the cytotoxic T cell binds its syngeneic MHC-I ligand (or matched, in the sense that both the TCR and MHC-I are encoded in the same germline), and checks the coupled peptide for antigenicity. The α1 and α2 domains of the heavy chain fold to make up a groove for peptides to bind. MHC class I molecules bind peptides that, in most cases, are 8-10 amino acid in length.

In mice, MHC class I is called the "H-2 complex" or "H-2" and include the H-2D, H-2K and H-2L subclasses. In humans, MHC class I molecules include the highly polymorphic human leukocyte antigens HLA-A, HLA-B, HLA-C and the less polymorphic HLA-E, HLA-F, HLA-G, HLA-K and HLA-L. Each human leukocyte antigen (e.g., HLA-A) includes multiple alleles. For example, HLA-A includes over 2430 known alleles. In some embodiments, the purified peptide deficient-MHC class I/chaperone complex includes an HLA-A. In certain embodiments, the purified peptide deficient MHC class I/chaperone complex includes an HLA-B. In other embodiments, the purified peptide deficient MHC class I/chaperone complex includes an HLA-C. In an exemplary embodiment, the purified peptide deficient MHC class I/chaperone complex includes an HLA-A01 or HLA-A02 allele. In other embodiments, the peptide deficient-MHC class I/chaperone complex includes a mouse H-2. In certain embodiments, the H-2 is an H-2D, H-2K or H-2L. In exemplary embodiments, the H-2 is H-2D$^d$ or H-2L$^D$.

The purified peptide deficient-MHC class I/chaperone complex described herein further includes a chaperone. The chaperone can be any chaperone. In some embodiments, the chaperone is Tapasin Binding Protein Related (TAPBPR). In an exemplary embodiment, the peptide deficient-MHC class I/chaperone complex includes a TAPBPR chaperone and an HLA-A MHC class-I molecule. In some embodiments, the HLA-A is HLA-A01 or HLA-A02.

Peptide deficient-MHC class I/chaperone complexes are advantageously highly stable and soluble. In some embodiments, the peptide deficient-MHC class I/chaperone complexes can be stored at concentrations of up to 50, 100, 150, 200, 250, 300, 350, 400, 500 µM, or 1 mM in solution without precipitation at 4° C. In certain embodiments, the peptide deficient-MHC class I/chaperone complexes are completely soluble and remain peptide receptive in solution at a concentration of up to 1 mM at 4° C. for up to 1 month, 2 months, 3 months, 4 months, 5 months, 6 months, 7 months, 8 months, 9 months, 10 months, 11 months, or a year. The stability of subject peptide MHC class I complexes (e.g., peptide deficient-MHC class I/chaperone complexes) can be measured, for example, using differential scanning fluorimetry techniques. in certain embodiments, the peptide deficient-MHC class I/chaperone complexes are stored at −80° C. In particular, embodiments, the peptide deficient-MHC class I/chaperone complexes are lyophilized.

In another aspect, provided herein is a method of making the subject purified peptide deficient-MHC class I/chaperone complex. To make such complexes, an MHC class I heavy chain, an MHC class I light chain and a placeholder peptide are first incubated under conditions wherein the MHC class I heavy chain, the MHC class I light chain and the placeholder peptide form a placeholder peptide-MHC class I (p*MHC-I) complex. The placeholder peptide-MHC class I (p*MHC-I) complex is then contacted with a dipeptide and chaperone. Without being bound by any particular theory of operation, it is believed that the dipeptide alters the placeholder peptide conformation in the groove of the MHC class I in a manner that allows the chaperone (e.g., TAPBPR) to completely remove the placeholder peptide from the groove. The chaperone then remains bound to the MHC class I, thereby maintaining the MHC class I in a stable conformation that is receptive to new peptides.

In the first step of making the placeholder peptide-MHC class I (p*MHC-I) complex, MHC class I heavy chains, MHC class I light chains and placeholder peptides are incubated under conditions wherein the MHC class I heavy chain, the MHC class I light chain and the placeholder peptide refold to form a placeholder peptide-MHC class I (p*MHC-I) complex. MHC class I heavy chains and light chains can be obtained using any method known to one of skill in the art. For example, nucleic acids encoding known MHC class I heavy chains and light chains can be integrated into one or more expression vectors, that are in turn transformed into a suitable host for expression (e.g., E. coli). MHC class I heavy chains and light chains produced by such host cells can then be isolated and purified for use with the subject methods.

In some embodiments, the heavy chain, light chain and placeholder peptide are incubated in a refolding buffer that favors the formation of the p*MHC-I complex. In an exemplary embodiment, the refolding buffer includes arginine-HCl, EDTA, reduced oxidized L-glutathione, and Tris base. The heavy chain and light chain can be present at any ratio that favors the formation of the p*MHC-I complex. In certain embodiments, the MHC class I heavy chains and light chains are incubated at a 1:1, 1:2, 1:3, 1:4, 1:5 ratio of heavy chain to light chain. In an exemplary embodiment, the MHC class I heavy chains and light chains are incubated at a ratio of 1:3 in the presence of the placeholder polypeptide. The MHC class I heavy chain and light chains can be incubated with the placeholder peptide in the refolding buffer for at least 12 hours, 18 hours, 24 hours, 2 days, 3 days, 4 days, 5 days, 6 days or a week to obtain properly folded p*MHC-I complexes. In some embodiments, the MHC class I heavy chain, light chain and placeholder peptides are incubated for 1 to 4 days. In certain embodiments, this first step is carried out at approximately 3° C. to 10° C. In an exemplary embodiment, the refolding of the MHC class I heavy chain and light chains with the placeholder peptide is carried out at 4° C.

Suitable placeholder peptides that can be used in this first step include, for example, modified versions of peptides known to bind to the particular MHC class I allele included in the peptide deficient-MHC class I/chaperone complex. Such placeholder polypeptides have been modified to have a lower binding affinity to the particular MHC class I molecule compared to the known polypeptide. Peptides known to bind various MHC-class Is can be found, for example, at the MHCBN database. In some embodiments, the placeholder polypeptide is a N-terminal truncated version of a known polypeptide that binds to the MHC class I of interest (e.g., an HLA-A02). For example, a known peptide that binds to HLA-A02 is the HTLV-1 epitope $TAX_{11-19}$, having the amino acid sequence LLFGYPVYV (SEQ ID NO:7). As such, a suitable placeholder peptide that can be used in making subject peptide deficient-MHC class I/chaperone complexes has the amino acid sequence LFGYPVYV (SEQ ID NO:3). In some embodiments, wherein the MHC class I is HLA-A02 (e.g., HLA-A*02:01), the placeholder peptide is one of the following sequences: LFGYPVYV (SEQ ID NO:3) (gTAX), Ac-LLFGYPVYV (SEQ ID NO:4) (N-terminally acetylated TAX), or ULFGYPVYV (SEQ ID NO:8) (first residue is a D-leucine). In some embodiments, where the MHC class I is mouse $H-2D^d$, the placeholder peptide has the sequence GPGRAFVTI (SEQ ID NO:1).(gP18-I10). In certain embodiments, where the MHC class I is mouse $H-2L^d$, the placeholder peptide is QLSPFPFDL (SEQ ID NO:2) (QL9).

Placeholder peptides are typically at least 8 amino acids long. In some embodiments, the placeholder polypeptide is at least 8, 9, 10, 11, 12 or 13 amino acids long. In particular embodiments, the polypeptide is 8, 9, 10, 11, 12 or 13 amino acids long.

In the second step, the p*MHC-I complex is incubated in the presence of a dipeptide and chaperone. In the presence of the dipeptide and chaperone, the placeholder peptide is displaced from the MHC class I and the chaperone binds the MHC class I to form the peptide deficient-MHC class I/chaperone complex. As discussed above, the peptide deficient-MHC class I/chaperone complex is stable and can be stored for long periods of time prior to loading with one or more peptides of interest and formation of multimers (e.g., tetramers).

In some embodiments, the chaperone is a Tapasin Binding Protein Related (TAPBPR). TAPBPR protein includes a signal sequence, three extracellular domains comprising a unique membrane distal domain, an IgSF (immunoglobulin superfamily) V domain and an IgC1 domain, a transmembrane domain, and a cytoplasmic region. See, e.g., Boyle et al., PNAS 110 (9) 3465-3470 (2013). TAPBPR can be made by any method known in the art, including those described in Morozov et al., , which is incorporated by reference herein, particularly for its teaching of methods of making TAPBR chaperones. In certain embodiments, the chaperone is Tapasin. In some embodiments, the chaperone (e.g., TAPBR) is incubated with the p*MHC-I complex and dipeptide at ratio of 1:1 chaperone to p*MHC-I complex. In an exemplary embodiment, the dipeptide is glycyl-methionine or glycyl-phenylalanine.

The incubation of the p*MHC-I, chaperone and dipeptide can be done for at least 1 hour, 2 hours, 3 hours, 4 hours, 5 hours and 6 hours. Following incubation, the resulting peptide deficient-MHC class I/chaperone complexes can be isolated by size exclusion chromatography (SEC) and confirmed using any technique known in the art, including, for example, liquid chromatography-mass spectrometry techniques.

In some embodiments, the MHC class I of the p*MHC-I is an HLA-A. In an exemplary embodiment, the HLA-A is HLA-A01 or HLA-A02. In other embodiments, the MHC class I of the p*MHC-I is an H-2. In exemplary embodiments, the H-2 is $H-2D^d$ or $H-2L^d$.

In some embodiments, the MHC class I is a variant MHC class I that includes one or more mutations that reduces MHC class I binding affinity for TAPBR chaperone. Such a mutation advantageously facilitates subsequent peptide loading and/or peptide-MHC class I multimer complex production as described below. In some embodiments, the variant MHC class I includes one or more mutations in the α3 domain of the heavy chain that reduces MHC class I binding affinity for TAPBR chaperone. In certain embodiments, the H-2 is a variant $H-2D^d$ or $H-2L^d$ that includes an amino acid substitution at M228 in the α3 domain of the heavy chain. In particular embodiments, the M228 substitution is a M228N, M228Q, M228S, M228T or M228Y substitution. In some embodiments, the MHC class I is a variant HLA-A01 (e.g., HLA-A*01:01) that includes a T228M mutation in in the α3 domain.

In certain embodiments, the MHC-I of the peptide deficient MHC-I/chaperone complex is biotinylated. In an exemplary embodiment, the MHC-I is biotinylated using a C-terminal BirA tag with any method known to one of skill in the art. In an exemplary embodiment, the biotinylation occurs after the purification of the p*MHC-I complex. Biotinylation of pMHC-I monomers allows for the attachment of such monomers to backbones (e.g., streptavidin or dextran) to form multimers (e.g., pMHC-I tetramers) that can be used in various methods described herein.

C. Peptide-MHC Class I Complexes

The purified peptide deficient-MHC class I/chaperone can be subsequently loaded with a peptide of interest. In this step, the purified peptide deficient-MHC class I/chaperone is incubated in the presence of the peptide of interest. Without being bound by any particular theory of operation, it is believed that when present in molar excess of the peptide deficient-MHC class I/chaperone, the peptide of interest is loaded onto the MHC class I and the chaperone is released, thereby forming a peptide-MHC class I complex that includes the peptide of interest (pMHC-I). The resulting peptide-MHC class I (pMHC-I)complexes can further be used to form multimers, for example, tetramers. Uses for such multimers (e.g., the identification of antigen specific T cells) are further described herein.

In some embodiments, the peptide of interest is incubated at a molar excess of at least 2, 5, 10, 15, 20, 25, 30, 35, 40, 45, 50, 75 or 100 times to the peptide deficient-MHC class I/chaperone complex. In an exemplary embodiment, the peptide of interest is incubated at a molar excess of 50 times to the peptide deficient-MHC class I/chaperone complex. Such incubations can be carried out at room temperature for at least 30 minutes, 1 hour, 2 hours, 5, hours, 10 hours, 15 hours, 20 hours or a day.

Peptides of interest are typically 8 to 13 amino acids in length. In some embodiments, the peptide of interest is an antigen. In an exemplary embodiment, the peptide of interest is a tumor antigen. Tumor antigen peptides in the context of the MHC class I and multimer complexes described herein can be useful, for example, in the identification of T cells reactive to the antigen of interest.

Purification of the formed peptide-MHC class I (pMHC-I) complexes from the released chaperone can be carried out using size exclusion chromatography (SEC). The newly formed pMHC-I can be confirmed using any technique known in the art, including, for example, liquid chromatography-mass spectrometry techniques.

In some embodiments, the MHC class I of the peptide-MHC class I complexes is an HLA-A. In an exemplary embodiment, the HLA-A is HLA-A01 or HLA-A02. In one embodiment, the pMHC-I is biotinylated. In other embodiments, the MHC class I of the peptide-MHC class I complexes is a mouse H-2. In exemplary embodiments, the H-2 is H-2D$^d$ or H-2L$^d$. In certain embodiments, the H-2 is a variant H-2D$^d$ or H-2L$^d$ that includes an amino acid substitution at M228 in the α3 domain of the heavy chain. In particular embodiments, the M228 substitution is a M228N, M228Q, M228S, M228T or M228Y substitution. In some embodiments, the MHC class I is a variant HLA-A01 (HLA-A*01:01) that includes a T228M mutation in the α3 domain. Such a mutation advantageously reduces MHC-class I binding affinity for TAPBR chaperone, thereby facilitating subsequent peptide loading and/or peptide-MHC class I multimer complex production as described below.

D. Peptide-MHC Class I Multimer Complexes

Peptide-MHC class I (pMHC-I) complexes made using the subject methods described herein can undergo further multimerization to form multimers that include two or more of the pMHC-Is (i.e., pMHC-I multimers.) In certain embodiments, the multimers include 2, 3, 4, 5, 6, 7, 8, 9 or 10 pMHC-I molecules.

In some embodiments, pMHC-I multimers can be produced by attachment of biotinylated pMHC class I to a backbone (e.g., a streptavidin, avidin or dextran backbone), thereby forming a pMHC-I multimer. In an exemplary embodiment, the biotinylation occurs following the purification of p*MHC-I monomers and prior to the formation of peptide deficient-MHC class I/chaperone complexes. In some embodiments wherein large scale production of pMHC-I multimer libraries is desired, aliquots of the peptide deficient-MHC class I/chaperone complexes are incubated with various peptides of interest and allowed to undergo peptide loading. The resulting pMHC-class I complexes are then multimerized in the presence of a suitable backbone to form pMHC-class I multimers (e.g., tetramers). In some embodiments, the backbone is a streptavidin backbone. In certain embodiments, the backbone is an avidin backbone. In other embodiments, the backbone is a dextran backbone.

In exemplary embodiments, peptide deficient MHC class I/chaperone complexes are biotinylated and then attached to a backbone (e.g., a streptavidin, avidin or dextran backbone), thereby forming peptide deficient MHC class I/chaperone multimers (e.g., tetramers). Such peptide deficient MHC class I/chaperone multimers can be used for the large scale production of pMHC-I multimers comprising one or more peptides of interest by contacting the peptide deficient MHC class I/chaperone multimers with the one or more peptides of interest. For example, in one embodiment, aliquots of the peptide deficient MHC class I/chaperone multimers are contacted with different peptides of interest, thereby forming a library of pMHC-I multimers. After loading of the pMHC-I multimers with peptides of interest, the resulting loaded pMHC-I multimers can be washed to remove any free chaperones, labels (e.g., nucleic acid barcodes) or peptides of interest. Following such a washing step, the exchanged pMHC-I multimers can be stored (e.g., 4° C. for several weeks) or used immediately. In some embodiments, the free chaperones, labels and/or peptides of interest are removed by spin column dialysis.

In some embodiments, the pMHC-I multimer is a dimer. In some embodiments, the pMHC-I multimer is a trimer. In preferred embodiments, the pMHC-I multimer is a tetramer. In one embodiment, the multimer is a dextramer. Dextramers include ten pMHC-I complexes attached to a dextran backbone. Dextramers allow for the detection, isolation, and quantification of antigen specific T-cell populations due to an improved signal-to-noise ratio not present in prior generations of multimers. See, e.g., Bakker and Schumacher, *Current Opinion in Immunology* 17(4): 428-433 (2005); and Davis et al., *Nature Reviews Immunology* 11:551-558 (2011).

In some embodiments, the backbone is conjugated with a detectable label (e.g., a fluorophore or a radiolabel) that allow the multimer to be detected in various applications. In certain embodiments, the detectable label is as fluorophore. See, e.g., Nepom et al., *J Immunol* 188 (6) 2477-2482 (2012). In one embodiment, the detectable label is a radiolabel. In certain embodiments, the backbone includes a barcode (e.g., a nucleic acid barcode) that allows the MHC class I multimer to be used in large scale high throughput processes. See, e.g., Bentzen et al., *Nature Biotechnology* 34(1): 1037-1045 (2016). In an exemplary embodiment, unique barcodes are used for each of the different peptides of interest included in the pMHC-I multimers, thereby allowing for the tracking, sorting and identification of particular pMHC-I multimers in high throughput applications. In particular embodiments, each barcode includes a unique nucleotide sequence.

In some embodiments, the pMHC-I multimer complex is coupled to a toxin (e.g., saporin). Such pMHC-I multimer conjugates can be used to modulate or deplete specific T cell populations. See, e.g., Maile et al., *J. Immunol.* 167: 3708-3714 (2001); and Yuan et al., *Blood* 104: 2397-2402 (2004).

E. Peptide-MHC Class I Multimer Libraries

The methods provided herein allow for the large scale production of stable peptide deficient-MHC-I/chaperone complexes that can in turn be used to produce pMHC-I multimer libraries that include a plurality different peptides of interest for high throughput applications.

In one aspect provided herein, peptide deficient MHC class I/chaperone multimers (e.g., tetramers) are used to form a peptide-MHC class I (pMHC-I) multimer library that includes pMHC-I multimers having different peptides of interest. Such pMHC-I multimers can be made by contacting aliquots of peptide deficient-MHC class I/chaperone multimers with different peptides of interest. In some embodiments, the peptides of interest are different peptides from an antigen of interest.

In some embodiments, pMHC-Is that include the same peptide of interest are attached to backbones to form pMHC-I multimers and the step is performed for a plurality of pMHC-Is that include a library of different peptides of interest. The resulting pMHC-I multimers (e.g., tetramers) are subsequently pooled to form the pMHC-I multimer library.

In an exemplary embodiment, the peptide-MHC class I (pMHC-I) multimer library includes at least 10, 20, 30, 40, 50, 60, 70, 80, 90, 100, 200, 300, 400, 500, 600, 700, 800, 900, or 1,000 different peptide-MHC class I multimer complexes, wherein each different peptide-MHC class I multimer complex includes a different peptide of interest. In certain embodiments, the peptide of interest is a tumor antigen.

In some embodiments, each of the pMHC-I multimer in the library have the same MHC class I allele. In certain embodiments, the MHC class I is HLA-A. In an exemplary embodiment, the HLA-A is HLA-A01 or HLA-A02. In other embodiments, the pMHC-I multimer in the library include H-2 MHC class I. In exemplary embodiments, the H-2 is H-2D$^d$ or H-2L$^d$. In certain embodiments, the H-2 is a variant H-2D$^d$ or H-2L$^d$ that includes an amino acid substitution at M228 in the α3 domain of the heavy chain. In particular embodiments, the M228 substitution is a M228N, M228Q, M228S, M228T or M228Y substitution. In some embodiments, the MHC class I is a variant HLA-A01 (HLA-A*01:01) that includes a T228M mutation in the α3 domain. Such a mutation advantageously reduces H-2 binding affinity for TAPBR chaperone, thereby facilitating subsequent peptide loading and/or peptide-MHC class I multimer complex production as described below.

In some embodiments, the library includes pMHC-I multimers with different MHC class I alleles. In some embodiments, the library includes pMHC-I tetramers.

In certain embodiments, the pMHC-I multimer library includes over 10, 20, 30, 40, 50, 60, 70, 80, 90, 100, 200, 250, 300, 400, 500, 600, 700, 800, 900, 1,000, $1×10^4$, $1×10^5$, $1×10^6$, $1×10^7$, or $1×10^8$ different peptide-MHC class I (pMHC-I) multimer complexes, wherein each different peptide-MHC class I multimer complex includes a different peptide of interest. In some embodiments, each pMHC-I multimer in the library includes a detectable marker. In some embodiments, each pMHC-I multimer in the library includes a nucleic acid bar code or a fluorophore that is used to identify peptide of interest included in the pMHC-I multimer, wherein each barcode or fluorophore corresponds to a different peptide of interest. In some embodiments, each of the pMHC-I multimer in the library includes the same detectable label.

F. Methods of Use

In certain embodiments, the pMHC-I multimer is a pMHC-I tetramer. MHC class I tetramers provided herein can be used to study pathogen immunity, for the development of vaccines, in the evaluation of antitumor response, in allergy monitoring and desensitization studies, and in autoimmunity. See, e.g., Nepom et al., *J Immunol* 188 (6) 2477-2482 (2012); and Davis et al., *Nature Reviews Immunology* 11:551-558 (2011).

In some embodiments, the pMHC-I multimers are used to characterize T cell (e.g., CD8 T cell) responses to a vaccine, including, but not limited to influenza, yellow fever, tuberculosis, and HIV/SIV vaccines. In an exemplary embodiment, the vaccine is a cancer vaccine. In particular embodiments, the cancer vaccine is melanoma or chronic myeloid leukemia. In such embodiments, a sample (e.g., a blood sample) of a vaccinated patient is contacted with one or more of the subject pMHC-I multimers that include one or more peptide of interests derived from the vaccine to identify and monitor antigen specific T cells that are produced in response to the vaccine.

Peptide-MHC class I multimers provided herein can also be used to isolate and enrich particular antigen specific T cells for therapeutic use. See, e.g., Cobbold et al., *J. Exp. Med.* 202: 379-386 (2006); and Davis et al., *Nature Reviews Immunology* 11:551-558 (2011). In this particular application, patient samples are contacted with sortable pMHC-I multimers that include a peptide antigen of interest and a label that allows for sorting (e.g., a fluorophore or nucleic acid label). Antigen specific T cells that bind the pMHC-I multimer are subsequently isolated and purified, for example, using flow cytometry or similar cell sorting and identification techniques.

In certain embodiments, the peptide-MHC class I multimers provided herein are used for epitope mapping. In this method, a plurality of peptide-MHC class I multimers that include different peptides derived from an antigen of interest (e.g., a tumor antigen) are contacted with a sample from a subject. Antigen specific T cells are detected and the corresponding epitope peptide sequences are identified any technique known in the art, include, for example, flow cytometry and cell sorting techniques. See, e.g., Bentzen et al., *Nat Biotechnol.* 34(10):1037-1045 (2016).

In some embodiments, the peptide-MHC class I multimers provided herein are used to determine a T cell profile of one or more subjects. In such an embodiment, a sample from a subject is contacted with a library of pMHC-I multimers that include a library of peptide of interest and a detectable label. Identification of antigen specific T cells that bind particular peptides of interest presented in the context of the pMHC-I multimers is achieved using the detectable label. The methods described herein allow for the large scale production of pMHC-I multimer libraries that can in turn be used for high throughput T cell profiling.

In another aspect, the pMHC-I multimers are used therapeutically for the targeted elimination of particular antigen specific T cells in a subject. In one embodiment, the pMHC-I multimers are conjugated to a cytotoxic agent or a toxin. When administered to a subject, the pMHC-I multimer conjugates attach to and facilitate the elimination of particular antigen specific T cells.

Peptide-MHC class I multimers used in the methods described herein can be tracked and detected using any suitable techniques including, but not limited to, techniques utilizing detectable labels and nucleic acid barcodes that allow identification of particular peptide-MHC class I multimers. In addition, T cells of interest isolated in such methods can also be identified using similar techniques.

T cells of interest that interact with pMHC-I multimers can be isolated using any suitable technique including, for example, flow cytometry techniques. Isolated T cells and corresponding peptide-MHC class I multimers can then be characterized using any suitable method, for example, the ECCITE-seq method as explained below in conjunction with 10× Genomics CHROMIUM SINGLE CELL IMMUNE PROFILING SOLUTION™ with FEATURE BARCODING™ technology. This method incorporates a cellular barcode into cDNA generated from both tetramer oligos and TCR mRNA, thus the pairing of cellular barcodes can connect TCR sequences and other mRNAs with pMHC-I multimers specificities.

EXAMPLES

High Throughput pMHC-I Multimer Library Production Using Chaperone-Mediated Peptide Exchange.

Peptide-MHC Monomer and Recombinant TAPBPR Expression and Purification

Figures 1A, 1B, 1C, 1D:
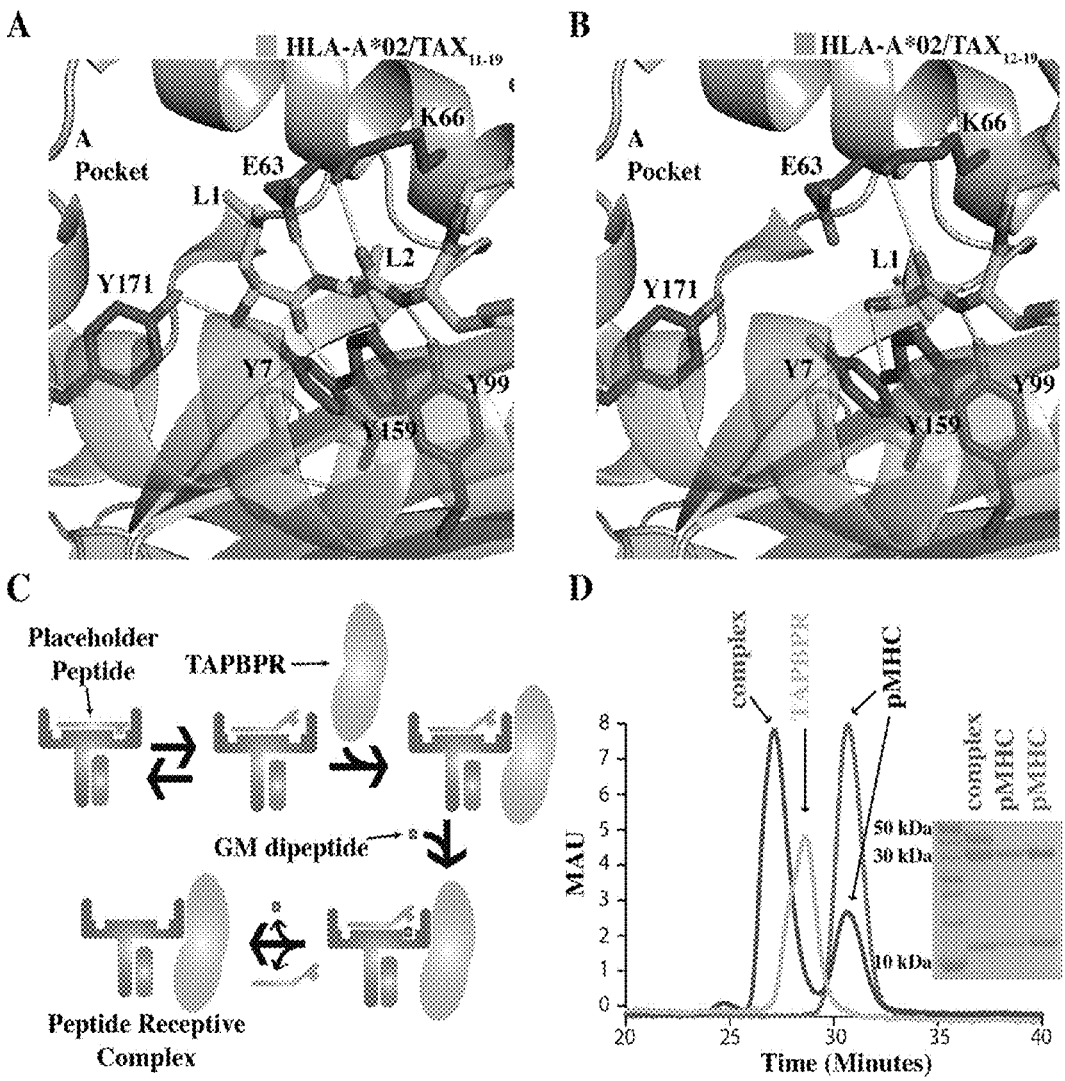
FIG. 1A-FIG. 1D.

Plasmid DNA encoding the luminal domain of class I MHC (MHC-I) heavy chains $H2-D^d$, HLA-A*02:01, and light chain $\beta_2$-microglobulin ($h\beta_2m$,) were provided by the NIH Tetramer Core Facility (Emory University), and transformed into *Escherichia coli* BL21(DE3) (Novagen). MHC-I proteins were expressed in Luria-Broth media, and inclusion bodies (IBs) were purified as described in Garboczi et al., *PNAS* 89(8) 3429-3433 (1992). For in vitro refolding of pMHC-I molecules, 10 mg of synthetic peptides (derived from either the HIV gp160 epitope P18-I10: RGPGRAFVTI (SEQ ID NO:5) for $H2-D^d$, or the HTLV-1 epitope $TAX_{11-19}$: LLFGYPVYV (SEQ ID NO:7) and the Analog Melan-A/MART-$1_{26-35}$(A27L) epitope: ELAGIGILTV for HLA-A*02:01) and a 200 mg mixture of heavy chain:light chain IBs at a 1:3 molar ratio were slowly diluted over 24 hours into refolding buffer (0.4 M Arginine-HCl, 2 mM EDTA, reduced/oxidized L-glutathione 4.9/0.57 mM, 100 mM Tris pH 8.0) at 4° C., while stirring. To obtain suitable pMHC-I molecules for TAPBPR-mediated peptide exchange, we used N-terminally truncated, "placeholder" versions of the P18-I10 or TAX peptides (_GPGRAFVTI (SEQ ID NO:1) and _LFGYPVYV (SEQ ID NO:3), respectively) (FIG. 1A, B). The resulting placeholder peptide/MHC-I complexes are referred to as p*MHC-I herein. For each peptide/MHC I combination, refolding proceeded for four days at 4° C., without stirring. Purification of all pMHC-I complexes was performed by size exclusion chromatography (SEC) using a HILOAD 16/600 SUPERDEX 75 column (150 mM NaCl, 25 mM Tris pH 8), followed by anion exchange chromatography on a mono Q 5/50 GL column at 1 mL/min using a 40 minute 0-100% gradient of buffer A (50 mM NaCl, 25 mM Tris pH 8) and buffer B (1M NaCl, 25 mM Tris pH 8). The luminal domain of TAPBPR was expressed using a stable *Drosophila* S2 cell line, and purified in a similar manner to pMHC-I molecules. All proteins were exhaustively buffer-exchanged into 20 mM $NaH_2PO_4$, pH 7.2, 100 mM NaCl and the presence of the different bound peptides was validated by LC/MS on an LTQ-Orbitrap Velos Pro MS instrument. Typical protein yields from a 1L expression were in the range from 5 to 10 mg, after purification.

Differential Scanning Fluorimetry

Figure 7:
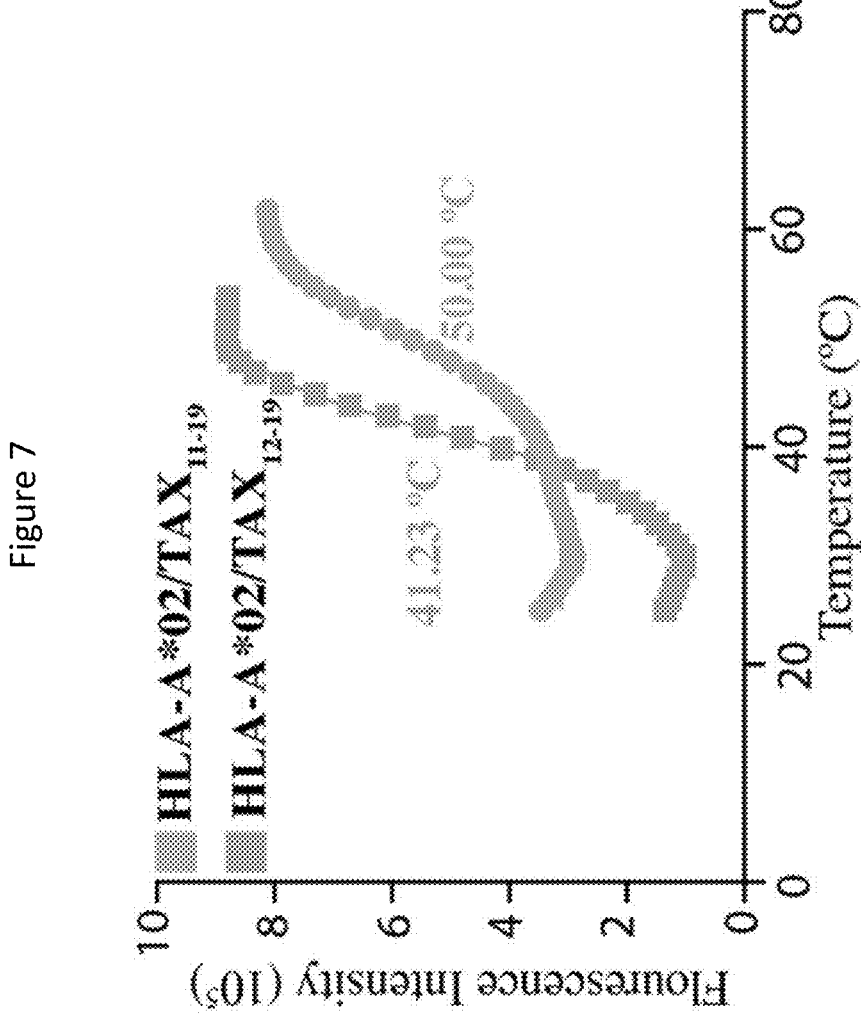
FIG. 7 is a differential scanning fluorimetry showing the stability of $TAX_{12-19}$ bound peptide is lower than that of $TAX_{11-19}$ bound peptide to HLA-A*02:01. Differential Scanning Fluorimetry shows that the TAX-bound MHC-I complex (cyan) has a higher thermal stability (melting temperature, $T_m$ of 50.0° C.), relative to the TAX complex (42.23° C.).

Differential Scanning Fluorimetry, used here as a measure of thermal stability of different pMHC-I molecules (e.g., those that include HIV gp160 epitope P18-I10, HTLV-1 epitope $TAX_{11-19}$ or their placeholder counterparts) was performed using an Applied Biosystems ViiA qPCR machine with excitation and emission wavelengths at 470 nm and 569 nm respectively. 7 μM of each protein sample was mixed with 10× Sypro Orange dye in matched buffers (20 mM $NaH_2PO_4$, pH 7.2, 100 mM NaCl) and loaded in triplicates into MicroAmp Fast 96 well plates at a final volume of 50 μL. The thermal stability was measured by increasing the temperature at a scan rate of 1° C. per minute from 25° C. to 95° C. Data were fit using a boltzmann sigmoidal model on GraphPad Prism (FIG. 7).

Formation of Peptide-Deficient MHC-I/TAPBPR Complexes and Tetramerization

Figures 2A, 2B, 2C:
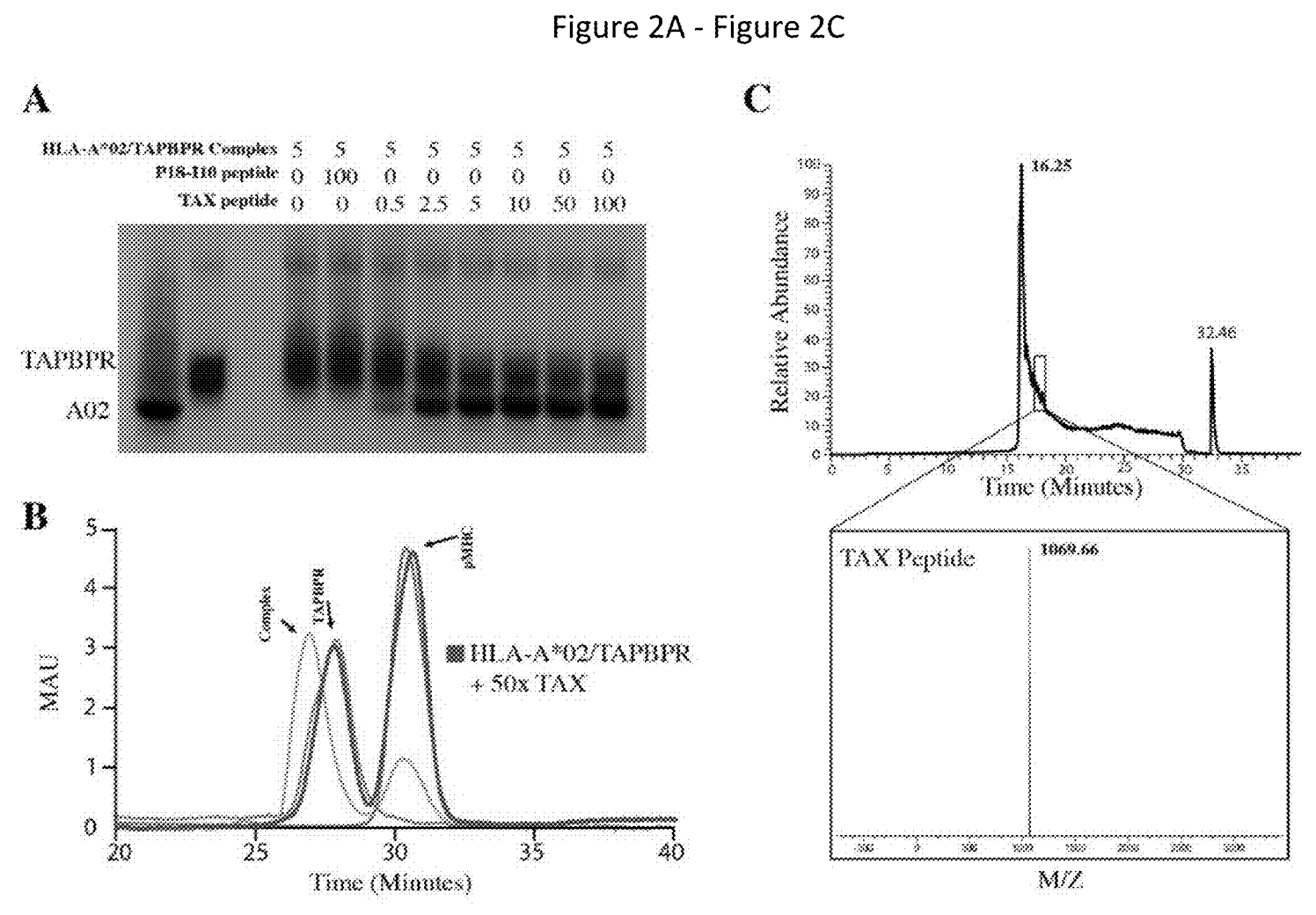
Figures 6A, 6B:
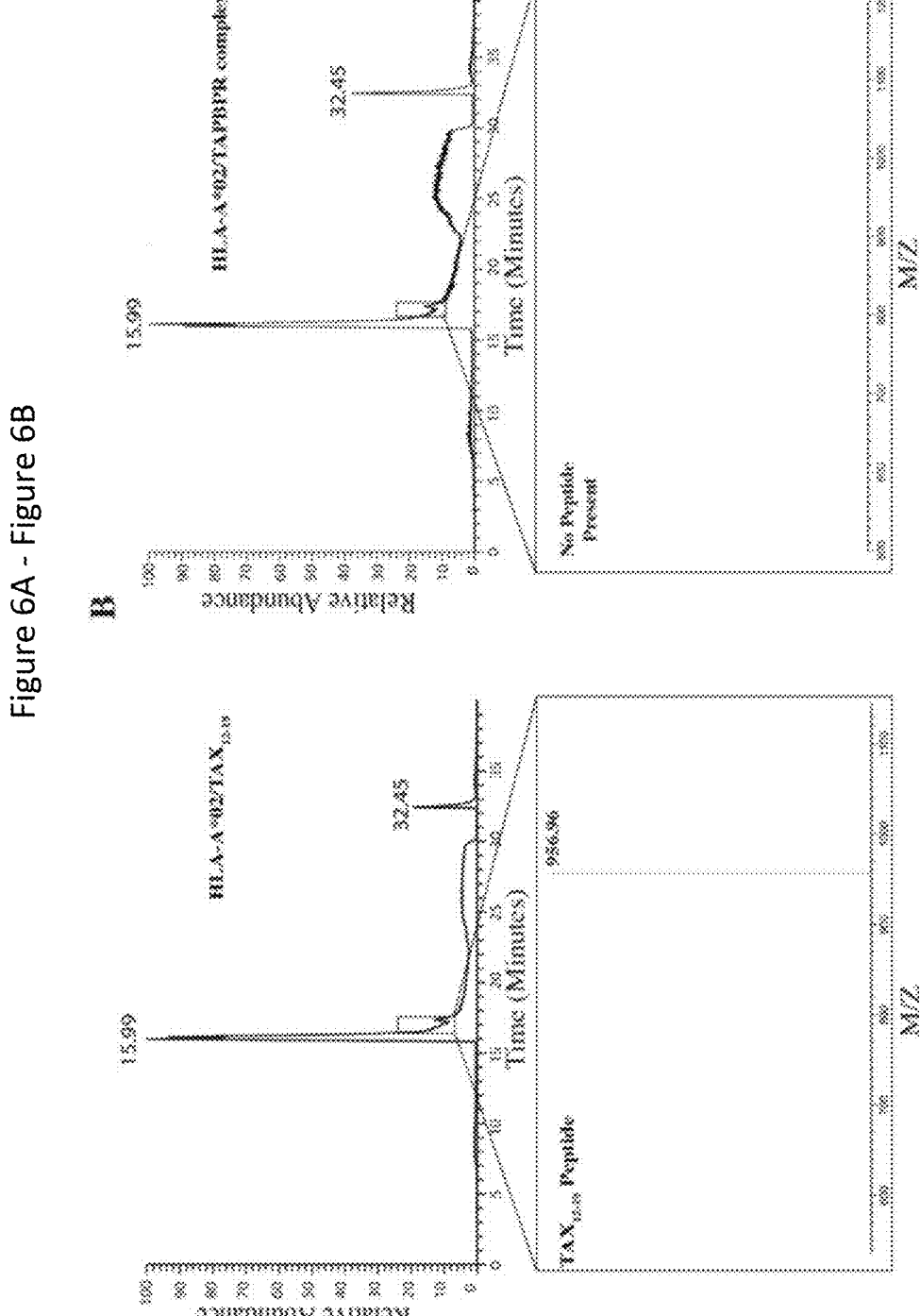
FIG. 6A-FIG. 6B is an LC/MS analysis, confirming peptide deficient HLA-A*02/TAPBPR complex.

Purified, BirA-tagged p*MHC-I molecules (or pMHC-I, used as positive controls) were biotinylated using the Bulk BirA: BirA biotin-protein ligase bulk reaction kit (Avidity), according to manufacturer specifications. Biotinylation was confirmed using a gel shift assay. Following further confirmation by LC/MS, each biotinylated p*MHC-I molecule was incubated for 2 hours at room temperature with a 1:1 molar ratio of TAPBPR in the presence of 10 mM GM dipeptide (FIG. 1C). Following incubation, stoichiometric MHC-I:TAPBPR complexes were purified by Size Exclusion Chromatography (SEC), using a Superdex 200 increase 10/300 column (GE), run at a flow rate of 0.5 mL/min (FIG. 1D). A concentration of 10 mM GM dipeptide was maintained throughout the purification process. SEC elutions were confirmed to contain the expected molecular species by SDS-PAGE electrophoresis, and the resulting MHC-I/TAPBPR complexes were confirmed to be peptide-deficient by LC/MS (FIGS. 6A and B). Peptide deficient MHC-I/TAPBPR complexes are highly stable, soluble, and can be stored for months at 4° C. at up to 1 mM concentrations without any signs of precipitation. Loading of new peptides of interest was achieved by offering the synthetic peptide at 50× molar excess to 50 μg of peptide-deficient MHC-I/TAPBPR complex, and incubated at room temperature for 1 hour. Tetramerization of the exchanged pMHC-I was performed immediately after this step, using a standard protocol. Briefly, 43.5 μL of 1 mg/ml Streptavidin-APC or 79.5 μL of 1 mg/ml Streptavidin-PE (Prozyme) was added in 10 equal aliquots separated by 10 minutes of incubation on ice. Validation of the Peptide-Receptive State of MHC-I/TAPBPR Complexes by Native Gel Electrophoresis and SEC Tandem LC/MS Peptide-deficient MHC-I/TAPBPR complexes were confirmed to be peptide-receptive using a titration of a suitable peptide ($TAX_{11-19}$ or P18-I10, depending on the tetramer), by following the formation of the free pMHC-I species using native gel electrophoresis (FIG. 2A). A 8% Polyacrylamide gel was run for 4.5 hours at a constant 90 V in a buffer of 25 mM TRIS, pH 8.8, and 192 mM Glycine, at 4° C. 5 μM aliquots of peptide-deficient MHC-I/TAPBPR complex, prepared as described previously were diluted with 10% glycerol and mixed with graded concentrations of excess peptide. In addition, the exchanged pMHC-I molecules were further purified from released TAPBPR using SEC (FIG. 2B), and the presence of the new peptide was confirmed by LC-MS (FIG. 2C). The performance of the resulting tetramers, in terms of staining efficiency and specificity, was identical for tetramers prepared using purified pMHC-I molecules relative to pMHC-I+TAPBPR mixtures, therefore this step is not necessary and tetramerization can proceed directly following the peptide exchange reaction.

DNA Barcoding

Figure 5A:
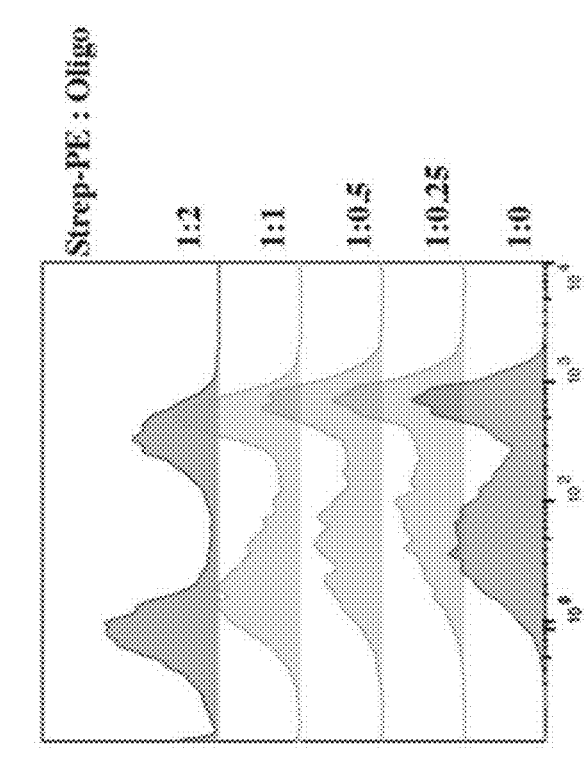
FIG. 5A-FIG. B depicts staining of DMF5+ Jurkat Cells using exemplary DNA oligo MHC-I multimers described herein.
Figure 5B:
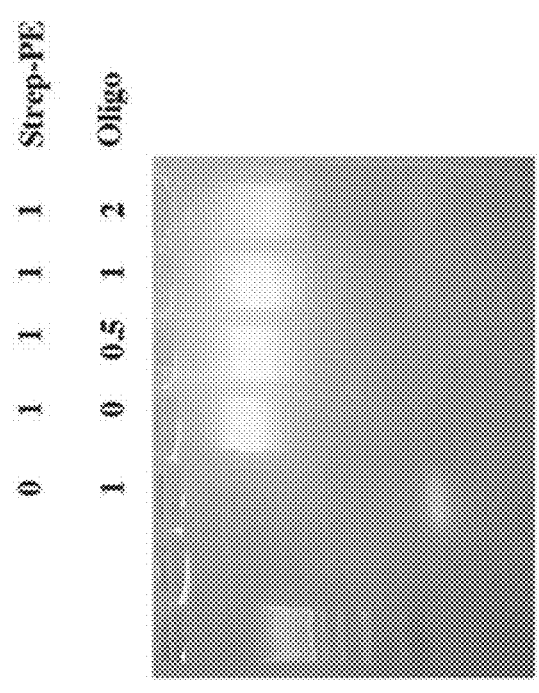
FIG. 5B shows the effect of streptavidin-PE: biotinylated DNA oligo molar ratio used for barcoding on T cell staining profiles of the resulting pMHC-I multimers. For each experiment, $2\times10^5$ cells were stained with 125 ng/mL DNA barcoded Streptavidin-PE pMHC-I multimers. The presence of the DNA oligo in the final, barcoded MHC-I multimers was further confirmed using PCR amplification upon exhaustive dialysis of any excess oligo.

Biotinylated DNA oligos with custom "barcode" sequences (IDT) were diluted to a concentration of 10 μM and added to 1 mg/mL of Streptavidin APC or PE, at 2:1 molar ratio. The addition of oligos are performed in 5 equal aliquots and incubated for 1 hour on ice in the dark. DNA conjugation was confirmed by electrophoresis on a 2% Agarose Gel run for 1 hour at a constant voltage of 90V. Barcoding and peptide exchange for the preparation of DNAoligo-pMHC multimers can be performed in one step. Here, DNA-oligo-bound Streptavidin is added to peptide-receptor MHC-I/TAPBPR complex, in the presence of molar excess of peptide of interest, as outlined in detail in the "Formation of peptide-deficient MHC TAPBPR complex and tetramerization" section above. It was shown that DNA barcoding does not interfere with tetramer staining efficiency or specificity for both pMHC-I systems tested in this study (FIG. 5), consistently with a previous report (Bentzen et al., *Nat Biotechnol.* 34(10):1037-1045 (2016)). Barcoded pMHC-I libraries, prepared in a high-throughput manner using the methods described herein, can be therefore used towards large-scale immune profiling analysis (see, e.g., Reddy, *Nature* 547(7661):36-38 (2017)) and TCR repertoire classification (see, e.g., Han et al., *Nat Biotechnol.* 32(7): 684-692 (2014)) at the single-cell level, by coupling the tetramer barcode readout with established, PCR-based methods for the amplification of V(D)J segments followed by detailed computational analyses (Dash et al., *Nature* 547 (7661): 89-93 (2017)). A similar application using barcoded antibodies (Stoeckius et al., *Nat Methods* (9):865-868 (2017)) was recently described in the context of the CITE-seq approach.

Flow Cytometry

Figure 3:
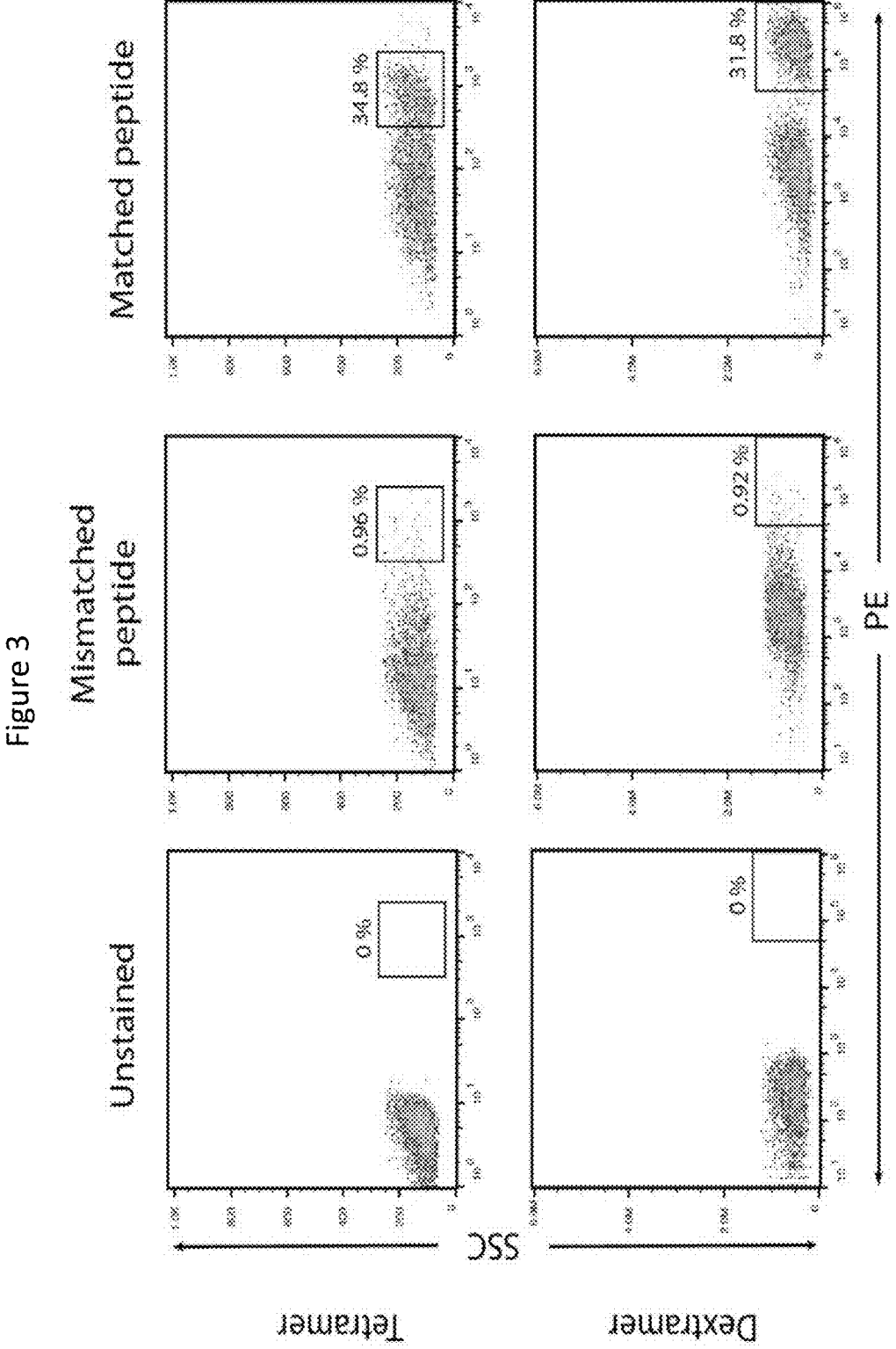
FIG. 3 depicts staining of monoclonal T cell lines using tetramers prepared using the current chaperone-mediated peptide exchange approach, versus commercially available dextramers. A Jurkat T3.5 cell line expressing the engineered DMF5 receptor that recognizes the MART-1 antigen restricted by HLA-A*02:01 is used for all staining experiments. FSC and SSC gates are first applied to isolate living cells from cell debris and dead cells. The left most panels (unstained), middle panels (HLA-A*02:01 tetramers or commercially available dextramers® (IMMUDEX) with mismatched peptide), and right panels (HLA-A*02:01/ MART-1 tetramer or dextramer). Overall, similar staining results are obtained using both multimers.

The efficiency of all resulting pMHC-I tetramers was tested by staining two monoclonal T cell lines, which recognize the P18-I10 (Takahashi et al., *Proc Natl Acad Sci USA* 85(9):3105-9 (1998)) or MART-1 (Kawakami et al., *J Exp Med.* 180(1):347-52 (1994)) epitopes, respectively (FIG. 3). For P18-I10, an immunodominant epitope derived from the HIV gp160 envelope protein and restricted by the murine MHC-I molecule H2-D$^d$, we used the cell line 58α$^{--}$β$^{--}$ (Letournour et al., *Eur J Immunol.* 19(12): 2269-74 (1989)), a variant of the DO11.10.7 mouse T-cell hybridoma lacking a functional endogenous TCR, and which has been subsequently transformed with the B4.2.3 TCR (Natarajan et al., *Nat Commun.* 8:15260 (2017)) α and β chain sequences joined by a 2A linker sequence (Dr. Kannan Natarajan, NIH). A similar TCR β chain-deficient T3.5 Jurkat cell line (Ohashi et al., *Nature* 316(6029):606-9 (1985)) carrying a transgene encoding an engineered version of the DMF5 T cell receptor, which recognizes the HLA-A*02:01-restricted Melan-A/MART-1 melanocytic differentiation antigen, was obtained from Dr. Mark Yarmarkovich (Children's Hospital of Philadelphia). In accordance with the original report (Altman et al., *Science* 274(5284):94-6 (1996)) for the use of MHC-I tetramers, both monoclonal T cell lines were confirmed to be specific for their corresponding epitopes using a peptide stimulation assay (Natarajan et al., *Nat Commun.* 8:15260 (2017)), followed by measurements of secreted IL-2 levels by ELISA (BD-Pharmingen). Lack of recognition of the "placeholder" peptides by the T cell lines was shown by staining with tetramers prepared using purified p*MHC-I molecules, and further confirmed in T cell stimulation assays. As an additional negative control, we used a tetramer prepared via loading of an unrelated peptide to peptide-deficient MHC-I, that is not recognized by the DMF5 T3.5 Jurkat cell clone (FIG. 3, middle). The efficiency of multimer staying, in terms of recognized T cell populations and specificity relative to the negative controls, was found to be very similar between the pMHC-I tetramers prepared here and commercially available dextramers (IM-MUDEX), used as a positive control (FIG. 3, right).

Figure 4:
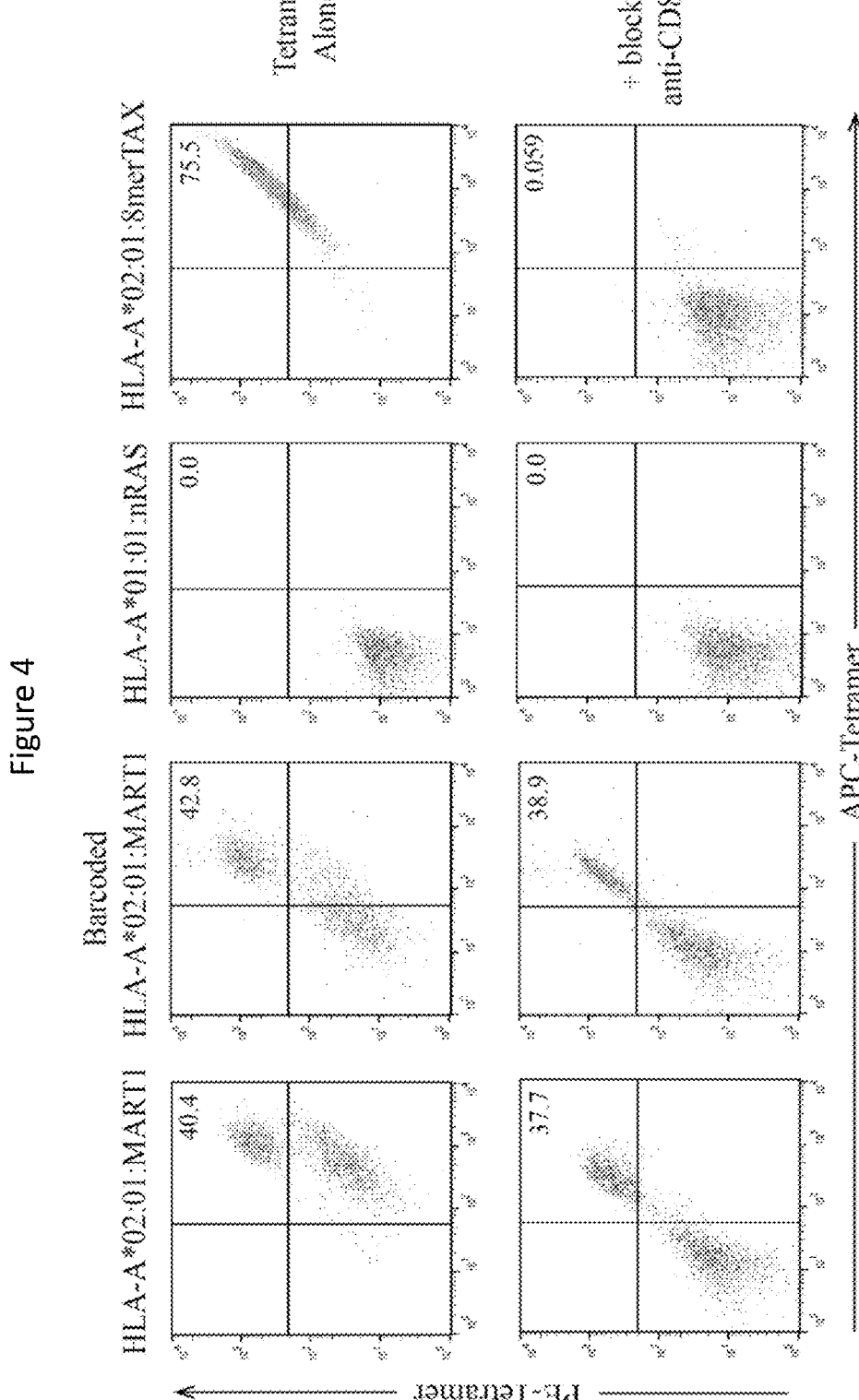
FIG. 4 depicts a study showing that co-staining with an anti-CD8 monoclonal antibody (mAb) enhances tetramer specificity. DMF5+ Jurkat T cells were stained with tetramers prepared using our peptide exchange approach. Plots are gated on live cells as determined by forward and side scatter profiles. Staining is performed in the absence (upper panels) or presence (lower panels) of CD8 blocking mAb. Comparison of staining using different tetramers: HLA-A*02: 01:MART-1, without or with DNA oligo barcodes, respectively (first two columns from the left), HLA-A*02:01 with the placeholder peptide $TAX_{12-19}$ prior to exchange (third column) or a HLA-mismatched tetramer HLA-A*01:01: nRAS (right column), used here as a negative control to account for non-specific staining via tetramer interactions with the CD8 co-receptor. Numbers in the plots indicate the percentage of live cells within the gate or quadrant.

In each experiment (FIG. 3), $2 \times 10^5$ cells were stained with 125 ng/mL PE-labelled pMHC-I tetramer and 75 ng/mL APC-labelled tetramer for 1 hr at 4° C., followed by two washes with 1 mL of FACS buffer (PBS, 2% FBS, 2 mM EDTA), resuspension in 0.5 mL FACS buffer. As an additional control to prevent non-specific binding of tetramers via the CD8 co-receptor, we can further stain using an anti-CD8a-FITC mAb (mouse or human), simultaneously with the pMHC-I multimers (FIG. 4). All flow cytometric analysis was performed using a BD LSR II instrument (BD Biosciences). Live cells were gated based on forward and side scatter profiles and data was analysed using FlowJo software (Tree Star).

Additional Placeholder Peptides

Peptide exchange technologies are essential for the generation of pMHC-multimer libraries, used to probe highly diverse, polyclonal TCR repertoires. Using the molecular chaperone TAPBPR, a robust method for the capture of stable, empty MHC-I molecules has been developed that can be readily tetramerized and loaded with peptides of choice in a high-throughput manner. Combined with tetramer barcoding using multi-modal cellular indexing technology (ECCITE-seq), our approach allows a combined analysis of TCR repertoires and other T-cell transcription profiles, together with their cognate pMHC-I specificities, in a single experiment.

T-cells recognize foreign or aberrant antigens presented by MHC-I expressing cells through the T-cell antigen receptor (TCR) and is the first critical step towards establishment of protective immunity against viruses and tumors. Fluorescently tagged, multivalent MHC class-I reagents (multimers) displaying individual peptides of interest have revolutionized detection of antigen specific T-cells. Staining with multimers followed by flow cytometry is routinely used to interrogate T-cell responses, to characterize antigen-specific TCR repertoires and to identify immunodominant clones (Glanville et al., *Nature* 547: 94-98 (2017); Dash et al., *Nature* 547: 89-93 (2017); DeWitt, *eLife* 7, e38358 (2018); Altman et al., *Science* 274: 94-96 (1996)). However, polyclonal repertoires are estimated to contain $10^5$-$10^8$ TCRs of distinct antigen specificities (Arstila et al., *Science* 286: 958 (1999)). Preparing libraries of properly conformed pMHC-I molecules displaying an array of peptide epitopes to probe such repertoires remains a significant challenge due to the inherent instability of empty (i.e. peptide deficient) MHC-I molecules. One current method involves the use of photo-cleavable peptides as conditional ligands, which can be replaced with peptides of choice upon UV-irradiation (Bakker et al., *Proc. Natl. Acad. Sci. U.S.A.* 105: 3825-3830 (2008)). Use of these highly sensitive photo-peptides necessitates a more elaborate protein purification protocol, and may lead to increased aggregation and sample loss during the peptide exchange step. Dipeptides, which compete with the C-terminus of bound peptides to promote exchange, have been proposed as alternatives to photo-cleavable peptides (Saini et al., *Proc. Natl. Acad. Sci. U.S.A.* 112: 202-207 (2015)).

TAPasin Binding Protein Related (TAPBPR) is a chaperone protein homologue of Tapasin involved in the quality control of pMHC-I molecules. TAPBPR associates with MHC-I molecules to edit the repertoire of displayed peptides at the cell surface (Morozov et al., *Proc. Natl. Acad. Sci. U.S.A.* 113: E1006-1015 (2016); and Hermann et al., *eLife* 4, (2015)). In a similar manner to Tapasin (Chen & Bouvier, *EMBO J.* 26: 1681-1690 (2007)), TAPBPR can bind several MHC-I alleles in vitro to promote the exchange of low-with high-affinity peptides (Morozov et al., *Proc. Natl. Acad. Sci. U.S.A.* 113: E1006-1015 (2016)). A detailed characterization of the TAPBPR peptide exchange cycle for the murine H-2Dd molecule has been performed using solution NMR (McShanb et al., *Nat. Chem. Biol.* 14: 811-820 (2018)).

This work revealed a critical role for C- and N-terminal peptide interactions with the MHC-I groove, which allosterically regulates TAPBPR release from the pMHC-I. Peptide binding is therefore negatively coupled to chaperone release and, conversely, the affinity of incoming peptides for the MHC-I groove is decreased by 100-fold in the presence of TAPBPR due to a widening of the MHC-I groove, as directly observed in X-ray structures of the MHC-I/ TAPBPR complex (Jiang et al., *Science* 358: 1064-1068 (2017); and Thomas & Tampé, *Science* 358: 1060-1064 (2017)).

Figure 8:
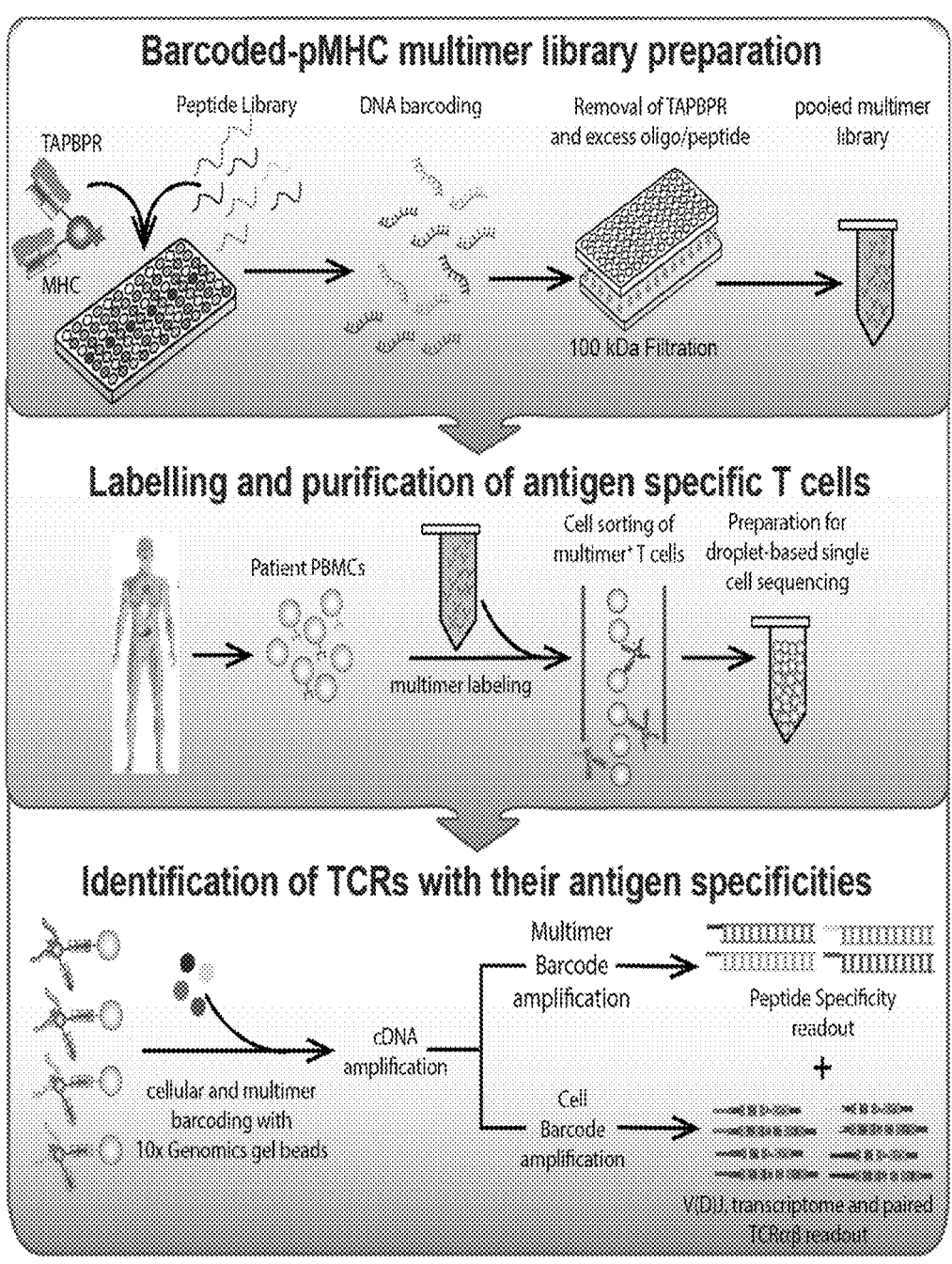
FIG. 8 provides a schematic depicting a method of linking peptide specificity with T-cell transcriptomes using the TAPBPR-exchanged MHC class I tetramer libraries provided herein. Fluorophore-labelled, empty-MHC/TAPBPR multimers are loaded with peptides of interest on a 96-well plate format and individually barcoded with DNA oligos designed for 10× Genomics and Illumina compatibility. TAPBPR and excess peptide, along with free oligo, are removed by centrifugation and pooled together. A single patient sample can be stained with the pooled multimer library, and collected by fluorescence-activated cell sorting. Tetramer associated oligos and cellular mRNA from individual cells are then barcoded using 10× Genomics gel beads, followed by cDNA synthesis, library preparation and library sequencing. This workflow enables the transcriptome and paired αβ TCR sequences to be linked with pMHC specificities in a single experiment.

Disclosed herein is the production of peptide-deficient MHC-I/TAPBPR complexes for two murine and one human MHC-I allotypes, independent of photo-cleavable peptide ligands. Empty MHC-I/TAPBPR complexes are stable for months, can be readily tetramerized and loaded with peptides of interest in a high-throughput manner (FIG. 8). The disclosed system has been adapted to incorporate multi-modal cellular indexing technology (ECCITE-seq) (Stoeckius, *Nat. Methods* 14: 865-868 (2017)). The resulting library of barcoded, TAPBPR-exchanged tetramers allows the multiplexed transcriptomic analysis of numerous antigen-specificities simultaneously, enabling TCR V(D)J identification and other transcriptional markers of interest in T-cells (FIG. 8).

Figures 9A, 9B, 9C, 9D, 9E, 9F, 9G:
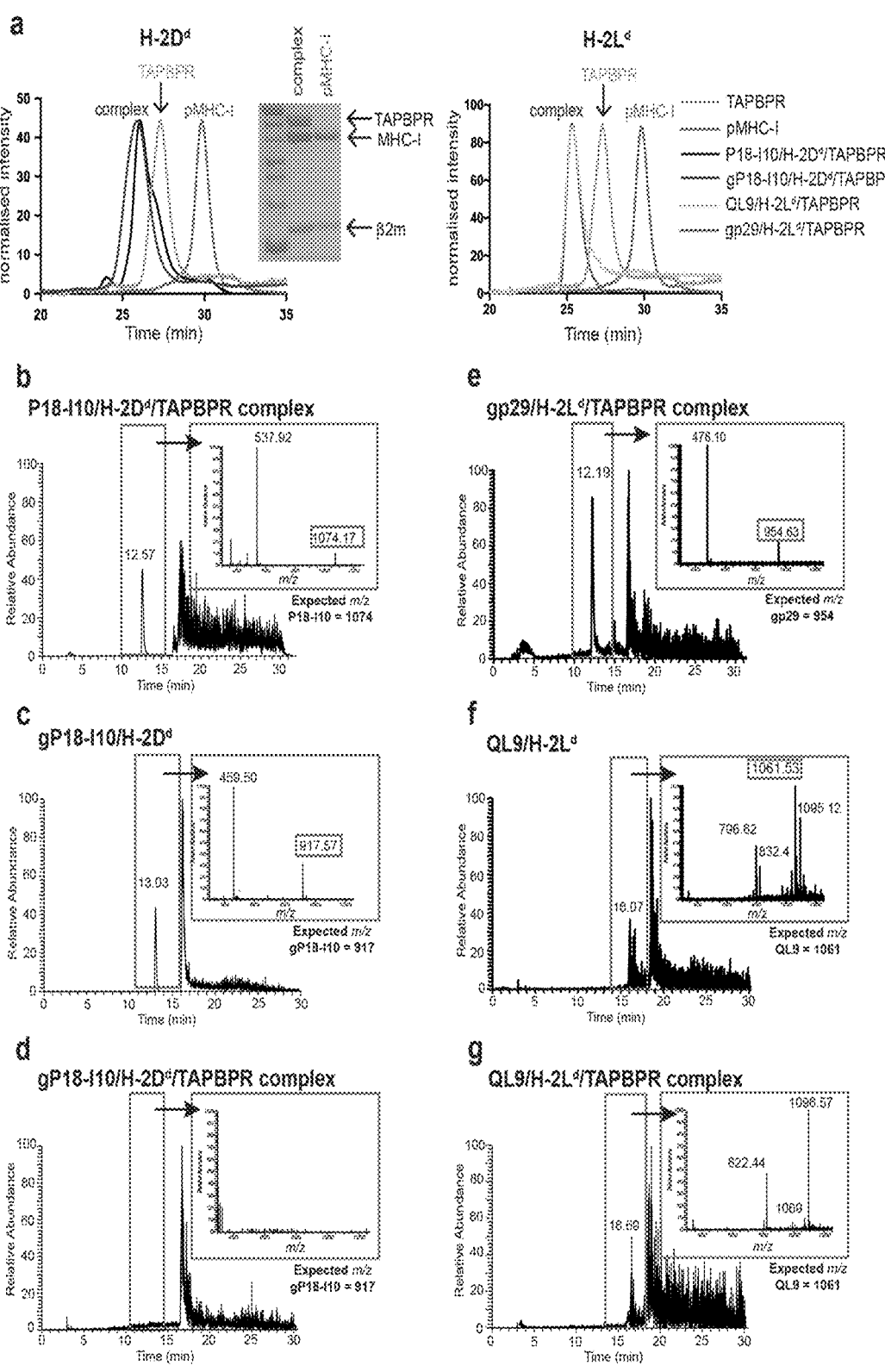
FIG. 9A-FIG. 9G depict the summary of a study showing that destabilizing "goldilocks" peptides promote isolation of empty murine MHC-I/TAPBPR complexes. (a) Size exclusion chromatography (SEC) elution profiles of H-2D$^d$ bound to RGPGRAFVTI (SEQ ID NO:5) (P18-I10) or GPGRAFVTI (SEQ ID NO:1) (gP18-I10) (left panel) and H-2L$^d$ bound to _PNVNIHNF (SEQ ID NO:6) (gp29) or QLSPFPFDL(SEQ ID NO:2) (QL9) (right panel) in the presence or absence of TAPBPR. SEC of H-2L$^d$ molecules shown was performed in the presence of 10 mM GF dipeptide. Inset shows SDS-PAGE analysis of elution fractions at 26 min/18 mL (pMHC-I/TAPBPR complex) and 30 min/15 mL (pMHC-I alone). (b-g) Analysis of MHC-I peptide occupancy by LC-MS. Chromatograms shown are filtered to only display peaks containing m/z ions of interest. Insets show MS analysis of the region indicated by the red box. (b) P18-I10/H-2D$^d$/TAPBPR complex, (c) gP18-I10/H-2D$^d$, (d) gP18-I10/H-2D$^d$/TAPBPR complex, (e) p29/H-2L$^d$/ TAPBPR complex, (f) QL9/H-2L$^d$/TAPBPR complex, (g) QL9/H-2L$^d$/TAPBPR complex.

Destabilizing placeholder peptides were used to circumvent the need for photo-cleavable ligands that have been previously used to demonstrate TAPBPR recognition of empty MHC-I molecules (Morozov et al., *Proc. Natl. Acad. Sci. U.S.A.* 113: E1006-1015 (2016)). A destabilizing N-terminally truncated mutant of the P18-I10 peptide _ GPGRAFVTI (SEQ ID NO:1) (gP18-I10) (McShanb et al., *Nat. Chem. Biol.* 14: 811-820 (2018)) was identified and is used herein. As disclosed herein, the gP18-I10 readily binds to H-2Dd, promoting in vitro refolding, but dissociates in the presence of TAPBPR to generate stable, empty H-2Dd/ TAPPBR complexes (FIGS. 9A and D). In contrast, full length P18-I10 remains captured in the groove of the H-2Dd/TAPBPR complex (FIGS. 9A and B). The previously reported 100-fold increase in the peptide off-rate for gP18-I10 relative to full-length P18-I10 peptide (McShanb et al., *Nat. Chem. Biol.* 14: 811-820 (2018)) likely arises from a loss of specific polar contacts in the H-2D$^d$ A-pocket (FIG. 10), and is further reflected in the predicted $IC_{50}$ values (24 µM gP18-I10 vs 23 nM for P18-I10). The gP18-I10 peptide can be referred to herein as a "goldilocks" peptide.

Figures 10A, 10B, 10C:
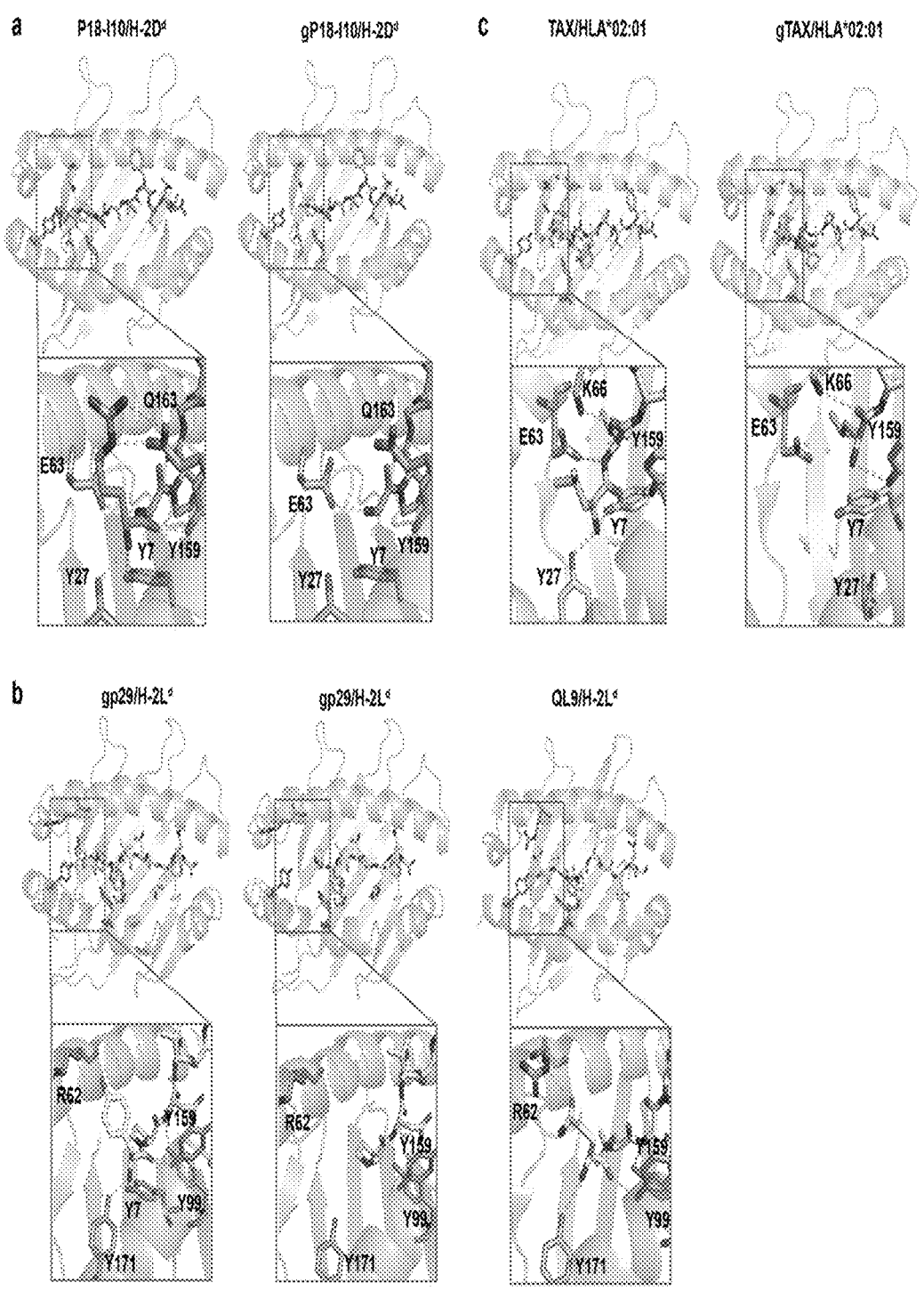
FIG. 10A-FIG. 10C are illustrations showing the reduced N-terminal contacts between destabilizing peptides and MHC-I. Crystal structures of the MHC-I peptide binding groove of (a) P18-I10/H-2D$^d$ (PDB 5IVX) (Natarajan etl al., Nature Communications 8: 15260 (2017)) and gP18-I10/H-2D$^d$ (modelled from 5IVX), with the bound peptides shown in light red. (b) Structure of p29/H-2L$^d$ (PDB 1LD9), gp29/ H-2L$^d$ modelled from 1LD9 (Balendiran et al., Proc Natl Acad Sci USA 94, 6880-6885 (1997)) and QL9/H-2L$^d$ (PDB 3TF7) (Adams, J. J. et al. et al., Immunity 35, 681-693 (2011)), with bound peptides shown in yellow. (c) TAX/ HLA-A*02:01 (PDB 1DUZ) and gTAX (PDB 1DUY) (Khan et al., J. Immunol. 164, 6398-6405 (2000)) with the bound peptide shown in green. Insets focus on the N-terminal region of each peptide, with 3 Å polar contacts between the peptide and the indicated MHC-I residues shown as dotted yellow lines.

Extending the same concept to a different murine MHC-I molecule, H-2L$^d$, an N-terminal truncation of the high-affinity p29 epitope _PNVNIHNF (SEQ NO:6) (denoted gp29, IC50 of 16.5 µM). However, the gp29 peptide remained bound to the H-2L$^d$/TAPBPR complex (FIGS. 9A and E, FIG. 10B), indicating that truncation of the extreme N-terminal residue cannot be used as a general rule to generate goldilocks peptides (FIG. 9E). As gp29 fits the typical H-2L$^d$ binding motif of xPxx[NA]xx[FLM], we explored QLSPFPFDL (SEQ ID NO:2) (QL9), a predicted low-affinity peptide (IC50 of 9.27 µM) with non-canonical Leu and Phe residues at position 2 and 5, respectively. Using full-length QL9 as a placeholder peptide, we could obtain empty H-2L$^d$:TAPBPR complexes by further adding 10 mM Gly-Phe dipeptide (GF), which promotes peptide release by directly competing for interactions in the F-pocket of the peptide-binding groove (Saini et al., *Proc. Natl. Acad. Sci. U.S.A.* 112: 202-207 (2015)) (FIGS. 9F and G and FIG. 10B). Taken together, these results establish the principle that destabilization of peptide interactions at both ends of the groove through a range of approaches, can be used to generate peptide-deficient MHC-I/TAPBPR complexes.

Figures 11A, 11B, 11C, 11D, 11E, 11F, 11G, 11H, 11I, 11J:
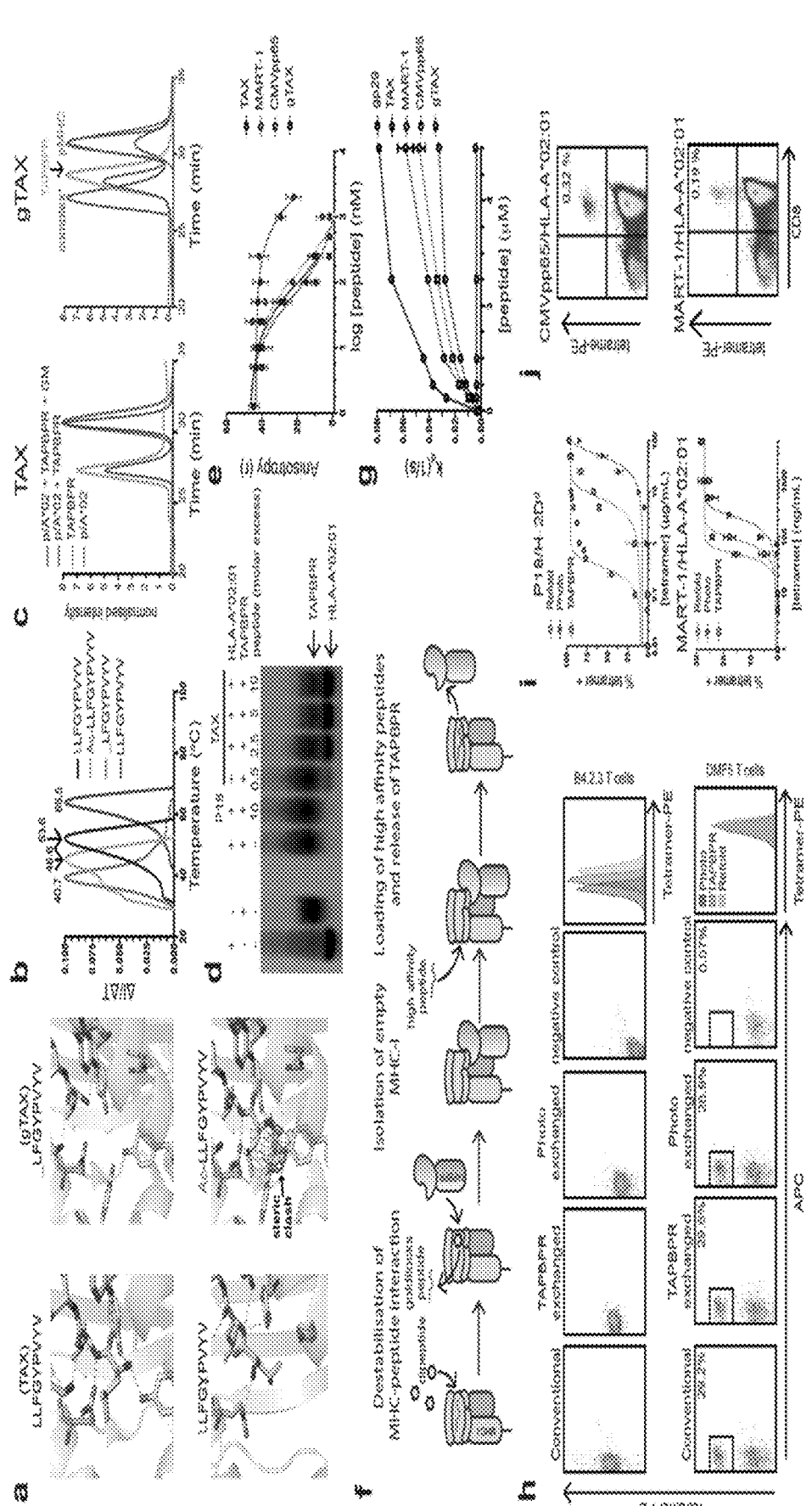
FIG. 11A-FIG. 11J is a summary of a study showing the isolation of empty MHC-I/TAPBPR complexes for high-throughput peptide exchange and tetramer library production. (a) Structure-based design of goldilocks peptides: comparison of polar contacts between HLA-A*02:01 and the N-terminal region of LLFGYPVYV (TAX) (SEQ ID NO:7) peptide (upper left). _LFGYPVYV (SEQ ID NO:3) (gTAX) (upper right), Ac-LLFGYPVYV (SEQ ID NO:4) (bottom right) and ILFGYPVYV (SEQ ID NO:8) where 1=D-Leucine (bottom left). Structures were modeled in PyMOL using PDB ID IDUZ[18]. (b) Peptide complex thermal stabilities of HLA-A*02:01 bound to TAX, ILFGYPVYV (SEQ ID NO:8), Ac-LLFGYPVYV (SEQ ID NO:4) and gTAX. (c) SEC TAPBPR binding assays of TAX/HLA-A02:01 (left), gTAX/HLA-A02:01 (right). (d) Native gel electrophoresis of HLA-A*02:01/TAPBPR complex dissociation in the presence of relevant high affinity peptide (TAX), and irrelevant peptide (P18-I10). (e) Competitive binding of TAMRA-TAX to purified HLA-A*02: 01/TAPBPR complexes from (c) as a function of increasing peptide concentration, measured by fluorescence polarization. (f) Conceptual diagram of TAPBPR-mediated capture of empty MHC-I molecules. (g) Bio-Layer Interferometry analysis of TAPBPR dissociation from HLA-A*02:01 in the presence of peptides of different affinity. (h) Representative flow cytometry analysis of tetramer staining using in vitro refolded (conventional), TAPBPR-exchanged and photo-exchanged tetramers. Top panels are mouse B4.2.3 TCR expressing T-cells stained with H-2D[d]:P18-I10 tetramers. Bottom panels are DMF5 TCR expressing T-cells stained with MART-1/HLA-A*02:01 tetramers. Negative controls are tetramers presenting gP18 or gTAX. (i) Tetramer titration of P18-I10/H-2D[d] (top) and MART-1/HLA-A*02:01 (bottom) of conventional refolded, TAPBPR-exchanged and photo-exchanged tetramers. Data shown is representative of two independent experiments performed in duplicate where the error bars indicate standard error of the mean. (j) Flow cytometry of IL-2/IL-7 expanded PBMCs stained with TAPBPR-exchanged HLA-A*02:01 tetramers loaded with CMVpp65 (top plot) and MART-1 (bottom plot).
Figures 12A, 12B, 12C, 12D:
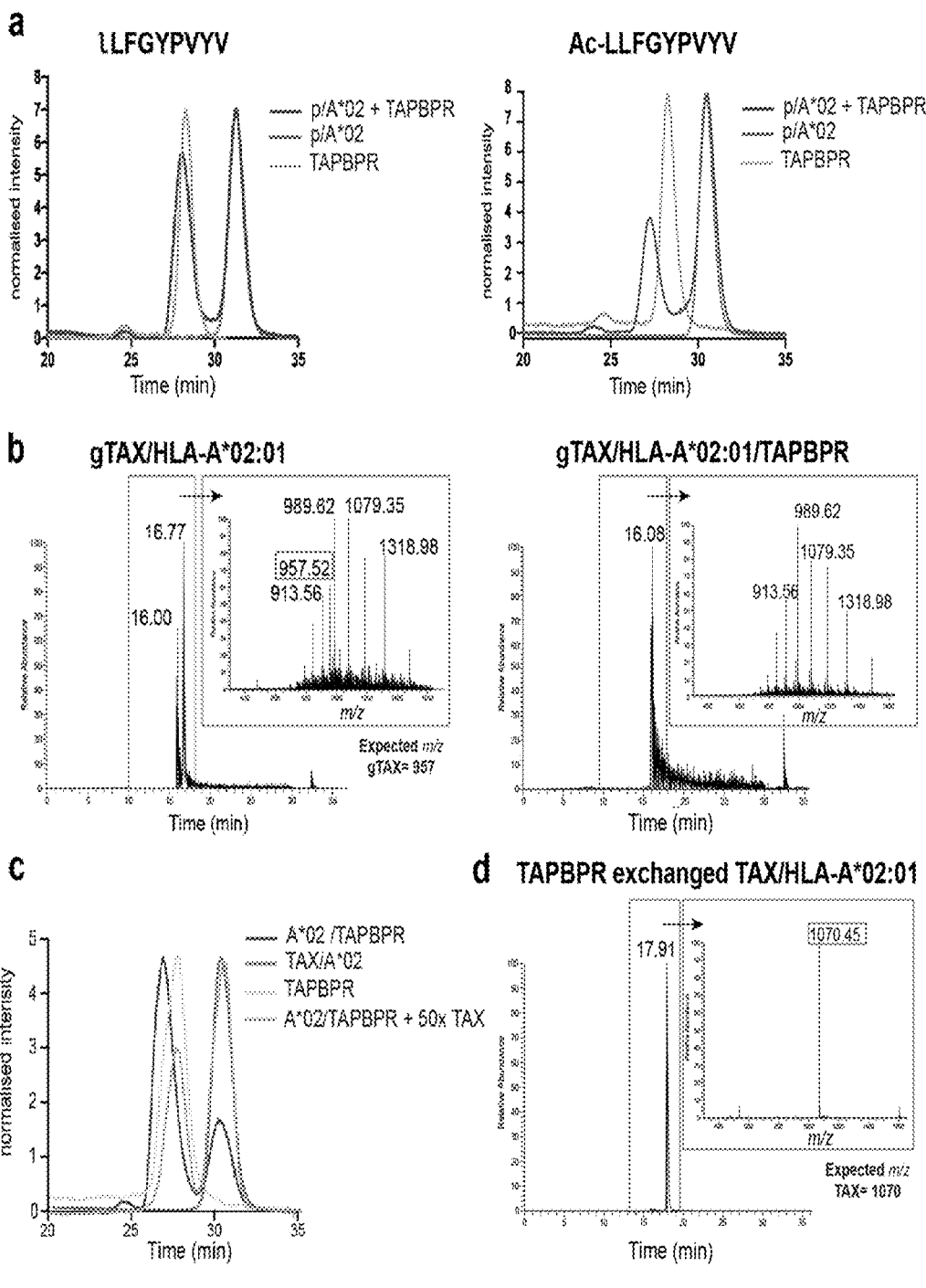
FIG. 12A-FIG. 12D are graphs providing an assessment of peptide occupancy of HLA-A*02:01/TAPBPR complexes. (a) SEC elution profile of ULFGYPVYV/HLA-A*02:01, (SEQ ID NO:8) where ı denotes a D-Leucine residue (left), and Ac-LLFGYPVYV/HLA-A*02:01, (SEQ ID NO:4) where Ac-L denotes an acetylated N-terminal Leucine residue (right), in the presence or absence of TAPBPR at an equimolar concentration. All binding experiments were performed in the presence of 10 mM GM dipeptide. (b) Analysis of peptide occupancy of gTAX/HLA-A*02:01 complex (left) and HLA-A*02:01/TAPBPR complex (right) by LC-MS. Chromatograms shown are filtered to display ions of interest. Inset: MS analysis of the region indicated. (c) SEC analysis of HLA-A*02:01/TAPBPR complex dissociation in the presence of high affinity (TAX) peptide. (d) MS analysis of TAX/HLA-A*02: 01 isolated from HLA-A*02:01/TAPBPR complexes loaded with TAX. All MS analysis is done on SEC purified HLA-A*02:01.

To extend these findings towards a high-throughput method for the production of HLA-tetramer libraries, the common human allele HLA-A*02:01 which displays a wide range of immunodominant viral and tumor epitopes was used, rendering the study of HLAA*02:01-restricted responses highly relevant (González-Galarza et al., *Nucleic Acids Res.* 43: D784-D788 (2015)). Guided by existing TAX/HLA-A*02:01 crystal structures (Khan et al., *J. Immunol.* 164: 6398-6405 (2000)), a number of mutants of the LLFGYPVYV (SEQ ID NO:7) (TAX) peptide were designed by progressively reducing N-terminal polar contacts with MHC-I groove residues while maintaining the anchor positions 2 and 8 (x[LM]xxxxx[ILV]) (FIGS. 11A and 10C). Comparison of thermal stabilities (Tm) of HLA-A*02:01 bound to N-terminal mutants of TAX showed a progressive reduction in Tm as a result of destabilization of the peptide complex upon loss of N-terminal polar contacts (FIGS. 11A and B). Both gTAX/HLAA* 02:01 and Ac LLFGYPVYV/HLA-A*02:01(SEQ ID NO:4), which gave the lowest Tm values at 40° C. and 46° C., respectively, were efficient goldilocks peptides promoting the formation of peptide-deficient MHC-I/TAPBPR complexes in the presence of 10 mM dipeptide (FIGS. 11C, F and 12A) as shown by LC-MS (FIG. 12B). Empty HLAA* 02:01/TAPBPR complexes were stable at room temperature for extended periods and could be stored at −80° C. or in lyophilized form. Incubation with high affinity TAX peptide induced dissociation of the complex, as observed both by native gel and SEC (FIG. 11D and FIG. 12C), with the loaded peptide detectable by LC-MS (FIG. 12D). High-affinity peptides (TAX, CMVpp65 or MART-1) could be readily loaded into the empty complex, out competing fluorescently labelled TAMRA-TAX for HLA-A*02:01 binding (FIG. 11E). Finally, using Bio-layer interferometry the dissociation rate of TAPBPR from HLA-A*02:01 was calculated, demonstrating a significant increase in the presence of high affinity peptides (TAX, CMVpp65 or MART-1) compared to low (gTAX and the irrelevant peptide gp29) (FIG. 11G). This observation correlates with the respective $T_m$ values of pMHC molecules refolded with different peptides (FIG. 18C).

The performance of TAPBPR-exchanged phycoerythrin (PE)-tetramers was compared with that of PE-tetramers generated using photo-cleavable ligands (Bakker et al., *Proc. Natl. Acad. Sci. U.S.A.* 105: 3825-3830 (2008)) or pMHC-I molecules refolded in vitro using standard protocols (Garboczi et al., *Proc. Natl. Acad. Sci.* 89: 3429-3433 (1992)). Staining of a B4.2.3 TCR transgenic T-cell line with P18-I10/H-2D$^d$ tetramers showed a two-fold enhancement in mean fluorescence intensity for TAPBPR-exchanged tetramers relative to photo-exchanged tetramers, and a lower intensity relative to refolded pMHC-I tetramers (FIG. 11H). This is further highlighted using detailed tetramer titrations, showing a staining saturation curve with an $EC_{50}$ of 6.2 µg/mL for TAPBPR-exchanged compared to 42.9 µg/mL for photo-exchanged tetramers (FIG. 11I). A similar trend was observed in MART-1/HLA-A*02:01 tetramer staining of Jurkat T-cells transduced with a MART-1 specific TCR, DMF5. (Johnson et al., *J. Immunol. Baltim. Md* 1950 177: 6548-6559 (2006)). Here, TAPBPR-exchanged tetramers showed a 2.6-fold improvement in $EC_{50}$ values relative to photo-exchanged tetramers, despite staining with equivalent fluorescence intensities at saturating concentrations (FIGS. 11H and I). Under polyclonal conditions, TAPBPR-exchanged tetramers were also effective at identifying low frequency CMVpp65 and MART-1 specific T-cells among cytokine expanded PBMCs (FIG. 11J).

Figures 13A, 13B, 13C:
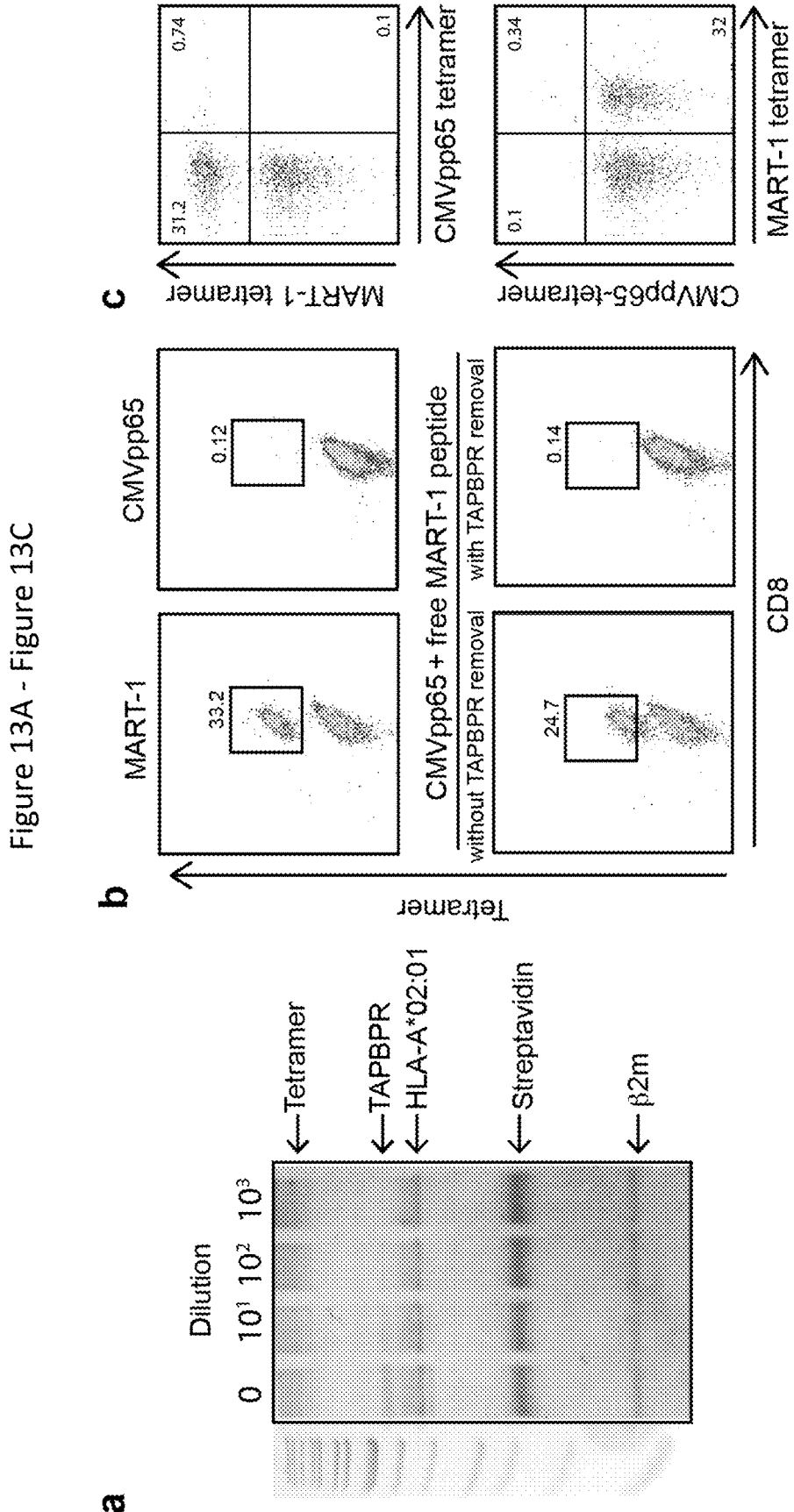
FIG. 13A-FIG. 13C depict a gel and representative plots, respectively, showing that removal of TAPBPR abrogates the exchange of peptides on and between tetramers for library production. (a) SDS-PAGE of tetramers washed using a 100 kDa spin filter at 10, 100 and 1,000-fold dilutions. (b) Representative plots showing tetramer staining of DMF5 T-cells with HLA-A*02:01 tetramers prepared by TAPBPR exchange of either the MART-1 epitope specific to the DMF5 TCR, or the irrelevant epitope CMVpp65 (top panels). A very low level (0.12%) of CMVpp65-tetramer positive DMF5 T-cells can be detected, likely due to nonspecific staining. DMF5 T-cells were independently stained with CMVpp65-tetramers incubated with free MART1 peptide at 10-fold molar excess (relative to pMHC-I) without TAPBPR removal (bottom left) or upon complete removal of TAPBPR, as shown in (a) (bottom right), showing recovery of a low (0.14%) level of background staining in the absence of TAPBPR. (c) Staining of DMF5 T-cells using a 1:1 mixture of PE-CMVpp65:APC-MART-1 tetramers (top panel), or PE-MART-1: APC-CMVpp65 tetramers (bottom panel). In each plot, both tetramer samples were prepared individually using TAPBPR exchange, followed by complete removal of TAPBPR and excess peptide, mixing of the two tetramers and overnight incubation at 4° C. The absence of a significant PE-tetramer positive population (0.1%-x-axis) in the top panel, or an APC-tetramer positive population in the bottom pane (0.1%-y-axis) is indicative of a negligible background of cross-exchange of peptides between tetramers in the absence TAPBPR, allowing their incorporation into stable tetramer libraries. Numbers in the plots indicate the percentage of total cells.

The disparity between the performance of P18-I10/H-2D$^d$ tetramers compared to MART-1/HLA-A*02:01 could result from an increase in binding affinity between TAPBPR and H-2D$^d$ (FIG. 9A). Since high concentrations of TAPBPR can promote the release of high affinity peptides, the persistence of TAPBPR following exchange may partially regenerate peptide-deficient MHC-I molecules, thereby reducing the staining efficiency of the resulting tetramers. In a library format this may lead to "scrambling" of excess peptides between MHC tetramers upon mixing, which would limit the use of molecular indices or "barcodes" to label tetramers according to their displayed peptides. We found that the presence of TAPBPR resulted in the exchange of CMVpp65 loaded on HLA-A*02:01 tetramers for free MART-1 peptide (FIG. 13B). Thus, full removal of TAPBPR molecules was readily achieved using spin column dialysis immediately following the tetramerization and peptide loading steps (FIG. 8), as confirmed by SDS-PAGE (FIG. 13A). The resulting pMHC-I tetramers did not capture free high-affinity peptides, even when present at 20× molar excess. Furthermore, peptide exchange between tetramers was not observed (FIGS. 13B and C).

Variant MHC Class I With Decreased Binding to TAPBPR

Figures 14A, 14B, 14C, 14D:
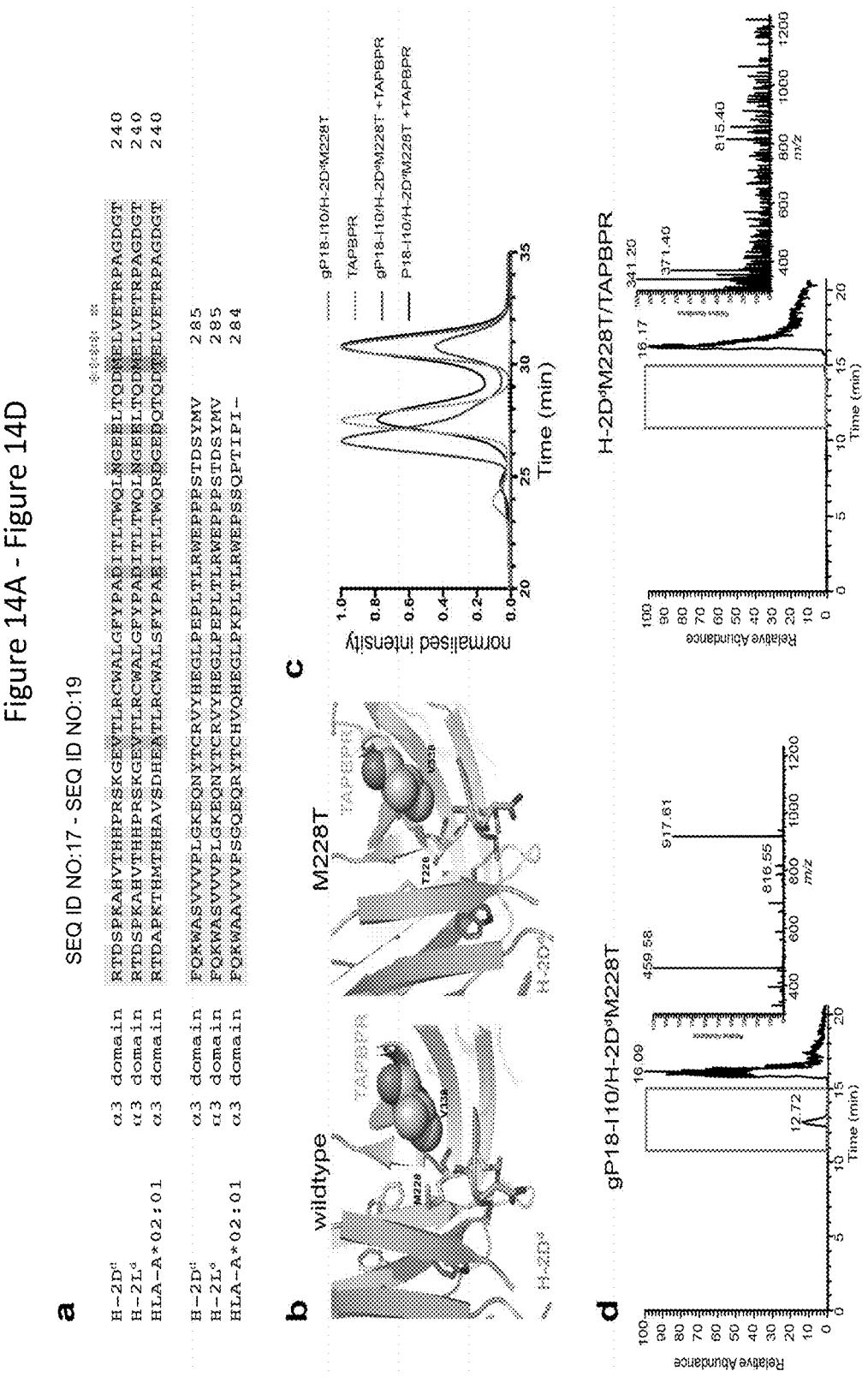
FIG. 14A-FIG. 14D are schematics and graphs, showing the fine-tuning of MHC-I/TAPBPR interactions towards tetramer library production through the design of α3 domain mutants. (a) Alignment of the α3 domain sequences from murine H-2D[d], H-2L[d] and human HLA-A*02:01. Conserved residues are highlighted in yellow, conservative substitutions are highlighted in pale red. The M228T mutation site is highlighted in blue. * indicates residues directly participating in TAPBPR binding, as shown in published mutagenesis studies and crystal structures19,13. (b) TAPBPR/H-2D[d] α3 domain interface from PDB ID 5WER[13] (left panel) and with the M228T mutation modeled (right panel). (c) SEC traces of H-2D[d]M228T refolded with either high affinity p18-I10 or goldilocks gP18-I10 peptides, with and without TAPBPR. (d) LC/MS peptide occupancy analysis of SEC-purified gP18/H-2D[d]M228T and H-2D[d]M228T/TAPBPR peaks from (c).

TAPBPR interactions with murine MHC-I molecules known to form stable complexes even when bound to high affinity peptides (McShanb et al., *Nat. Chem. Biol.* 14: 811-820 (2018)), an effect which limits their use towards high-throughput tetramer library production, were fine-tuned using H-2D$^d$ with mutations at the α3 domain of the heavy chain which participates in direct interactions with TAPBPR, but not with the bound peptide. Specifically, M228 is located at an edge loop of the α3 immunoglobulin fold and forms a hydrophobic contact with TAPBPR residues in the X-ray structure of the H-2D$^d$/TAPBPR complex (Jiang et al., *Science* 358: 1064-1068 (2017) and Hermann et al., *J. Immunol* 191: 5743-5750 (2013)) (FIG. 14A). It was hypothesized that mutating this position from a Met, present in H-2D$^d$ and H-2L$^d$, to a polar Thr residue, present in HLA-A*02:01, would lead to a reduced binding affinity for TAPBPR. In contrast to WT H-2D$^d$, H-2D$^d$ M228T did not bind TAPBPR in the presence of the high affinity P18-I10 peptide (FIG. 14C). However, upon dissociation of the goldilocks gP18-I10 peptide, H-2D$^d$M228T bound TAPBPR to generate an empty, peptide receptive complex (FIG. 14C and D). These results further highlight the requirements of a system that is amenable to large-scale tetramer library production using our approach: i) formation of a stable TAPBPR complex with an empty molecule and ii) TAPBPR dissociation upon binding of high affinity peptides to the MHC-I groove.

MHC class I Tetramer Libraries

Figure 16:
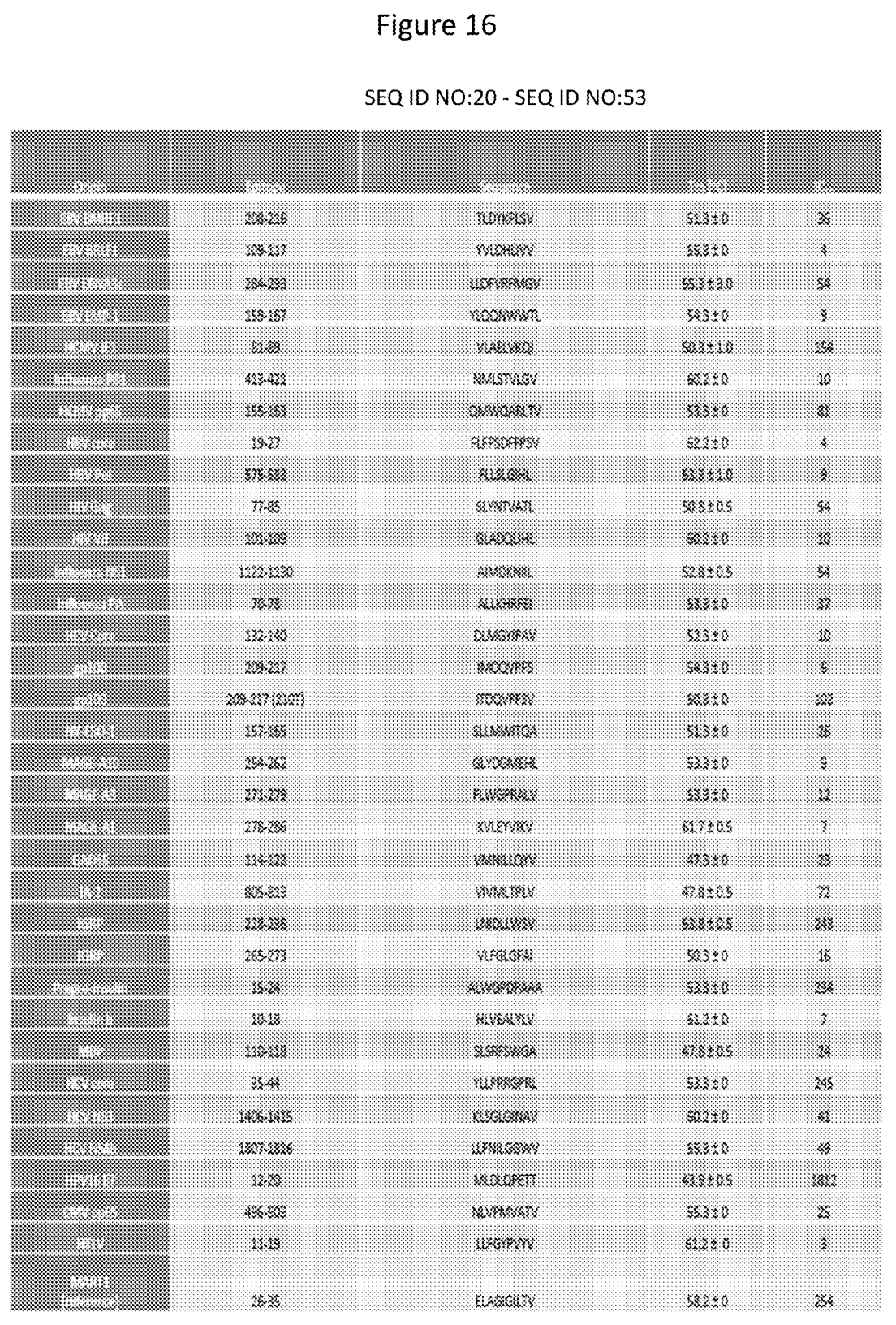
Figure 17A:
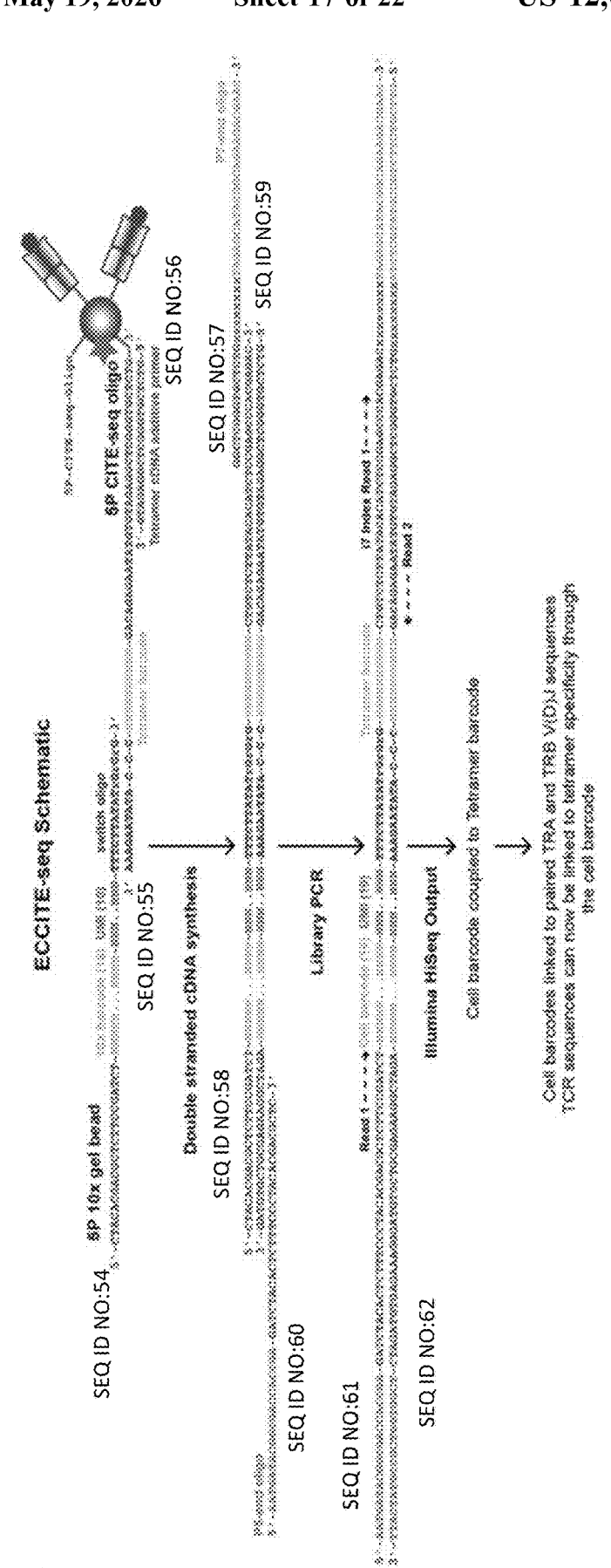
FIG. 17A-FIG. 17C provide a summary of studies, showing ECCITE-seq adapted to capturing barcoded MHC tetramers. (a) Biotinylated 5P CITE-seq[15] oligos were conjugated to streptavidin tetramers. The oligos contain a unique tetramer barcode, a switch oligo sequence that provides a handle for 10× compatibility and incorporation of 5P 10× gel bead oligos during cDNA synthesis, in addition to a 3' Illumina NGS sequencing handle (Nextera read 2). The 10× 5P kit was used with specific protocol modifications[15] to capture oligo-derived tags and mRNA-derived cDNA. Only oligo capture is shown here. After separation of the large and small fractions, following cDNA amplification with additive primer, the low molecular weight fraction was amplified with 10× Genomics SI-PCR oligo and a Nextera P7 oligos to create a sequencing library compatible with Illumina instruments. The high molecular weight cDNA fraction was processed according to manufacturer's instructions. Tetramer tags and TCR cDNAs from the same cell will share the same cell barcode and can be associated. (b) Bulk amplification of all PE-tetramer barcodes contained in library 2. (c) Comparative staining of DMF5 Jurkat T-cells with a single (non-barcoded) PE-tetramer prepared by TAPBPR exchange of the MART-1 peptide (left panel), versus an equal concentration of the full barcoded tetramer library 2 of 34 epitopes, including MART-1 (right panel).
Figures 17B, 17C:
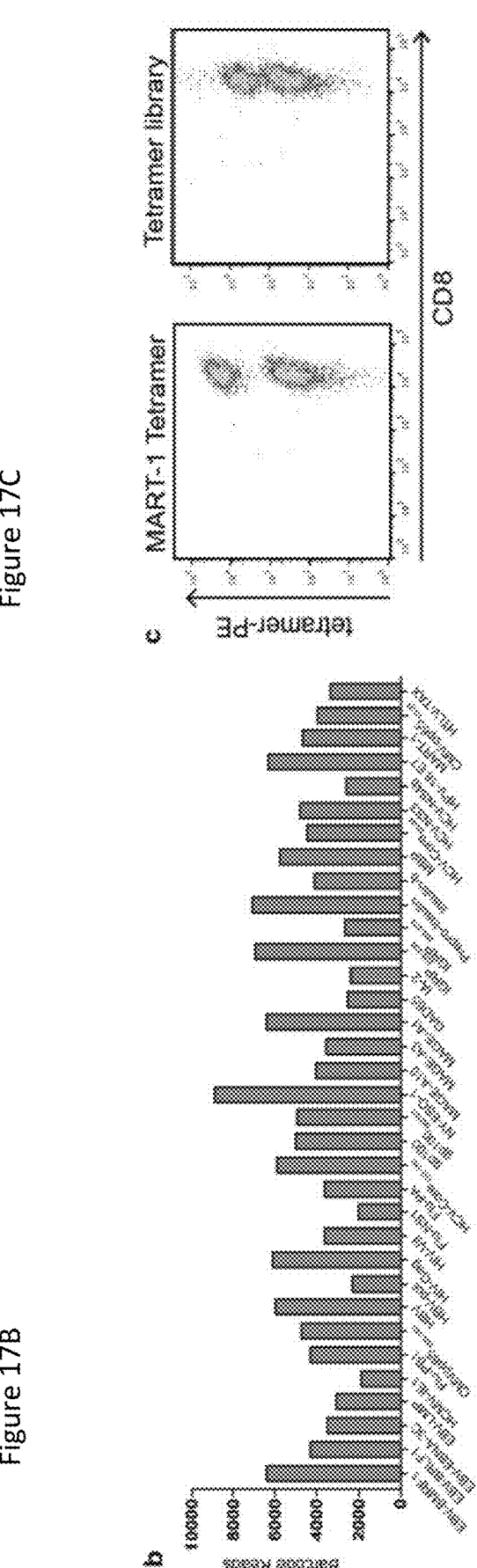
Figure 19:
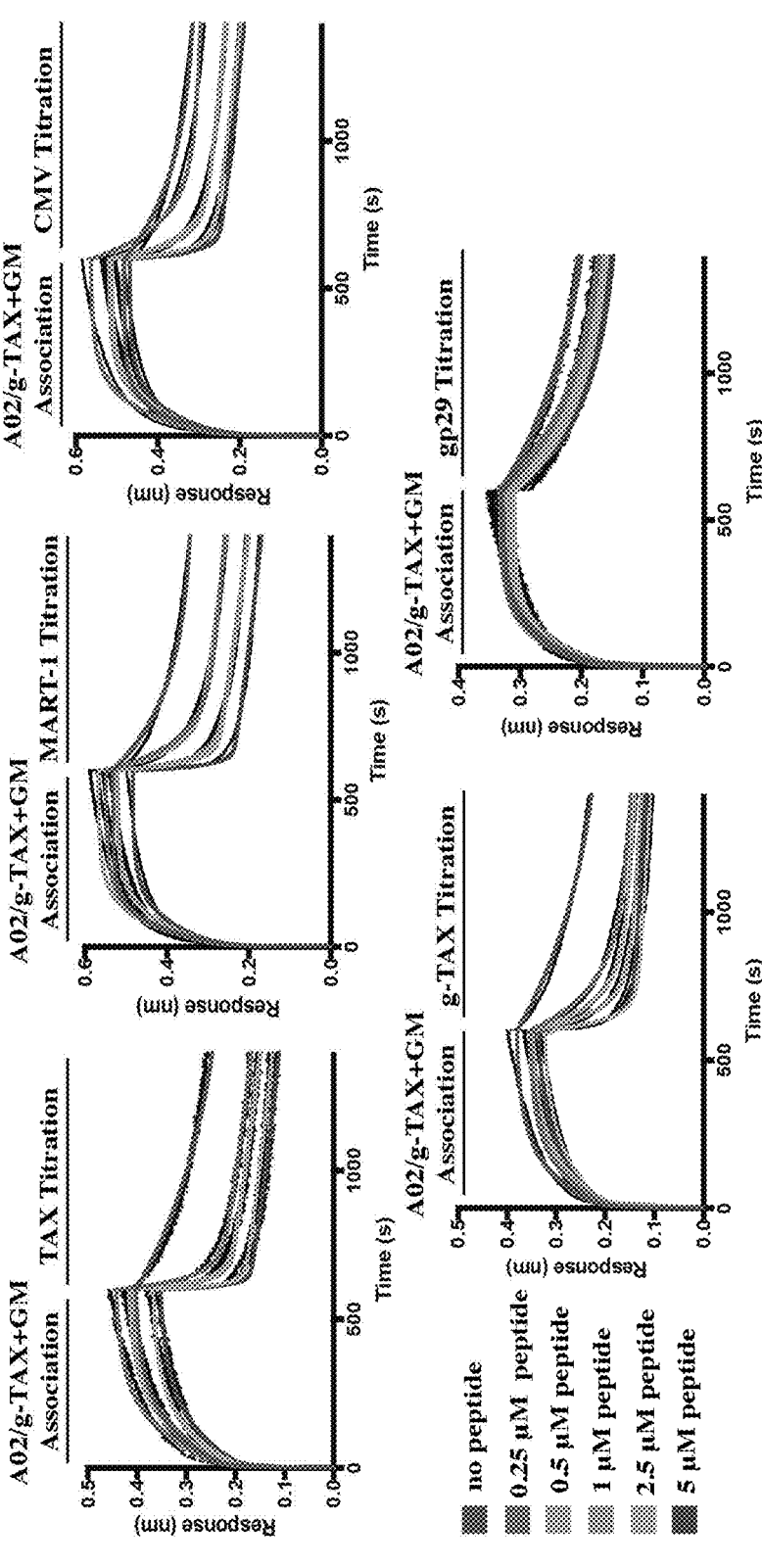
FIG. 19 shows graphs with measurements of peptide-induced HLA-A*02:01 dissociation from TAPBPR using Bio-layer Interferometry. Binding and dissociation of HLA-A*02:01 from immobilized TAPBPR on a tip surface. The association of a peptide deficient HLA-A*02:01 to TAPBPR was achieved by the addition of 10 mM GM dipeptide (FIG. 2C). The dissociation of HLA-A*02:01 was measured in the presence of buffer supplemented with increasing concentrations of the indicated peptide. Dissociation data was corrected using a reference biosensor of immobilized TAPBPR (not bound to HLA-A*02:01), in buffer. Data shown are representative of 2 independent experiments. Raw data points are shown in black. All series were fit locally using a 2:1 model with a $R^2$ of 0.99 or greater, shown as colored curves. The derived pseudo first-order dissociation rate constants, $k_d$, are plotted as a function of peptide concentration in FIG. 10G.

Two tetramer libraries, one containing 29 tumor epitopes identified in neuroblastoma tissues and another encompassing a range of 31 viral, neoantigen and autoimmune epitopes were constructed using the disclosed methods. (FIGS. 15 and 16). To link pMHC specificities with TCR V(D)J sequences present in polyclonal samples, the TAPBPR-exchanged fluorophore-labelled MHC-I-tetramers were barcoded with biotinylated DNA oligonucleotides (oligos) (Bentzen et al., *Nat. Biotechnol.* 34: 1037-1045 (2016)). We used an in-house oligo design compatible with 10× Genomics gel bead oligos in the 5' V(D)J product (FIG. 8 and FIG. 17A) adding an additional modality of cellular information to an ECCITE-seq method. This method incorporates a cellular barcode into cDNA generated from both tetramer oligos and TCR mRNA, thus the pairing of cellular barcodes can connect TCR sequences and other mRNAs with tetramer specificities. Formation of stable pMHC species upon loading of each peptide was confirmed using two complementary DSF assays (FIGS. 18 and 19), performed on a 96-well format. After exhaustive dialysis of TAPBPR, excess barcodes and peptides, all individual peptide loading reactions were pooled into a single tetramer library sample for staining. The final libraries were further validated for: i) the presence of all barcodes, using bulk sequencing reactions (FIG. 17B) and ii) staining of Jurkat/MA cells transduced with the DMF5 receptor which recognizes a "reference" peptide, MART-1, included in both libraries (FIG. 17C). Here, while the use of oligonucleotide barcodes leads to a reduced staining efficiency relative to non-barcoded tetramers, likely due to the lower avidity for the pMHC antigen, the observed signal intensities ($10^3$-$10^4$) were sufficient to distinguish the approx. 33% population of DMF5+ cells from the negative fraction.

To confirm that the approach has sufficient sensitivity to detect antigen-specific T cells within a heterogeneous sample, 1% DMF5+ Jurkat T-cells were spiked into a sample of CD8+ enriched PBMCs cocultured with DCs and stained with the library of 31 neoepitopes, including the MART-1 peptide which is cognate to the DMF5 receptor. 100,000 tetramer positive cells were collected and 3,000 were sequenced. From this sample, the 256 cells with the highest number of DMF5 reads were extracted and plotted together with their corresponding MART-1 tetramer reads (FIG. 20A). In total, recovered 85 cells with ≥10 MART-1 tetramer counts were recovered, 76 of which showed ≥10 DMF5 TCR reads (considered DMF5 positive) giving an approximate false positive rate of 10.6% (FIG. 20A). Conversely, 6 DMF5 TCR positive cells showed ≤10 MART-1 tetramer counts, resulting in a false negative rate of 7.9%. The low number of cells with significant tetramer barcode reads could be a function of tetramer avidity, exacerbated by high dilutions through the 10× Genomics system prior to cDNA preparation. Overall, a clear positive relationship between MART-1 counts and DMF5 TCR reads was observed suggesting that our tetramer libraries can be used to identify sparse populations of antigen-specific T cells within a heterogeneous sample.

Finally, the methodology was used to probe distinct TCR specificities present in a polyclonal repertoire of T-cells. A total of 2×10$^6$ CD8$^+$ T cells isolated from the spleen of an EBV-positive donor were stained using our barcoded tetramer library consisting of 34 viral, autoimmune and tumor epitopes (FIG. 16). After sorting, 3,000 tetramer positive cells were loaded on the 10× platform for single-cell sequencing. ECCITE-seq analysis retrieved 1,722 cell barcodes, the majority of which were associated with <2 tetramer reads, giving a low apparent background. 110 cells were further identified as tetramer-enriched, defined as cells with >10 tetramer reads for at least one peptide specificity. 27 tetramer-enriched cells bound to >5 different peptide epitopes, 5 of which showed no bias towards a particular epitope and were excluded from subsequent analysis. Among the final set of 102 tetramer-enriched cells, a total of 16 distinct epitope specificities were identified, with an average of 200 reads per cell for each dominant tetramer (FIG. 20B). Specifically, a large fraction of tetramer-enriched cells had high reactivity for the NY-ESO-1 epitope (37 cells), followed by EBV-BRLF1 (16 cells), MAGE-A1 (10 cells) and IGRP$_{265-273}$ (7 cells). Towards validating the significance of our results, we focus our analysis of barcodes corresponding to the EBV-BRLF1 epitope whose TCR repertoire has been previously characterized using ad hoc tetramers prepared using conventional refolding protocols (Trautman et al., *Euro J Immunol.* 32: 3181-3190 (2002)). Inspection of V(D)J TCR sequence reads from tetramer-enriched cells identified a clear bias towards the usage of TRAV8-1 (50%) with TRAJ34 (50%), TRBV19 (21%), TRBJ2-1 (36%) and TRBJ2-7 (29%), a finding consistent with published reports on EBV-BRLF1 specific repertoires[21]. Whereas the β-chain CDR3 sequences were more variable, analysis of TRA CDR3 sequences further identified a known public alpha chain CDR3 (CAVKDTDKLIF) which was previously linked to a functional TCR, specific for the EBV-BRLF1 epitope[22]. This sequence was observed in half of EBV-BRLF1 tetramer-enriched cells, and was not detected in cells enriched for any other tetramer (FIG. 20E). Taken together, these results corroborate the initial findings using the DMF5 cells (FIG. 20A), and further suggest that the disclosed barcoded pMHC libraries prepared using TAPBPR exchange are of sufficient quality and staining affinity to identify antigen-specific TCRs present within polyclonal repertoires.

Disclosed herein is a robust method to isolate stable, empty-MHC-I molecules at milligram quantities that can be readily loaded with peptides of choice in a high-throughput manner. Rather than relying on chemically synthesized conditional ligands, the disclosed method employs a molecular chaperone, TAPBPR, in an analogous manner to the antigen processing pathway used by cells to load MHC-I molecules with immunodominant peptides. In combination with a simple indexing design that is compatible with the 10× Genomics system, the method can efficiently link paired TCR V(D)J sequences to their pMHC specificities in a polyclonal sample setting. The peptide exchange and barcode sequencing workflow has no theoretical upper limit with respect to library size, other than the cost of peptide and oligo synthesis, which renders it suitable for the simultaneous analysis of hundreds of epitope specificities. In addition to expediting tetramer library preparation and the identification of novel TCR specificities, the method can be readily extended to include the analysis of complete transcriptomes (Stoeckius, Nat. Methods 14: 865-868 (2017)), thereby providing a toehold for probing functional aspects of TCR: pMHC recognition.

Methods

Peptides: All peptide sequences are given as standard single letter code. Peptides used for MHC refoldings and production of the neoepitope library were purchased from Genscript at 98% purity or as pepsets from Mimotopes (Australia) as crude peptides and dissolved in 8.25% Acetonitrile, 25% DMSO, and 66.75% $H_2O$. Peptides containing modifications: TAMRA-TAX and GILGFVFXL (SEQ ID NO:9) (where X=3-amino-3-(2-nitrophenyl)-propionic acid) were purchased from Biopeptik at 98% purity. ILFGYPVYV (SEQ ID NO:8) and Ac-LLFGYPVYV (SEQ ID NO:4) were synthesized in house using standard FMOC chemistry. Peptide binding affinities were predicted using netMHCpan 4.0. (Jurtz et al., J. Immunol. Baltim. Md 1950 199: 3360-3368 (2017))

In vitro refolding of pMHC molecules: Plasmid DNA encoding the luminal domain of class I MHC (MHC-I) heavy chains H-2D$^d$, HLA-A*02:01, H-2L$^d$ and human β2-microglobulin (hβ2m,) were provided by the tetramer facility at Emory University, and transformed into Escherichia coli BL21(DE3) (Novagen). MHC-I proteins were expressed in Luria-Broth media, and inclusion bodies (IBs) were purified as previously described (Li et al., J. Mol. Biol. 283: 179-191 (1998)). In vitro refolding of pMHC-I molecules was performed by slowly diluting a 200 mg mixture of MHC-I and hβ2m at a 1:3 molar ratio over 24 hours in refolding buffer (0.4 M L-Arginine, 100 mM Tris pH 8, 2 mM EDTA, 4.9 mM reduced glutathione, 0.57 mM oxidized glutathione) containing 10 mg of synthetic peptide purchased from Genscript at 98% purity at 4° C. H-2D$^d$ heavy chain was refolded with RGPGRAFVTI (SEQ ID NO:5) (P18-I10) derived from HIV gp120 or _GPGRAFVTI (SEQ ID NO:1) (gP18-I10). H-2L$^d$ was refolded with _PNVNIHNF (SEQ ID NO:6) (gp29) or QLSPFPFDL (SEQ ID NO:2) (QL9) derived from oxo-2-gluterate dehydrogenase. HLA-A*02:01 was refolded with variants of LLFGYPVYV (SEQ ID NO:7) (TAX) derived from HTLV-1 including _LFGYPVYV (SEQ ID NO:3) (gTAX), N-terminally acetylated TAX (Ac-LLFGYPVYV) (SEQ ID NO:4), ILFGYPVYV (SEQ ID NO:8) where the first residue is a D-leucine or with ELAGIGILTV (MART-1) derived from Melan-A. Refolds were allowed to proceed for 96 h followed by size exclusion chromatography (SEC) using a HiLoad 16/600 Superdex 75 column (150 mM NaCl, 25 mM Tris pH 8) at a flow rate of 1 mL/min, followed by anion exchange chromatography on a mono Q 5/50 GL column at 1 mL/min using a 40 minute 0-100% gradient of buffer A (50 mM NaCl, 25 mM Tris pH 8) and buffer B (1M NaCl, 25 mM Tris pH 8). Typical protein yields from a 1L refold were 5 to 10 mg of purified pMHC-I.

Recombinant TAPBPR expression and purification: The luminal domain of TAPBPR was expressed using a stable Drosophila S2 cell line (Morozov et al., Proc. Natl. Acad. Sci. U.S.A. 113: E1006-1015 (2016)) (Dr Kannan Natarajan (National Institutes of Health)) induced with 1 mM CuSO$_4$ for 4 d and purified as previously described (Jiang et al., Science 358: 1064-1068 (2017)). Briefly, His-tagged TAPBPR was captured from the supernatant by affinity chromatography using high-density metal affinity agarose resin (ABT, Madrid). Eluted TAPBPR was further purified by size exclusion using a Superdex 200 10/300 increase column at a flow rate of 0.5 mL/min in 100 mM NaCl and 20 mM sodium phosphate pH 7.2.

Size exclusion chromatography and formation of MHC-I/TAPBPR complexes: SEC analysis of MHC-I/TAPBPR interaction was performed by incubating 40 μM purified pMHC-I molecules with purified TAPBPR at a 1:1 molar ratio in 100 mM NaCl, 20 mM sodium phosphate pH 7.2 for 1 h at room temperature. Complexes were resolved on a Superdex 200 10/300 increase column (GE healthcare) at a flow rate of 0.5 mL/min in 100 mM NaCl and 20 mM sodium phosphate pH 7.2 at room temperature. MHC-I/TAPBPR complexes eluted at 26.5 min. In the case of H-2L$^d$ and HLA-A*02:01, 10 mM GF and GM were added respectively both to the initial incubation and to the running buffer during chromatography.

LC-MS: Peptide occupancy of SEC purified MHC-I was determined by HPLC separation on a Higgins PROTO300 C4 column (5 μm, 100 mm×21 mm) followed by electrospray ionisation performed on a Thermo Finnigan LC/MS/MS (LQT) instrument. Peptides were identified by extracting expected m/z ions from the chromatogram and deconvoluting the resulting spectrum in MagTran.

Preparation of photo-exchanged pMHC-I: H-2D$^d$ refolded with RGPGRAFXTI (SEQ ID NO:10) (photo-P18-I10) and HLA-A*02:01 refolded with GILGFVFXL (SEQ ID NO:9), where X is the photo-cleavable residue 3-amino-3-(2-nitrophenyl)-propionic acid, were UV-irradiated at 365 nm for 1 h in the presence of 20-fold molar excess peptide at room temperature. Reactions were iced for 1 h then centrifuged at 14,000 rpm for 10 min to remove aggregates. Photo-exchanged pMHC-I was then used for DSF analysis or tetramer.

Differential scanning fluorimetry: To measure thermal stability of pMHC-I molecules, 2.5 µM of protein was mixed with 10× Sypro Orange dye in matched buffers (20 mM sodium phosphate pH 7.2, 100 mM NaCl) in MicroAmp Fast 96 well plates (Applied Biosystems) at a final volume of 50 µL. DSF was performed using an Applied Biosystems ViiA qPCR machine with excitation and emission wavelengths at 470 nm and 569 nm respectively. Thermal stability was measured by increasing the temperature from 25° C. to 95° C. at a scan rate of 1° C./min. Melting temperatures ($T_m$) were calculated in GraphPad Prism 7 by plotting the first derivative of each melt curve and taking the peak as the $T_m$ (FIG. 18A). Determination of $T_m$ values of TAPBPR exchanged molecules additionally required subtraction of the TAPBPR melt curve from the curve obtained for the complex, then calculating the first derivative. This procedure, on average, enhanced the $T_m$ values calculated for TAPBPR exchanged pMHC-I molecules by 1.5° C., compared to refolded and photo-exchanged pMHC-I molecules. All samples were analyzed in duplicate and the error is represented as the standard deviation of the duplicates analyzed independently.

Bio-Layer Interferometry: In each experiment, HISIK biosensor tips (ForteBio) were first baselined in a buffer of 20 mM sodium phosphate pH 7.2, 100 mM NaCl and then coated with 6 µg/mL of HIS-Tagged TAPBPR in a matched buffer until the response was between 0.3 nm and 0.4 nm for each tip. TAPBPR coated biosensor tips were then dipped into matched buffer supplemented with 0.02% TWEEN-20 and 0.5 mg/mL BSA for 6 minutes to block non-specific interaction and as secondary baseline step. Subsequent steps were performed in the secondary baseline buffer (20 mM sodium phosphate pH 7.2, 100 mM NaCl, 0.02% TWEEN-20, 0.5% BSA). Biosensor tips were then dipped into buffer containing 10 µM HLA-A*02:01/g-TAX and 10 mM GM dipeptide to facilitate peptide deficient MHC/TAPBPR formation for 10 minutes. After peptide deficient MHC/TAPBPR formation on the biosensor tips, they were dipped into buffer supplemented with 0-5 µM of the indicated peptides for 14 minutes to facilitate pMHC dissociation from TAPBPR. Data was processed after subtraction of the reference sensor tip data set which was coated with TAPBPR but was dipped into buffer instead of HLA-A*02:01+GM, Y-axis alignment to the secondary baseline, and an interstep correction alignment to dissociation. All data was locally fit for association and dissociation with a 2:1 (heterogenous) binding model. Goodness of fit was determined with $R^2$ values of 0.99 and above. All experiments were performed using an Octet Red 96e system and analyzed with the Octet data analysis HT v. 11.1 software.

Nano Differential Scanning Fluorimetry (nanoDSF): In a volume of 20 µl, 1 µM peptide deficient HLA-A*02:01/TAPBPR was incubated with 20 µM of various peptides (FIG. 15) in a buffer of 20 mM sodium phosphate pH 7.2, 100 mM NaCl, 0.02% TWEEN-20 for at least one hour. 10 uL of each sample was loaded on the Prometheus NT.48 instrument (NanoTemper) using the high sensitivity capillaries. NanoDSF measurements are performed using a temperature ramp rate of 1° C./min from 25° C. to 95° C. and an LED intensity of 20%. Data is analyzed using the PR Control software (NanoTemper). Melting temperatures ($T_m$ values) correspond to the inflection points of the first derivative of the 330/350 nm fluorescence ratio. Experiments performed in duplicates and the shaded areas (FIG. 18B) are representative of the error.

Native gel electrophoresis: Peptide-deficient MHC-I/TAPBPR complexes were incubated with the indicated molar ratio of relevant (TAX) or irrelevant (P18-I10) peptide for 1 h at room temperature. Samples were run at 90 V on 8% polyacrylamide gels in 25 mM TRIS pH 8.8, 192 mM glycine, at 4° C. for 4.5 hours and developed using InstantBlue (Expedeon).

Fluorescence anisotropy: Fluorescence anisotropy was performed using TAX peptide labeled with TAMRA dye ($K_{TAMRA}$LFGYPVYV) (herein called TAX-TAMRA). 50 nM peptide-deficient HLA-A*02:01/TAPBPR complexes in 100 mM NaCl, 20 mM sodium phosphate and 0.05% (v) tween-20, were incubated with 0.75 nM TAMRA-TAX and graded concentrations of MART-1, CMVpp65 or unlabeled TAX peptide in total volumes of 100 uL in black 96 well assay plate (Costar 3915) for 2 hours at room temperature while Fluorescence anisotropy (r) was recorded. Fluorescence anisotropy (FA) was recorded on a Perkin Elmer Envision 2103 with an excitation filter of $\lambda_{ex}$=531 nm and an emission filter of $\lambda_{em}$=595 nm. FA were normalized against TAMRA-TAX alone. Measurements were recorded every 30 seconds and data points represented are an average of FA values acquired following 95-105 minutes incubation. All experiments are representative of at least 3 individual experiments run in triplicates. Data points were plotted and fit using a sigmoidal response curve in GraphPad Prism 7.

Preparation of barcoded peptide exchanged tetramers: Purified, BirA-tagged pMHC-I molecules were biotinylated using the Bulk BirA: BirA biotin-protein ligase bulk reaction kit (Avidity), according to the manufacturer's instructions. Biotinylated pMHC-I was buffer exchanged into PBS pH 7.4 using a PD-10 desalting column. Biotinylation was confirmed by SDS-PAGE in the presence of excess streptavidin and by LC-MS. Biotinylated peptide-deficient MHC-I/TAPBPR complexes were generated and purified by SEC as described above. Empty-MHC-I/TAPBPR complex eluting at 26.5 min, was collected and confirmed to contain both MHC-I and TAPBPR by SDS-PAGE. Purified complexes were confirmed peptide-deficient by LC-MS and stored at −80° C. Tetramerization of empty-MHC-I/TAPBPR was performed by adding a 2:1 molar ratio of biotinylated MHC-I/TAPBPR to streptavidin-PE or streptavidin-APC (Prozyme) in five additions over 1 h on ice. Tetramerized empty-MHC-I/TAPBPR complexes were then aliquoted into 96 well plates at 2 µg of total MHC-I per well. For tetramer barcoding, custom biotinylated DNA oligos (IDT) were diluted to a concentration of 8.5 µM prior to use. Each tetramer was barcoded by adding 2:1 molar equivalent of DNA-barcodes relative to streptavidin and incubated for 1 hr, at 4° C. Empty barcoded-MHC-I/TAPBPR tetramers were then exchanged with peptides of interest by adding a 20-molar excess of peptide to each well and incubating for 1 hour. Additionally, 8 molar excess biotin (to block any free streptavidin sites) was added and incubated for a further 1 h at room temperature. After exchange, tetramers were transferred to 100 kDa spin columns (Amicon) and washed with 1000 volumes of PBS to remove TAPBPR and excess peptide and barcodes. After washing, exchanged tetramers were pooled and stored at 4° C. for up to 3 weeks.

Cell Culture: 58 α⁻β⁻-T-cells expressing the B4.2.3 TCR, which recognizes P18-I10 bound to H-2D$^d$, were obtained from Dr. Kannan Natarajan (NIH). TCR β chain-deficient Jurkat-MA T-cells expressing the DMF5 TCR, which recognizes Melan-A epitope MART-1 bound to HLA-A*02:01. Cells were grown in DMEM supplemented with 10% FBS, 25 mM HEPES pH 7, 2 µM β-mercaptoethanol, 2 mM L-glutamine, 100 U/mL penicillin/streptomycin and 1×non-essential amino acids. Cells were maintained in exponential phase in a humidified incubator at 37° C. with 5% $CO_2$.

Splenocytes from HLA-A*02:01 organ donors were obtained through the Human Pancreas Analysis Program (University of Pennsylvania) after informed consent by each donor's legal representative. For cytokine expansion, PBMCs from healthy HLA-A*02:01 matched donors (Children's Hospital Philadelphia) were cultured in X-VIVO 15 (Lonza) supplemented with 10% human serum albumin, 25 mM HEPES pH 7, 2 μM β-mercaptoethanol, 2 mM L-glutamine, 100 U/mL penicillin/streptomycin, 1×non-essential amino acids, 1000 U/mL recombinant human IL-2, 10 ng/ml recombinant human IL-7 and 10 ng/ml recombinant human IL-15 for 2 weeks prior to analysis.

Generation of DMF5 T-cell line: Retrovirus for transduction of Jurkat/MA (Mimitou et al., Nature Methods, published Apr. 23, 2019) and primary CD8 T cells was produced using Platinum-A retroviral packaging cell line. DMF5 cassette was assembled using previously described CDR3 sequences and V(D)J family genes, codon optimized, synthesized, and cloned into pMP71 retroviral vector. Jurkat/MA cells were plated in 6-well plates at $7\times10^5$ cells/well and transfected with 2.5 mg of retroviral vector pMP71 using Lipofectamine 3000 (Life Technologies, Invitrogen). After 24 hours, medium was replaced with IMDM-10% FBS or AIM-V-10% FBS. Supernatants were harvested and filtered with 0.2 mM filters after 24 hours incubation and transferred to Jurkat/MA cells in 6-well plates pre-treated with 1 mL well/Retronectin (20 mg/mL in PBS, Takara Bio. Inc.,) at $1\times10^6$ cells/well and spinoculated with 2 mL of retroviral supernatant at 800 g for 30 min at RT. After 24 hours, cells were washed and PBS, and cultured in IMDM-10% FBS. Jurkat/MA cells were stained with MART-1 dextramer and sorted for dextramer-positive cells.

PBMC/DC co-culture: Normal donor monocytes were plated on day 1 in 6-well plates at $5\times10^6$/well in RPMI-10 FBS supplemented with 10 ng/ml IL-4 (Peprotech) and 800 IU/ml GM-CSF (Peprotech) and incubated at 37° C. overnight. On day 2, fresh media supplemented with 10 ng/ml IL-4 and 1600 IU/ml GM-CSF was added to the monocytes and incubated at 37° C. for another 48 hours. On day 4, non-adherent cells were removed and immature dendritic cells washed and pulsed with 5 uM peptide in AIM-V-10% FBS supplemented with 10 ng/ml IL-4, 800 IU/ml GM-CSF, 10 ng/ml LPS (Sigma-Aldrich), and 100 IU/ml IFN-γ (Peprotech) at 37° C. overnight. Day I was repeated on days 4 and 8 to generate dendritic cells for the second and third stimulations on days 8 and 12, respectively. On day 5, normal donor-matched CD8+ T cells were co-cultured with the pulsed dendritic cells in AIM-V-10% FBS. Day 5 protocol was repeated on day 8 and day 12 using dendritic cells generated on days 4 and 8 for the second and third stimulation, respectively.

Flow cytometry: Tetramer analysis was carried out by staining $2\times10^5$ cells with anti-CD8α mAb (BD Biosciences) and 1 μg/mL HLA-A02:01/MART-1 tetramer or 50 μg/mL H-2D$^d$/P18-I10 tetramer for 1 h on ice, followed by two washes with 30 volumes of FACS buffer (PBS, 1% BSA, 2 mM EDTA). All flow cytometric analysis was performed using a BD LSR II instrument equipped with FACSDiva software (BD Biosciences). For cell sorting experiments, cryopreserved human splenocytes were thawed and rested in RPMI media (10% FBS, 1% L-glutamine, 1% Pencillin/Streptomycin). CD8$^+$ T cells were enriched by negative selection using magnetic beads according to the manufacturer's protocol (STEMCELL Technologies). Cells were then treated with dasatinib (50 nM, Sigma-Aldrich) for 30 minutes prior to staining. Afterward, 50 μL each of PE and APC versions of the tetramer library were added (final amount was 0.5 μg pMHC per tetramer) were added for 15 minutes at room temperature. Cells were stained with anti-CCR7-APC-Cy7 (G043H7, BioLegend) for 10 minutes at 37° C.; with LIVE/DEAD Fixable Aqua (Thermo Fisher Scientific) for 10 minutes at room temperature; with an antibody cocktail containing: anti-CD14-BV510 (M5E2, BioLegend), anti-CD19-BV510 (HIB19, BioLegend), anti-CD3-APC-R700 (UCHT1, BD Biosciences), anti-CD4-PE-Cy5.5 (S3.5, Thermo Fisher Scientific), anti-CD8-BV605 (RPA-T8, BioLegend), and anti-CD45RA PE-CF594 (HI100, BD Biosciences) for 20 minutes at room temperature. Cells were washed and resuspended in BD pre-sort buffer (BD Biosciences). Cell sorting was performed on a FACS Aria FUSION (BD Biosciences)

Live cells were gated based on forward and side scatter profiles and data was analyzed using FlowJo software (Tree Star). For $EC_{50}$ determination, tetramer concentrations were calculated based on total amount of pMHC-I at the time of exchange. Titrations were performed on the appropriate cell line in duplicate in two independent experiments. The percentage of tetramer+ T-cells was measured relative to the staining achieved at the highest concentration tested within each experiment. $EC_{50}$ values were calculated by fitting a Boltzmann sigmoidal function to the data with the lower constraint set to 0 and upper constraints set to 95 for B4.2.3 and 28 for DMF5 in GraphPad Prism 7.

ECCITE-seq: Post sorting, samples were prepped for the 10× Genomics 5P V(D)J kit workflow, and processed according to the ECCITE-seq protocol (Mimitou et al., Nature Methods, published Apr. 23, 2019), with these modifications:

For cDNA amplification, 1 uL of 0.2 uM tetramer additive (GTCTCGTGGGCTCGGAGATG) (SEQ ID NO:11) was spiked into the reaction.

Post cDNA PCR, a 0.6×SPRI cleanup was performed, resulting in the larger cDNA fragments being retained on the beads, and the tetramer tags in the supernatant. After separation of the two fractions and elution from the beads, a portion of the cDNA was used to perform TCR alpha/beta amplification and library prep, as described in the 10× genomics protocol.

A separate portion of the cDNA elution was used to perform a DMF5 receptor specific enrichment, using a hemi-nested PCR strategy akin to that used for the TCRα/β enrichment. All PCRs were performed using 2×KAPA Hifi Master Mix. Primers for PCRs: PCR—DMF5_PCR1 (GAAATTCACGGCGCACAGG) (SEQ ID NO:12) with SI-PCR primer (10×). PCR2—DMF5_PCR2 (CCTTGGCACCCGAGAAT-TCCAGCTTGGCTGGCTGTCTCTGATC) (SEQ ID NO:13) and P5_generic (AATGATACGGCGAC-CACCGAGATCTACAC) (SEQ ID NO:14). PCR3 (to add P7 end and sample index)—RPI-x primer ("x" nucleotides comprise a user-defined index) CAAGCAGAAGACGGCAT-ACGAGATxxxxxxxxGTGACTG-GAGTTCCTTGGCACCCG AGAATTCCA (SEQ ID NO:15) and P5_generic.

The supernatant of the 0.6×SPRI purification in step 2 above was purified with 2 rounds of 2×SPRI. First, 1.4× SPRI was added to the supernatant to bring up the volume to 2×, followed by two rounds of 80% ethanol washes. After eluting in water, an additional 2×SPRI cleanup was performed. Post second cleanup, the tetramer tags were converted to a sequenceable library by PCR with SI-PCR and N7XX ("x" nucleotides comprise a user-defined index)

CAAGCAGAAGACGGCAT-
ACGAGATxxxxxxxxGTCTCGTGGGCTCGG (SEQ ID
NO:16).

Sequencing and Analysis: Individual tetramers were
pooled in one library sample prior to sequencing. Samples
were sequenced on a Miseq using a v2 300 cycle kit (151
cycles R1, 8 cycles 11, 151 cycles read 2). Post sequencing,
TCR fastq files were pooled together for each sample, then
analyzed using cellranger vdj 3.0.0 against the GRCh38
reference genome (v2.0.0, as provided by the 10× website).
To identify the DMF5 receptor, CITE-seq-Count version
1.4.1 was used to search for the DMF5 specific tag, using
default parameters (hamming distance set to 5). For tetram-
ers, CITE-seq-Count version 1.4.1 was used using all default
parameters, with the exception of hamming distance set to 1, and a whitelist to search for only cells with TCR found by
10×.

TCR Repertoire Analysis: All analysis was performed
using the PE-tetramer barcodes alone. Cells with ≥10
tetramer reads were clustered into pMHC specificity groups
based on the tetramer barcode read. Cells with multiple
tetramers with >10 reads were clustered based on the most
frequent tetramer read (≥50% of total tetramer reads for that
T-cell). All TCR sequences identified (partial or complete)
were used in global VJ usage analysis. In cases where
multiple TCRs were read, only TCR sequences with the
highest true reads were used (generally representative of
≥90% of TCR reads for that T-cell). Known receptors and
CDRs were queried and identified using VDJdb and litera-
ture searches.

---

```
                        SEQUENCE LISTING

Sequence total quantity: 68
SEQ ID NO: 1              moltype = AA  length = 9
FEATURE                  Location/Qualifiers
REGION                   1..9
                         note = Synthetic gP18-I10 placeholder peptide
source                   1..9
                         mol_type = protein
                         organism = synthetic construct
SEQUENCE: 1
GPGRAFVTI                                                          9

SEQ ID NO: 2              moltype = AA  length = 9
FEATURE                  Location/Qualifiers
REGION                   1..9
                         note = Synthetic QL9 placeholder peptide
source                   1..9
                         mol_type = protein
                         organism = synthetic construct
SEQUENCE: 2
QLSPFPFDL                                                          9

SEQ ID NO: 3              moltype = AA  length = 8
FEATURE                  Location/Qualifiers
REGION                   1..8
                         note = Synthetic gTAX placeholder peptide
source                   1..8
                         mol_type = protein
                         organism = synthetic construct
SEQUENCE: 3
LFGYPVYV                                                           8

SEQ ID NO: 4              moltype = AA  length = 8
FEATURE                  Location/Qualifiers
REGION                   1..8
                         note = Synthetic acetylated TAX placeholder peptide
MOD_RES                  1
                         note = Leu is acetylated leucine
source                   1..8
                         mol_type = protein
                         organism = synthetic construct
SEQUENCE: 4
LFGYPVYV                                                           8

SEQ ID NO: 5              moltype = AA  length = 10
FEATURE                  Location/Qualifiers
REGION                   1..10
                         note = Synthetic HIV gp160 epitope P18-I10
source                   1..10
                         mol_type = protein
                         organism = synthetic construct
SEQUENCE: 5
RGPGRAFVTI                                                         10

SEQ ID NO: 6              moltype = AA  length = 8
FEATURE                  Location/Qualifiers
REGION                   1..8
                         note = Synthetic gp29
source                   1..8
```

-continued

```
                              mol_type = protein
                              organism = synthetic construct
SEQUENCE: 6
PNVNIHNF                                                              8

SEQ ID NO: 7          moltype = AA  length = 9
FEATURE               Location/Qualifiers
REGION                1..9
                      note = Synthetic TAX placeholder peptide
source                1..9
                      mol_type = protein
                      organism = synthetic construct
SEQUENCE: 7
LLFGYPVYV                                                             9

SEQ ID NO: 8          moltype = AA  length = 8
FEATURE               Location/Qualifiers
REGION                1..8
                      note = Synthetic D-leucine synthetic TAX placeholder peptide
MOD_RES               1
                      note = Leu is a D-leucine
source                1..8
                      mol_type = protein
                      organism = synthetic construct
SEQUENCE: 8
LFGYPVYV                                                              8

SEQ ID NO: 9          moltype = AA  length = 9
FEATURE               Location/Qualifiers
REGION                1..9
                      note = Synthetic peptide
MOD_RES               8
                      note = Xaa is 3-amino-3-(2-nitrophenyl)-propionic acid
source                1..9
                      mol_type = protein
                      organism = synthetic construct
SEQUENCE: 9
GILGFVFXL                                                             9

SEQ ID NO: 10         moltype = AA  length = 10
FEATURE               Location/Qualifiers
REGION                1..10
                      note = Synthetic photo-P18-I10
MOD_RES               8
                      note = Xaa is 3-amino-3-(2-nitrophenyl)-propionic acid
source                1..10
                      mol_type = protein
                      organism = synthetic construct
SEQUENCE: 10
RGPGRAFXTI                                                            10

SEQ ID NO: 11         moltype = DNA  length = 20
FEATURE               Location/Qualifiers
misc_feature          1..20
                      note = Synthetic tetramer additive
source                1..20
                      mol_type = other DNA
                      organism = synthetic construct
SEQUENCE: 11
gtctcgtggg ctcggagatg                                                20

SEQ ID NO: 12         moltype = DNA  length = 19
FEATURE               Location/Qualifiers
misc_feature          1..19
                      note = Synthetic PCR - DMF5_PCR1 primer
source                1..19
                      mol_type = other DNA
                      organism = synthetic construct
SEQUENCE: 12
gaaattcacg gcgcacagg                                                 19

SEQ ID NO: 13         moltype = DNA  length = 43
FEATURE               Location/Qualifiers
misc_feature          1..43
                      note = Synthetic PCR2 - DMF5_PCR2 primer
source                1..43
                      mol_type = other DNA
                      organism = synthetic construct
SEQUENCE: 13
```

-continued

```
ccttggcacc cgagaattcc agcttggctg gctgtctctg atc                        43

SEQ ID NO: 14          moltype = DNA   length = 29
FEATURE                Location/Qualifiers
misc_feature           1..29
                       note = Synthetic P5_generic primer
source                 1..29
                       mol_type = other DNA
                       organism = synthetic construct
SEQUENCE: 14
aatgatacgg cgaccaccga gatctacac                                        29

SEQ ID NO: 15          moltype = DNA   length = 64
FEATURE                Location/Qualifiers
misc_feature           1..64
                       note = Synthetic RPI-x primer
variation              25..31
                       note = n is a, c, g, or t
source                 1..64
                       mol_type = other DNA
                       organism = synthetic construct
SEQUENCE: 15
caagcagaag acggcatacg agatnnnnnn ngtgactgga gttccttggc acccgagaat      60
tcca                                                                   64

SEQ ID NO: 16          moltype = DNA   length = 47
FEATURE                Location/Qualifiers
misc_feature           1..47
                       note = Synthetic N7XX primer
variation              25..32
                       note = n is a, c, g, or t
source                 1..47
                       mol_type = other DNA
                       organism = synthetic construct
SEQUENCE: 16
caagcagaag acggcatacg agatnnnnnn nngtctcgtg ggctcgg                    47

SEQ ID NO: 17          moltype = AA   length = 105
FEATURE                Location/Qualifiers
REGION                 1..105
                       note = Synthetic peptide
source                 1..105
                       mol_type = protein
                       organism = synthetic construct
SEQUENCE: 17
RTDSPKAHVT HHPRSKGEVT LRCWALGFYP ADITLTWQLN GEELTQDMEL VETRPAGDGT      60
FQKWASVVVP LGKEQNYTCR VYHEGLPEPL TLRWEPPPST DSYMV                     105

SEQ ID NO: 18          moltype = AA   length = 105
FEATURE                Location/Qualifiers
REGION                 1..105
                       note = Synthetic peptide
source                 1..105
                       mol_type = protein
                       organism = synthetic construct
SEQUENCE: 18
RTDSPKAHVT HHPRSKGEVT LRCWALGFYP ADITLTWQLN GEELTQDMEL VETRPAGDGT      60
FQKWASVVVP LGKEQNYTCR VYHEGLPEPL TLRWEPPPST DSYMV                     105

SEQ ID NO: 19          moltype = AA   length = 103
FEATURE                Location/Qualifiers
REGION                 1..103
                       note = Synthetic peptide
source                 1..103
                       mol_type = protein
                       organism = synthetic construct
SEQUENCE: 19
RTDAPKTMTH HAVSDHEATL RCWALSFYPA EITLTWQRDG EDQTQDTELV ETRPAGDGTF      60
QKWAAVVVPS GQEQRYTCHV QHEGLPKPLT LRWEPSSQPT IPI                       103

SEQ ID NO: 20          moltype = AA   length = 9
FEATURE                Location/Qualifiers
REGION                 1..9
                       note = Synthetic epitope
source                 1..9
                       mol_type = protein
                       organism = synthetic construct
SEQUENCE: 20
TLDYKPLSV                                                               9
```

-continued

```
SEQ ID NO: 21                moltype = AA   length = 9
FEATURE                      Location/Qualifiers
REGION                       1..9
                             note = Synthetic epitope
source                       1..9
                             mol_type = protein
                             organism = synthetic construct SEQUENCE: 21
YVLDHLIVV                                                              9

SEQ ID NO: 22                moltype = AA   length = 10
FEATURE                      Location/Qualifiers
REGION                       1..10
                             note = Synthetic epitope
source                       1..10
                             mol_type = protein
                             organism = synthetic construct SEQUENCE: 22
LLDFVRFMGV                                                            10

SEQ ID NO: 23                moltype = AA   length = 9
FEATURE                      Location/Qualifiers
REGION                       1..9
                             note = Synthetic epitope
source                       1..9
                             mol_type = protein
                             organism = synthetic construct SEQUENCE: 23
YLQQNWWTL                                                              9

SEQ ID NO: 24                moltype = AA   length = 9
FEATURE                      Location/Qualifiers
REGION                       1..9
                             note = Synthetic epitope
source                       1..9
                             mol_type = protein
                             organism = synthetic construct SEQUENCE: 24
VLAELVKQI                                                              9

SEQ ID NO: 25                moltype = AA   length = 9
FEATURE                      Location/Qualifiers
REGION                       1..9
                             note = Synthetic epitope
source                       1..9
                             mol_type = protein
                             organism = synthetic construct SEQUENCE: 25
NMLSTVLVG                                                              9

SEQ ID NO: 26                moltype = AA   length = 9
FEATURE                      Location/Qualifiers
REGION                       1..9
                             note = Synthetic epitope
source                       1..9
                             mol_type = protein
                             organism = synthetic construct SEQUENCE: 26
QMWQARLTV                                                              9

SEQ ID NO: 27                moltype = AA   length = 11
FEATURE                      Location/Qualifiers
REGION                       1..11
                             note = Synthetic epitope
source                       1..11
                             mol_type = protein
                             organism = synthetic construct SEQUENCE: 27
FLFPSDFFPS V                                                          11

SEQ ID NO: 28                moltype = AA   length = 9
FEATURE                      Location/Qualifiers
REGION                       1..9
                             note = Synthetic epitope
source                       1..9
                             mol_type = protein
                             organism = synthetic construct

SEQUENCE: 28
```

```
FLLSLGIHL                                                                   9

SEQ ID NO: 29              moltype = AA  length = 9
FEATURE                   Location/Qualifiers
REGION                    1..9
                          note = Synthetic epitope
source                    1..9
                          mol_type = protein
                          organism = synthetic construct
SEQUENCE: 29
SLYNTVATL                                                                   9

SEQ ID NO: 30              moltype = AA  length = 9
FEATURE                   Location/Qualifiers
REGION                    1..9
                          note = Synthetic epitope
source                    1..9
                          mol_type = protein
                          organism = synthetic construct
SEQUENCE: 30
GLADQLIHL                                                                   9

SEQ ID NO: 31              moltype = AA  length = 9
FEATURE                   Location/Qualifiers
REGION                    1..9
                          note = Synthetic epitope
source                    1..9
                          mol_type = protein
                          organism = synthetic construct
SEQUENCE: 31
AIMDKNIIL                                                                   9

SEQ ID NO: 32              moltype = AA  length = 9
FEATURE                   Location/Qualifiers
REGION                    1..9
                          note = Synthetic epitope
source                    1..9
                          mol_type = protein
                          organism = synthetic construct
SEQUENCE: 32
ALLKHRFEI                                                                   9

SEQ ID NO: 33              moltype = AA  length = 9
FEATURE                   Location/Qualifiers
REGION                    1..9
                          note = Synthetic epitope
source                    1..9
                          mol_type = protein
                          organism = synthetic construct
SEQUENCE: 33
DLMGYIPAV                                                                   9

SEQ ID NO: 34              moltype = AA  length = 9
FEATURE                   Location/Qualifiers
REGION                    1..9
                          note = Synthetic epitope
source                    1..9
                          mol_type = protein
                          organism = synthetic construct
SEQUENCE: 34
IMDQVPFSV                                                                   9

SEQ ID NO: 35              moltype = AA  length = 9
FEATURE                   Location/Qualifiers
REGION                    1..9
                          note = Synthetic epitope
source                    1..9
                          mol_type = protein
                          organism = synthetic construct
SEQUENCE: 35
ITDQVPFSV                                                                   9

SEQ ID NO: 36              moltype = AA  length = 9
FEATURE                   Location/Qualifiers
REGION                    1..9
                          note = Synthetic epitope
source                    1..9
                          mol_type = protein
                          organism = synthetic construct
```

-continued

```
SEQUENCE: 36
SLLMWITQA                                                                   9

SEQ ID NO: 37          moltype = AA   length = 9
FEATURE                Location/Qualifiers
REGION                 1..9
                       note = Synthetic epitope
source                 1..9
                       mol_type = protein
                       organism = synthetic construct
SEQUENCE: 37
GLYDGMEHL                                                                   9

SEQ ID NO: 38          moltype = AA   length = 9
FEATURE                Location/Qualifiers
REGION                 1..9
                       note = Synthetic epitope
source                 1..9
                       mol_type = protein
                       organism = synthetic construct
SEQUENCE: 38
FLWGPRALV                                                                   9

SEQ ID NO: 39          moltype = AA   length = 9
FEATURE                Location/Qualifiers
REGION                 1..9
                       note = Synthetic epitope
source                 1..9
                       mol_type = protein
                       organism = synthetic construct
SEQUENCE: 39
KVLEYVIKV                                                                   9

SEQ ID NO: 40          moltype = AA   length = 9
FEATURE                Location/Qualifiers
REGION                 1..9
                       note = Synthetic epitope
source                 1..9
                       mol_type = protein
                       organism = synthetic construct
SEQUENCE: 40
VMNILLQYV                                                                   9

SEQ ID NO: 41          moltype = AA   length = 9
FEATURE                Location/Qualifiers
REGION                 1..9
                       note = Synthetic epitope
source                 1..9
                       mol_type = protein
                       organism = synthetic construct
SEQUENCE: 41
VIVMLTPLV                                                                   9

SEQ ID NO: 42          moltype = AA   length = 9
FEATURE                Location/Qualifiers
REGION                 1..9
                       note = Synthetic epitope
source                 1..9
                       mol_type = protein
                       organism = synthetic construct
SEQUENCE: 42
LNIDLLWSV                                                                   9

SEQ ID NO: 43          moltype = AA   length = 9
FEATURE                Location/Qualifiers
REGION                 1..9
                       note = Synthetic eptitope
source                 1..9
                       mol_type = protein
                       organism = synthetic construct
SEQUENCE: 43
VLFGLGFAI                                                                   9

SEQ ID NO: 44          moltype = AA   length = 10
FEATURE                Location/Qualifiers
REGION                 1..10
                       note = Synthetic epitope
source                 1..10
                       mol_type = protein
```

```
                            organism = synthetic construct
SEQUENCE: 44
ALWGPDPAAA                                                          10

SEQ ID NO: 45              moltype = AA   length = 9
FEATURE                    Location/Qualifiers
REGION                     1..9
                           note = Synthetic epitope
source                     1..9
                           mol_type = protein
                           organism = synthetic construct
SEQUENCE: 45
HLVEALYLV                                                           9

SEQ ID NO: 46              moltype = AA   length = 9
FEATURE                    Location/Qualifiers
REGION                     1..9
                           note = Synthetic epitope
source                     1..9
                           mol_type = protein
                           organism = synthetic construct
SEQUENCE: 46
SLSRFSWGA                                                           9

SEQ ID NO: 47              moltype = AA   length = 10
FEATURE                    Location/Qualifiers
REGION                     1..10
                           note = Synthetic epitope
source                     1..10
                           mol_type = protein
                           organism = synthetic construct
SEQUENCE: 47
YLLPRRGPRL                                                          10

SEQ ID NO: 48              moltype = AA   length = 10
FEATURE                    Location/Qualifiers
REGION                     1..10
                           note = Synthetic epitope
source                     1..10
                           mol_type = protein
                           organism = synthetic construct
SEQUENCE: 48
KLSGLGINAV                                                          10

SEQ ID NO: 49              moltype = AA   length = 10
FEATURE                    Location/Qualifiers
REGION                     1..10
                           note = Synthetic epitope
source                     1..10
                           mol_type = protein
                           organism = synthetic construct
SEQUENCE: 49
LLFNILGGWV                                                          10

SEQ ID NO: 50              moltype = AA   length = 9
FEATURE                    Location/Qualifiers
REGION                     1..9
                           note = Synthetic epitope
source                     1..9
                           mol_type = protein
                           organism = synthetic construct
SEQUENCE: 50
MLDLQPETT                                                           9

SEQ ID NO: 51              moltype = AA   length = 9
FEATURE                    Location/Qualifiers
REGION                     1..9
                           note = Synthetic epitope
source                     1..9
                           mol_type = protein
                           organism = synthetic construct
SEQUENCE: 51
NLVPMVATV                                                           9

SEQ ID NO: 52              moltype = AA   length = 9
FEATURE                    Location/Qualifiers
REGION                     1..9
                           note = Synthetic epitope
source                     1..9
```

-continued

```
                         mol_type = protein
                         organism = synthetic construct
SEQUENCE: 52
LLFGYPVYV                                                          9

SEQ ID NO: 53            moltype = AA   length = 10
FEATURE                  Location/Qualifiers
REGION                   1..10
                         note = Synthetic epitope
source                   1..10
                         mol_type = protein
                         organism = synthetic construct
SEQUENCE: 53
ELAGIGILTV                                                         10

SEQ ID NO: 54            moltype = DNA   length = 61
FEATURE                  Location/Qualifiers
source                   1..61
                         mol_type = other DNA
                         organism = synthetic construct
misc_feature             59..61
                         note = RNA
misc_feature             1..58
                         note = DNA
variation                23..47
                         note = n is a, c, g, or t
SEQUENCE: 54
ctacacgacg ctcttccgat ctnnnnnnnn nnnnnnnnnn nnnnnnnntt tcttatatgg  60
g                                                                  61

SEQ ID NO: 55            moltype = DNA   length = 57
FEATURE                  Location/Qualifiers
variation                14..23
                         note = n is a, c, g, or t
source                   1..57
                         mol_type = other DNA
                         organism = synthetic construct
SEQUENCE: 55
aaagaatata cccnnnnnnn nnngacagag aatatgtgta gaggctcggg tcgtctg     57

SEQ ID NO: 56            moltype = DNA   length = 20
FEATURE                  Location/Qualifiers
source                   1..20
                         mol_type = other DNA
                         organism = synthetic construct
SEQUENCE: 56
gtagaggctc gggtcgtctg                                              20

SEQ ID NO: 57            moltype = DNA   length = 39
FEATURE                  Location/Qualifiers
source                   1..39
                         mol_type = other DNA
                         organism = synthetic construct
SEQUENCE: 57
ggctcgggtc gtctgtagag catacggcag aagacgaac                         39

SEQ ID NO: 58            moltype = DNA   length = 105
FEATURE                  Location/Qualifiers
variation                23..49
                         note = n is a, c, g, or t
variation                62..71
                         note = n is a, c, g, or t
source                   1..105
                         mol_type = other DNA
                         organism = synthetic construct
SEQUENCE: 58
ctacacgacg ctcttccgat ctnnnnnnnn nnnnnnnnnn nnnnnnnntt tcttatatgg  60
gnnnnnnnnn nctgtctctt atacacatct ccgagcccac gagac                 105

SEQ ID NO: 59            moltype = DNA   length = 104
FEATURE                  Location/Qualifiers
variation                23..49
                         note = n is a, c, g, or t
variation                62..71
                         note = n is a, c, g, or t
source                   1..104
                         mol_type = other DNA
                         organism = synthetic construct
misc_feature             1..58
```

-continued

```
                          note = DNA
misc_feature              59..61
                          note = RNA
misc_feature              62..104
                          note = DNA
SEQUENCE: 59
gatgtgctgc gagaaggcta gannnnnnnn nnnnnnnnnn nnnnnnntt tcttatatgg    60
gnnnnnnnnn nctgtcttta tacacatctc cgagcccacg agac                   104

SEQ ID NO: 60             moltype = DNA  length = 48
FEATURE                   Location/Qualifiers
source                    1..48
                          mol_type = other DNA
                          organism = synthetic construct
SEQUENCE: 60
aatgatacgg cgaccaccga gatctacact ctttccctac acgacgtc               48

SEQ ID NO: 61             moltype = DNA  length = 165
FEATURE                   Location/Qualifiers
variation                 59..74
                          note = n is a, c, g, or t
variation                 75..84
                          note = n is a, c, g, or t
variation                 88..97
                          note = n is a, c, g, or t
variation                 98..107
                          note = n is a, c, g, or t
source                    1..165
                          mol_type = other DNA
                          organism = synthetic construct
misc_feature              1..94
                          note = DNA
misc_feature              95..97
                          note = RNA
misc_feature              98..165
                          note = DNA
SEQUENCE: 61
aatgatacgg cgaccaccga gatctacact ctttccctac acgacgctct tccgatctnn   60
nnnnnnnnnn nnnnnnnnnn nnnntttctt atatgggnnn nnnnnnnctg tctcttatac   120
acatctccga gcccacgaga ctagagcata cggcagaaga cgaac                  165

SEQ ID NO: 62             moltype = DNA  length = 165
FEATURE                   Location/Qualifiers
variation                 59..75
                          note = n is a, c, g, or t
variation                 76..84
                          note = n is a, c, g, or t
variation                 89..98
                          note = n is a, c, g, or t
variation                 99..107
                          note = n is a, c, g, or t
source                    1..165
                          mol_type = other DNA
                          organism = synthetic construct
SEQUENCE: 62
ttactatgcc gctggtggct ctagatgtga gaaagggatg tgctgcgaga aggctagann   60
nnnnnnnnnn nnnnnnnnnn nnnnaaagaa tatacccnnn nnnnnnngac agagaatatg   120
tgtagaggct cgggtgctct gatctcgtat gccgtcttct gcttg                  165

SEQ ID NO: 63             moltype = AA  length = 14
FEATURE                   Location/Qualifiers
REGION                    1..14
                          note = Synthetic peptide
source                    1..14
                          mol_type = protein
                          organism = synthetic construct
SEQUENCE: 63
CALMGGTGGF KTIF                                                    14

SEQ ID NO: 64             moltype = AA  length = 11
FEATURE                   Location/Qualifiers
REGION                    1..11
                          note = Synthetic peptide
source                    1..11
                          mol_type = protein
                          organism = synthetic construct
SEQUENCE: 64
CAGYNFNKFY F                                                       11
```

-continued

```
SEQ ID NO: 65            moltype = AA  length = 14
FEATURE                  Location/Qualifiers
REGION                   1..14
                         note = Synthetic peptide
source                   1..14
                         mol_type = protein
                         organism = synthetic construct
SEQUENCE: 65
CAETLNQAGT ALIF                                                  14

SEQ ID NO: 66            moltype = AA  length = 11
FEATURE                  Location/Qualifiers
REGION                   1..11
                         note = Synthetic peptide
source                   1..11
                         mol_type = protein
                         organism = synthetic construct
SEQUENCE: 66
CAVKDTDKLI F                                                     11

SEQ ID NO: 67            moltype = AA  length = 14
FEATURE                  Location/Qualifiers
REGION                   1..14
                         note = Synthetic peptide
source                   1..14
                         mol_type = protein
                         organism = synthetic construct
SEQUENCE: 67
CILRDFQGAQ KLVF                                                  14

SEQ ID NO: 68            moltype = AA  length = 9
FEATURE                  Location/Qualifiers
REGION                   1..9
                         note = Synthetic peptide antigen
source                   1..9
                         mol_type = protein
                         organism = synthetic construct
SEQUENCE: 68
YVLDHLIVV                                                         9
```

What is claimed is:

1. A method of making a library of peptide-MHC class I multimer complexes, each pMHC-I multimer complex in the library comprising an MHC class I multimer and a peptide of interest from a plurality of peptides of interest, the method comprising:

a) incubating a plurality of MHC class I heavy chains, a plurality of MHC class I light chains, and a plurality of placeholder peptides under conditions wherein the plurality of MHC class I heavy chains, MHC class I light chains and placeholder peptides form a plurality of placeholder peptide-MHC class I (p*MHC-I) complexes;

b) contacting the placeholder peptide-MHC class I (p*MHC-I) complexes with Tapasin Binding Protein Related (TAPBPR) chaperone to form peptide deficient-MHC class I/chaperone complexes;

c) multimerizing the peptide deficient-MHC class I/chaperone complexes to form peptide deficient-MHC class I/chaperone multimer complex, wherein each peptide deficient-MHC class I/chaperone multimer complex comprises a backbone comprising a detectable label; and d) contacting each of the peptide deficient-MHC class I/chaperone multimer complexes with a peptide of interest from the plurality of peptides of interest, thereby forming a plurality of peptide-MHC class I multimer complexes.

2. The method of claim 1, wherein the detectable label of each of the peptide-MHC class I multimer complexes in the plurality of peptide-MHC class I multimer complexes corresponds to a different peptide of interest.

3. The method of claim 1, wherein the detectable label comprises a fluorophore or a nucleic acid barcode.

4. The method of claim 1, wherein the placeholder peptide is a destabilizing placeholder peptide with a Tm value for the MHC class I of below 50° C.

5. A method of screening a sample of T cells for antigen specific T cells that bind to one or more peptides from a plurality of peptide of interest comprising:

a) contacting the sample with the library of peptide-MHC class I multimer complexes of claim 1; and b) detecting the presence of T cells in the sample that bind to one or more of the peptide-MHC class I multimer complexes using the detectable label.

6. The method of claim 5, further comprising determining the sequence of the T cell receptor (TCR) of a T cell in the sample that binds a peptide-MHC class I multimer complex using V(D)J sequencing.

7. The method of claim 5, where the detectable label comprises a nucleic acid barcode, further comprising identifying the peptide of a pMHC-I multimer complex bound to a T cell in the sample by determining the nucleic acid barcode of the peptide-MHC class I multimer complex.

8. The method of claim 5 where the detectable label comprises a fluorophore, further comprising detecting the peptide-MHC class I multimer complex by flow cytometry.

* * * * *